(12) United States Patent
Doherty et al.

(10) Patent No.: US 8,183,289 B2
(45) Date of Patent: May 22, 2012

(54) 4-SUBSTITUTED PHENOXYPHENYLACETIC ACID DERIVATIVES

(75) Inventors: George Doherty, Libertyville, IL (US); Adam Cook, Broomfield, CO (US)

(73) Assignee: Array BioPharma Inc., Boulder, CO (US)

( * ) Notice: Subject to any disclaimer, the term of this patent is extended or adjusted under 35 U.S.C. 154(b) by 83 days.

(21) Appl. No.: 12/438,112

(22) PCT Filed: Aug. 21, 2007

(86) PCT No.: PCT/US2007/076378
§ 371 (c)(1),
(2), (4) Date: Jun. 5, 2009

(87) PCT Pub. No.: WO2008/024746
PCT Pub. Date: Feb. 28, 2008

(65) Prior Publication Data
US 2010/0173955 A1    Jul. 8, 2010

Related U.S. Application Data

(60) Provisional application No. 60/839,018, filed on Aug. 21, 2006, provisional application No. 60/851,385, filed on Oct. 13, 2006.

(51) Int. Cl.
| | |
|---|---|
| *C07D 211/22* | (2006.01) |
| *C07D 211/84* | (2006.01) |
| *C07D 333/22* | (2006.01) |
| *C07D 233/00* | (2006.01) |
| *C07C 229/00* | (2006.01) |
| *A01N 37/12* | (2006.01) |
| *A01N 37/44* | (2006.01) |

(52) U.S. Cl. ............... 514/563; 546/316; 548/323.5; 549/77; 562/455

(58) Field of Classification Search ............ None
See application file for complete search history.

(56) References Cited

U.S. PATENT DOCUMENTS
6,469,195 B1 * 10/2002 Grammenos et al. ......... 560/35
7,321,001 B2    1/2008 Fu et al.

FOREIGN PATENT DOCUMENTS
WO    WO 2006/014012    *    2/2006

OTHER PUBLICATIONS

Patani et al. (Chem. Rev., 1996, 96, 3146-76).*
International Search Report for Corresponding PCT Patent Application No. PCT/US2007/076378.
Pettipher, Roy et al., "Antagonism of the Prostaglandin D2 Receptors DP1, and CRTH2 as an Approach to Treat Allergic Diseases", Nature Reviews, Drug Discovery, vol. 6, Apr. 2007, pp. 313-325.
Norman, Peter, "Indole-Based CRTH2 Antagonists", Expert Opin. Ther. Patents (2005) 15(12):1817-1823.

* cited by examiner

*Primary Examiner* — Brandon Fetterolf
*Assistant Examiner* — Anna Pagonakis
(74) *Attorney, Agent, or Firm* — John R. Moore, Esq.; Sarah S. Mastous; Viksnins Harris & Padys PLLP

(57) ABSTRACT

Compounds of Formula (I): in which $R^1$, $R^2$, $R^7$, $R^8$, $R^9$, $R^{10}$ and A have the meanings given in the specification, are DP2 receptor modulators useful in the treatment of immunologic diseases.

(I)

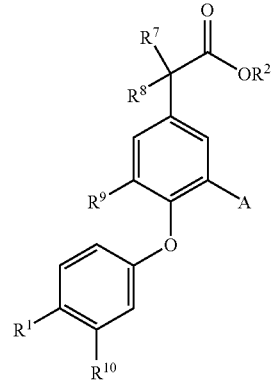

13 Claims, No Drawings

4-SUBSTITUTED PHENOXYPHENYLACETIC ACID DERIVATIVES

This application claims the benefit of U.S. provisional patent application Ser. No. 60/839,018 filed on Aug. 21, 2006 and Ser. No. 60/851,385 filed Oct. 13, 2006, which are incorporated herein by reference in their entirety.

The present invention relates to novel compounds, to pharmaceutical compositions comprising the compounds, to a process for making the compounds and to the use of the compounds in therapy. More particularly it relates to certain 4-substituted phenoxyphenylacetic acid derivatives useful in the treatment and prevention of allergic diseases such as asthma, allergic rhinitis and atopic dermatitis and other inflammatory diseases mediated by prostaglandin $D_2$ ($PGD_2$).

International patent application, publication number WO 2004/058164 discloses inter alia, certain 2-substituted phenoxyphenylacetic acid derivatives that modulate the $PGD_2$-selective receptor CRTH2 (chemoattractant receptor-homologous molecule expressed on Th2 cells), now more commonly referred to as DP2. The compounds are said to be useful in the treatment of immunologic diseases such as asthma and allergic inflammation.

It has now been found that certain 4-substituted phenoxyphenyl acetic acid derivatives bearing a particular substituent meta to the acetic acid moiety are DP2 receptor modulators. As used herein, the term "modulator" includes antagonists.

According to one aspect, the present invention provides a compound of general formula (I):

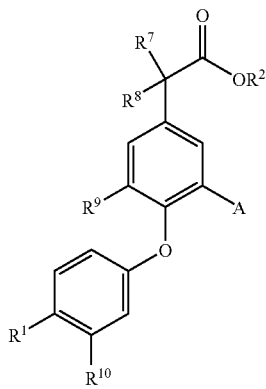

(I)

or a salt thereof, wherein:
$R^1$ is $Ar^1$-$L^1$-W-$L^2$-;
$L^2$ is —$(CR^cR^d)_m$—;
W is —$CONR^{3a}$— or —$NR^{3b}CO$—;
$R^{3a}$ and $R^{3b}$ are each H or methyl;
$L^1$ is —$(CR^aR^b)_n$—, —(CH=CH)—, or —$O(CR^aR^b)$— provided that when W is —$NR^3CO$— then $L^1$ is not —(CH=CH)—;
n and m are independently 0, 1 or 2;
each $R^a$, $R^b$, $R^c$ and $R^d$ is independently H, F, OH, methyl or cyclopropyl, or $R^a$ and $R^b$ or $R^c$ and $R^d$ together with the carbon to which they are attached form a cyclopropyl ring;
$Ar^1$ is phenyl or naphthyl, each of which is unsubstituted or substituted with one or more substituents selected independently from F, Cl, CN, $CF_3$, $CHF_2$, $CH_2F$, $SF_5$, methyl, ethyl, cyclopropyl, t-butyl or OMe, or $Ar^1$ is 1,2,3,4-tetrahydronaphthyl which is unsubstituted or substituted by methoxy, provided that when $Ar^1$ is naphthyl or 1,2,3,4-tetrahydronaphthyl then n is 0;
$R^2$ is H, $C_1$-$C_6$ alkyl, a residue of an amino acid or dipeptide, or $CHR^e(CH_3)_qR^f$;
q is 1 to 6;
$R^c$ is H, methyl or ethyl;
$R^f$ is $NR^gR^h$ in which $R^g$ and $R^h$ each independently represents a hydrogen atom or a $C_1$-$C_4$ alkyl group, or $R^g$ and $R^h$ together with the nitrogen atom to which they are attached form a 5-6 membered heterocyclic ring optionally containing a second ring heteroatom selected from N and O, wherein said heterocyclic ring is optionally substituted with one or more groups independently selected from $C_1$-$C_6$ alkyl;
A is CN, $CH_2NH_2$, $CH_2NR^{4a}C$(=O)$R^5$, or $CH_2NR^{4b}SO_2R^6$, Cl, OMe, (1-4C)alkyl, cyclopropyl, H, F, Br, $CH_2NH$(1-4C alkyl), $CH_2N$(1-4C alkyl)$_2$, thienyl, or phenyl which is unsubstituted or substituted with $SO_2Me$;
$R^{4a}$ and $R^{4b}$ are each H or methyl;
$R^5$ is $C_1$-$C_6$ alkyl, $C_1$-$C_6$ alkoxy, $C_3$-$C_6$ cycloalkyl, hetAr$^1$, or Ar$^2$;
$R^6$ is $C_1$-$C_6$ alkyl, NH($C_1$-$C_6$ alkyl), N($C_1$-$C_6$ alkyl)$_2$, Ar$^3$, or hetAr$^2$;
hetAr$^1$ is a 6 membered heteroaryl which is unsubstituted or substituted with one or more groups independently selected from a halogen atom and a group of formula —$NR^{5a}R^{5b}$ in which each of $R^{5a}$ and $R^{5b}$ independently represents a hydrogen atom or a (1-4C) alkyl group, or together with the nitrogen atom to which they are attached form a pyrrolidinyl, piperidinyl or morpholino group;
hetAr$^2$ is a 5-6 membered heteroaryl which is unsubstituted or substituted with one or more groups independently selected from $C_1$-$C_4$ alkyl;
Ar$^2$ is phenyl which is unsubstituted or substituted with one or more groups independently selected from a halogen atom, CN, $SF_5$, cyclopropyl, a $C_1$-$C_4$, alkyl group, a $C_1$-$C_4$ alkoxy group and a fluoro$C_1$-$C_4$ alkyl group;
Ar$^3$ is as defined for Ar$^2$;
$R^7$ and $R^8$ are independently H, methyl, or F;
$R^9$ is H or methyl; and
$R^{10}$ is H or F.

In certain embodiments, the compound of Formula I has the Formula Ia

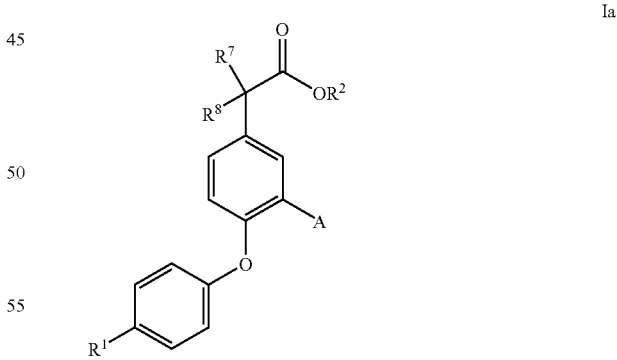

Ia wherein:
$R^1$ is $Ar^1$-$L^1$-W-$L^2$-;
$L^2$ is —$(CR^cR^d)_m$—;
W is —$CONR^{3a}$— or —$NR^{3b}CO$—;
$R^{3a}$ and $R^{3b}$ are each H or methyl;
$L^1$ is —$(CR^aR^b)_n$—, —(CH=CH)—, or —$O(CR^aR^b)$— provided that when W is —$NR^3CO$— then $L^1$ is not —(CH=CH)—;
n and m are independently 0, 1 or 2;

each $R^a$, $R^b$, $R^c$ and $R^d$ is independently H, F, methyl or cyclopropyl, or $R^a$ and $R^b$ or $R^c$ and $R^d$ together with the carbon to which they are attached form a cyclopropyl ring;

$Ar^1$ is phenyl or naphthyl, each of which is unsubstituted or substituted with one or more substituents selected independently from F, Cl, CN, $CF_3$, $CHF_2$, $CH_2F$, $SF_5$, methyl, ethyl, cyclopropyl, provided that when $Ar^1$ is naphthyl then n is 0;

$R^2$ is H, $C_1$-$C_6$ alkyl, a residue of an amino acid or dipeptide, or $CHR^e(CH_2)_qR^f$;

q is 1 to 6;

$R^e$ is H, methyl or ethyl;

$R^f$ is $NR^gR^h$ in which $R^g$ and $R^h$ each independently represents a hydrogen atom or a $C_1$-$C_4$ alkyl group, or $R^g$ and $R^h$ together with the nitrogen atom to which they are attached form a 5-6 membered heterocyclic ring optionally containing a second ring heteroatom selected from N and O, wherein said heterocyclic ring is optionally substituted with one or more groups independently selected from $C_1$-$C_6$ alkyl;

A is CN, $CH_2NH_2$, $CH_2NR^{4a}C(=O)R^5$, or $CH_2NR^{4b}SO_2R^6$, Cl, OMe, (1-4C)alkyl, cyclopropyl;

$R^{4a}$ and $R^{4b}$ are each H or methyl;

$R^5$ is $C_1$-$C_6$ alkyl, $C_1$-$C_6$ alkoxy, $C_3$-$C_6$ cycloalkyl, $hetAr^1$, or $Ar^2$;

$R^6$ is $C_1$-$C_6$ alkyl, $NH(C_1$-$C_6$ alkyl), $N(C_1$-$C_6$ alkyl$)_2$, $Ar^3$, or $hetAr^2$;

$hetAr^1$ is a 6 membered heteroaryl which is unsubstituted or substituted with one or more groups independently selected from a halogen atom and a group of formula —$NR^{5a}R^{5b}$ in which each of $R^{5a}$ and $R^{5b}$ independently represents a hydrogen atom or a (1-4C) alkyl group, or together with the nitrogen atom to which they are attached form a pyrrolidinyl, piperidinyl or morpholino group;

$hetAr^2$ is a 5-6 membered heteroaryl which is unsubstituted or substituted with one or more groups independently selected from $C_1$-$C_4$ alkyl;

$Ar^2$ is phenyl which is unsubstituted or substituted with one or more groups independently selected from a halogen atom, CN, $SF_5$, cyclopropyl, a $C_1$-$C_4$ alkyl group, a $C_1$-$C_4$ alkoxy group and a fluoro$C_1$-$C_4$ alkyl group;

$Ar^3$ is as defined for $Ar^2$; and $R^7$ and $R^8$ are independently H, methyl.

Compounds according to the present invention have been found to be DP2 modulators and are useful in the treatment of immunologic diseases such as asthma and allergic inflammation.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of formula (I) or their salts may be isolated in the form of solvates, and accordingly that any such solvate is included within the scope of the present invention.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

The term "halogen" as used herein includes F, Cl, Br and I.

The terms "$C_1$-$C_4$ alkyl" and "$C_1$-$C_6$ alkyl" as used herein refer to a saturated linear or branched-chain monovalent hydrocarbon radical of one to four or one to six carbon atoms, respectively. Examples of alkyl groups include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

The term "heteroaryl" as used herein refers to a monovalent aromatic radical of a 5-, 6-, or 7-membered ring. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, and pyrrolyl.

The term "fluoro$C_1$-$C_4$ alkyl" as used herein refers to a $C_1$-$C_4$ alkyl group wherein one or more of the hydrogens is replaced by a fluorine atom. Examples include $CF_3$, $CH_2F$, $CHF_2$, $CH_2CH_2F$, $CH_2CH_2F_2$, $CH_2CF_3$, $CH_2CH_2CH_2F$, $CH_2CH_2CHF_2$, $CH_2CH_2CF_3$, $CHF(CH_3)_2$, $CH_2CHF(CH_3)_2$, and the like.

The term "$C_1$-$C_6$ alkoxy" as used herein refers to a $C_1$-$C_6$ alkyloxy group. Exemplary alkoxy groups include methoxy, ethoxy, propoxy, isopropoxy, butoxy, t-butoxy, and isobutoxy.

In one embodiment, W is —$CONR^{3a}$—. An example of a particular value for $R^{3a}$ is hydrogen. In one embodiment, W is —$NR^{3b}CO$—. In one embodiment $R^{3b}$ is hydrogen. In another embodiment, $R^{3b}$ is methyl. Examples of particular values for W are CONH, NHCO and $N(CH_3)CO$.

In one embodiment, $L^1$ is —$(CR^aR^b)_n$—. Examples of particular values for n are 0, 1 and 2.

In one embodiment, $L^1$ is a bond.

In one embodiment, $L^1$ is —$(CR^aR^b)$. In certain embodiments, $R^a$ and $R^b$ are hydrogen. In certain embodiments, $R^a$ is OH. In certain embodiments, $R^a$ and $R^b$ together with the carbon atom to which are attached form a cyclopropylidine ring.

In one embodiment, $L^1$ is —$(CR^aR^b)_2$. In certain embodiments, $R^a$ and $R^b$ are hydrogen. In certain embodiments, $R^a$ and $R^b$ together with the carbon atom to which are attached form a cyclopropylidine ring. In certain embodiments, $R^a$ and $R^b$ are attached to the same carbon. In other embodiments, $R^a$ and $R^b$ are attached to different carbon atoms.

Examples of particular values for $L^1$ are a bond, —$CH_2$—, —$CH_2CH_2$— and cyclopropylidene$CH_2$.

A further example of $L^1$ includes $CH(OH)CH_2$.

Further examples of $L^1$ include cyclopropylidine groups, which can be represented by the following structures:

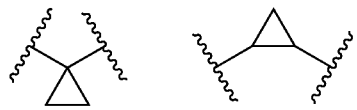

In one embodiment, $L^1$ is —$O(CR^aR^b)$—. An exemplary embodiment is —$OCH_2$—.

Referring to $L^2$, examples of particular values for m are 0 and 1. Examples of particular values for $L^2$ are a bond and —$CH_2$—.

In certain embodiments, the sum of m and n is 0, 1 and 2. Particular mention is made of compounds in which the sum of m and n is 0 or 2.

Examples of values for -$L^1$-W-$L^2$- include —CONH—, —$CH_2CONH$—, —$CH_2CH_2CONH$—, —$CONHCH_2$—, —$CH_2CONHCH_2$—, —NHCO—, —$CH_2NHCO$—, —NHCO$CH_2$—, —$CH_2CH_2NHCO$—, —$CH_2NHCOCH_2$—, —CH₂CH₂NHCOCH₂—, —CH₂N(CH₃)COCH₂—, cyclopropylideneCH₂NHCO and —CH₂ONHCO—.

Further examples of values for -L¹-W-L²- include —CH(OH)CH₂NHCO— and -cyclopropylidineNHCO—.

Particular values of -L¹-W-L²- are —CONH—, —NHCO—, —CH₂NHCO—, —NHCOCH₂—, —CH₂CH₂NHCO—, —CH₂NHCOCH₂—, —CH₂CH₂NHCOCH₂—, —CH₂N(CH₃)COCH₂—, cyclopropylideneCH₂NHCO, —CH(OH)CH₂NHCO— and -cyclopropylidineNHCO—.

In one embodiment, Ar¹ is a naphthyl group or a phenyl group that is substituted by one or two substituents independently selected from F, ClCF₃, OMe, Me, and t-Bu.

In one embodiment, Ar¹ is a naphthyl group or a phenyl group that is unsubstituted or substituted by one or two substituents selected independently from F, Cl and CF₃.

In one embodiment, Ar¹ is a naphthyl group or a phenyl group that is substituted by one or two substituents independently selected from OMe, Me, and t-Bu.

In one embodiment, Ar¹ is 1,2,3,4-tetrahydronaphthyl which is unsubstituted or substituted with OMe. In a particular embodiment, A is selected from the structures:

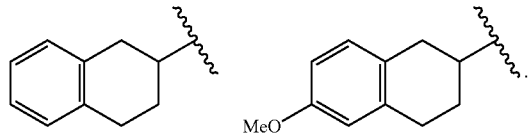

Examples of particular values for Ar¹ are naphthyl, phenyl, 4-fluorophenyl, 3,4-difluorophenyl, 2-chlorophenyl, 3-chlorophenyl, 4-chlorophenyl, 3,4-dichlorophenyl, 4-chloro-3-fluorophenyl, 3-chloro-4-fluorophenyl, 4-trifluoromethylphenyl, 3-fluoro-4-trifluoromethylphenyl, 3-trifluoromethylphenyl, 2,6-dichlorophenyl, 2,4-dichlorophenyl, 3-methoxy phenyl, 4-methoxyphenyl, 4-tertbutylphenyl, 3-fluorophenyl, 4-methylphenyl, 1,2,3,4-tetrahydronaphth-2-yl and 6-methoxy-1,2,3,4-tetrahydronaphth-2-yl.

In certain embodiments, Ar¹ is selected from naphthyl, phenyl, 4-fluorophenyl, 3,4-difluorophenyl, 2-chlorophenyl, 3-chlorophenyl, 4-chlorophenyl, 3,4-dichlorophenyl, 4-chloro-3-fluorophenyl, 3-chloro-4-fluorophenyl, 4-trifluoromethylphenyl and 3-fluoro-4-trifluoromethylphenyl.

In certain embodiments, Ar¹ is selected from 3-trifluoromethylphenyl, 2,6-dichlorophenyl, 2,4-dichlorophenyl, 3-methoxyphenyl, 4-methoxyphenyl, 4-tertbutylphenyl, 3-fluorophenyl and 4-methylphenyl, and 1,2,3,4-tetrahydronaphth-2-yl and 6-methoxy-1,2,3,4-tetrahydronaphth-2-yl.

In one embodiment, A is CN.

In one embodiment, A is H.

In one embodiment, A is selected from F, Br and Cl.

In one embodiment, A is selected from (1-4C)alkyl. Particular examples include methyl and ethyl.

In one embodiment, A is cyclopropyl.

In one embodiment, A is selected from CH₂NH₂, CH₂NH(1-4C alkyl), and CH₂N(1-4C alkyl)₂. Particular examples include CH₂NH₂ and CH₂NMe₂.

In one embodiment, A is thienyl. In a particular embodiment, A is 2-thienyl.

In one embodiment, A is phenyl which is unsubstituted or substituted with SO₂Me. Particular examples include phenyl, 3-methylsulfonylphenyl, and 4-methylsulfonylphenyl.

In one embodiment, A is CH₂NR⁴ᵃC(=O)R⁵. An example of a particular value for R⁴ᵃ is hydrogen. In one embodiment, R⁵ is hetAr¹. An example of a particular value for a heteroaryl group represented by hetAr¹ is a pyridyl group. Examples of optional substituents on the heteroaryl group are NH₂, Cl, and pyrrolidinyl.

In another embodiment, R⁵ is C₁-C₆ alkyl; C₁-C₆ alkoxy; C₃-C₆ cycloalkyl; pyridyl which is unsubstituted or substituted by a halogen atom or a group of formula —NR⁵ᵃR⁵ᵇ in which each of R⁵ᵃ and R⁵ᵇ independently represents a hydrogen atom or a (1-4C) alkyl group, or together with the nitrogen atom to which they are attached form a pyrrolidinyl, piperidinyl or morpholino group; or a phenyl group that is unsubstituted or substituted by one or two halogen atoms.

Examples of particular values for R⁵ are methyl, methoxy, cyclohexyl, pyrid-2-yl, pyrid-3-yl, pyrid-4-yl, 6-chloro-pyrid-3-yl, 6-amino-pyrid-3-yl, 6-pyrrolidin-1-ylpyrid-3-yl or 4-fluorophenyl. An additional example of R⁵ is 6-dimethylaminopyrid-3-yl.

In one embodiment, A is CH₂NR⁴ᵇSO₂R⁶. An example of a particular value for R⁴ᵇ is hydrogen. In one embodiment, R⁶ is hetAr². Examples of particular values for a heteroaryl group represented by hetAr² are an imidazolyl and a pyridyl group. Examples for optional substituents on the heteroaryl group are C₁-C₄ alkyl, for example methyl.

In another embodiment, R⁶ is C₁-C₆ alkyl, NH(C₁-C₆ alkyl), N(C₁-C₆ alkyl)₂, a phenyl group that is unsubstituted or substituted by one or two halogen atoms, pyridyl or imidazolyl that is unsubstituted or substituted with a C₁-C₃ alkyl group.

Examples of particular values for R⁶ are methyl, dimethylamino, 4-fluorophenyl, 2,4-dichlorophenyl, pyrid-3-yl and 1-methylimidazol-5-yl. An additional example of R⁶ is pyrid-4-yl.

Examples of particular values for A are acetamidomethyl, cyclohexylamidomethyl, methoxycarbonylaminomethyl, picolinamidomethyl, nicotinamidomethyl, isonicotinamidomethyl, 6-chloropyrid-3-ylamidomethyl, 6-aminopyrid-3-ylamidomethyl, 6-pyrrolidin-1-ylpyrid-3-ylamidomethyl, 4-fluorobenzamidomethyl, methylsulfonamidomethyl, N,N-dimethylsulfamoylamino, 4-fluorophenylsulfonamidomethyl, 2,4-dichlorophenyl-sulfonamidomethyl, 1-methylimidazol-5-ylsulfonamidomethyl and pyrid-3-ylsulfonamidomethyl, which can be represented by the following structures, respectively:

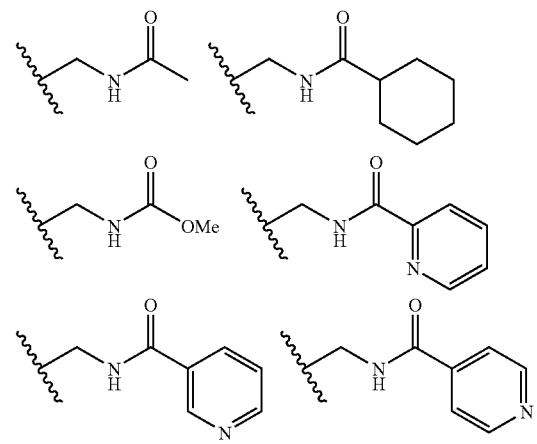

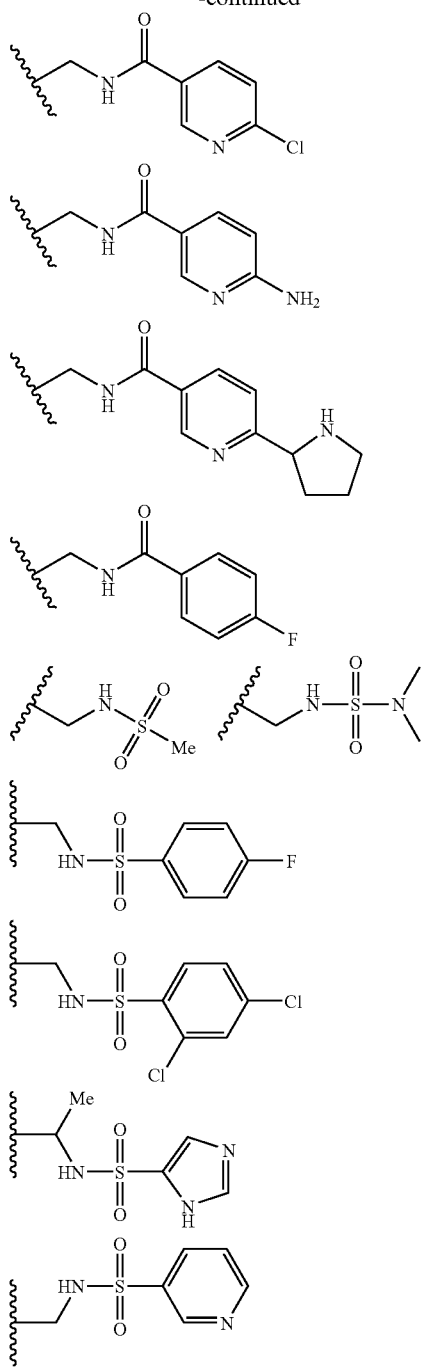

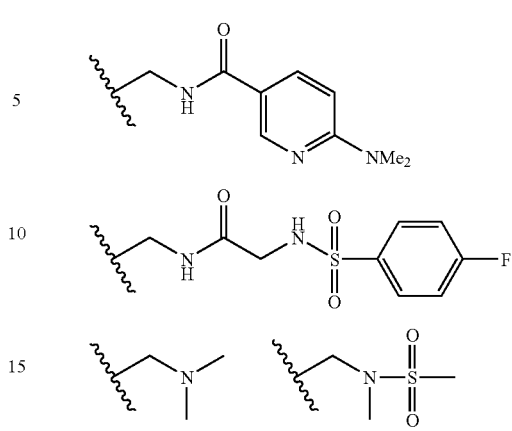

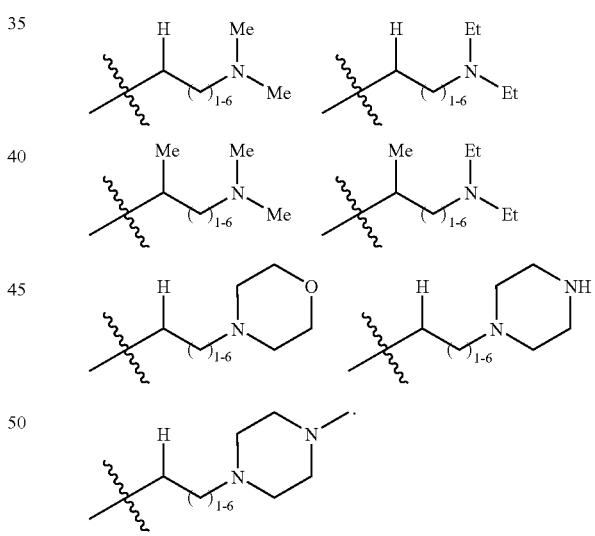

Particular mention is made of acetamidomethyl, cyclohexylamidomethyl, methoxycarbonylaminomethyl, picolinamidomethyl, nicotinamidomethyl, isonicotinamidomethyl, 4-fluorobenzamidomethyl, methylsulfonamidomethyl, N,N-dimethylsulfamoylamino, 4-fluorophenylsulfonamidomethyl, 2,4-dichlorophenylsulfonamidomethyl and pyrid-3-ylsulfonamidomethyl.

Particular values for A also include 6-dimethylaminopyrid-3-ylamidomethyl, 2-(4-fluorophenylsulfonamido)acetamidomethyl, dimethylaminomethyl and (N-methylmethylsulfonamido)methyl, which can be represented by the following structures, respectively:

Examples of particular values for $R^2$ when it represents a $C_1$-$C_6$ alkyl group are methyl, ethyl, propyl, isopropyl and t-butyl.

In one embodiment, $R^2$ is $CHR^e(CH_2)_qR^f$. Examples of values for $R^e$ are hydrogen and methyl. In one embodiment, $R^f$ is di(1-4C)alkylamino, morpholino, or piperazinyl optionally substituted with (1-4C)alkyl. Examples of particular values for $R^f$ are dimethylamino, diethylamino, morpholino, piperazinyl and 1-methylpiperazinyl. Additional examples include $NH_2$ and NHMe.

Examples of particular values for $R^2$ when it represents $CHR^e(CH_2)_qR^f$ are:

In one embodiment, $R^2$ is hydrogen.

On one embodiment, both $R^7$ and $R^8$ are H. In certain embodiments, $R^7$ is H and $R^8$ is methyl. In other embodiments, each of $R^7$ and $R^8$ is methyl.

According to another aspect, the present invention provides a process for the preparation a compound of formula (I) or a salt thereof as defined hereinabove, which comprises:

(a) for a compound of formula (I) in which A is CN, $R^7$ and $R^8$ are independently H or Me, and $R^{10}$ is H or F, reacting a corresponding compound having the formula:

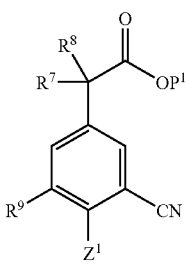
(II)

in which P¹ represents a hydrogen atom or a carboxyl protecting group and Z¹ represents a leaving atom or group, with a corresponding compound having the formula

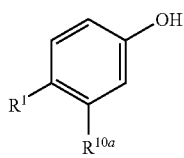
(III)

in which $R^{10a}$ is H or F in the presence of a base; or (b) for a compound of formula (I) in which A is —CH₂NH₂, R¹⁰ is H, and R⁷ and R⁸ are independently H or Me, reducing a corresponding compound formula (IV)

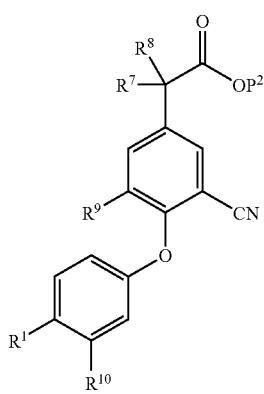
(IV)

in which P² is as defined for P¹; or (c) for a compound of formula (I) in which A is —CH₂NH₂, R⁷ and R⁸ are independently H or Me and R¹⁰ is H, cleaving a corresponding compound of formula (V)

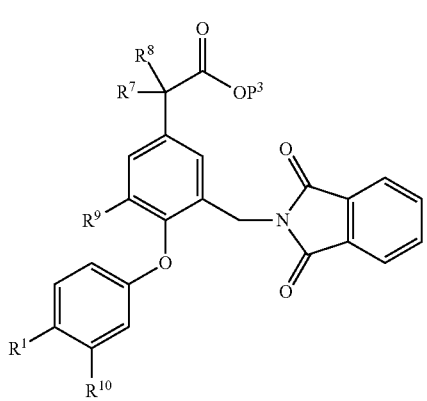
(V)

in which P³ is as defined for P¹; or (d) for a compound of formula (I) in which A is CH₂NR⁴C(=O)R⁵ or CH₂NR⁴SO₂R⁶, R⁷ and R⁸ are independently H or Me, and R¹⁰ is H, reacting a corresponding compound of formula (VI)

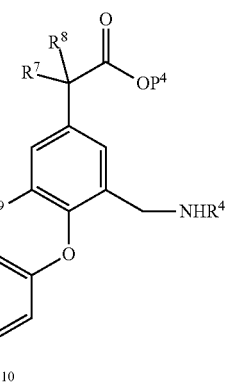
(VI)

in which P⁴ is as defined for P¹; with a compound of formula R⁵COZ² or R⁶SO₂Z³, respectively, in which Z² and Z³ each represents a leaving atom or group; or (e) for a compound of formula (I) in which R⁷ and R⁸ are independently H or Me, and R¹⁰ is H, coupling a compound of formula (VII)

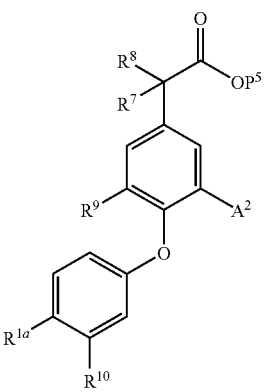
(VII)

in which P⁵ is as defined for P¹, P² represents A or a protected form thereof and $R^{1a}$ represents H—$X^a$-$L^2$- in which $X^a$ represents HN or OC(=O), or a reactive derivative thereof; with a compound of formula (VIII)

Ar¹-L¹-$X^b$-H    (VIII)

in which $X^b$ represents C(=O)O or NH, or a reactive derivative thereof; or (f) for a compound of formula (I) in which A is H, F or Cl, R⁷ and R⁸ are independently H or Me, and R¹⁰ is H, coupling a corresponding compound having the formula (IX)

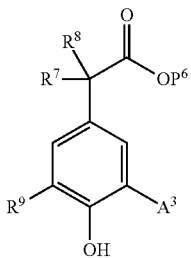

(IX)

in which $A^3$ is H, F or Cl, and $P^6$ is as defined for $P^1$, with a corresponding compound having the formula (X)

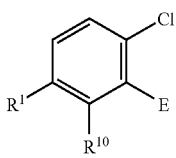

(X)

wherein E is an electron withdrawing group, in the presence of a base; and if desired removing said electron withdrawing group; or (g) for a compound of formula (I) in which A is OMe or (1-4C)alkyl, $R^7$ and $R^8$ are independently H or Me, and $R^{10}$ is H, coupling a corresponding compound having the formula (XI)

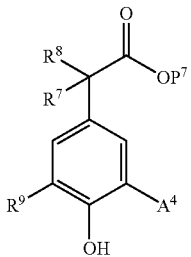

(XI)

in which $A^4$ is OMe or (1-4C)alkyl, respectively, and $P^7$ is as defined for $P^1$, with a corresponding compound having the formula (XII)

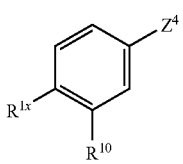

(XII)

in the presence of a base, in which $Z^4$ represents a leaving atom or group, and $R^{1x}$ represents an electron withdrawing group convertible into a group $R^1$; or (h) for a compound of formula (I) in which A is Br or cyclopropyl, $R^7$ and $R^8$ are H, and $R^{10}$ is H, coupling a corresponding compound having the formula (XIV)

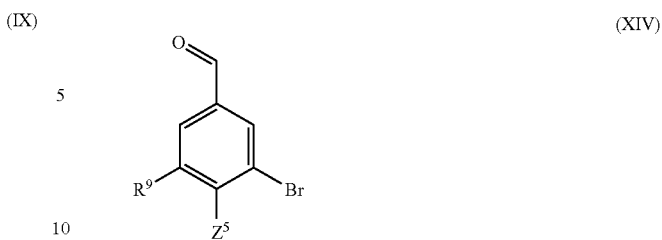

(XIV)

in which $Z^5$ is a leaving group or atom, with a compound having the formula (XV)

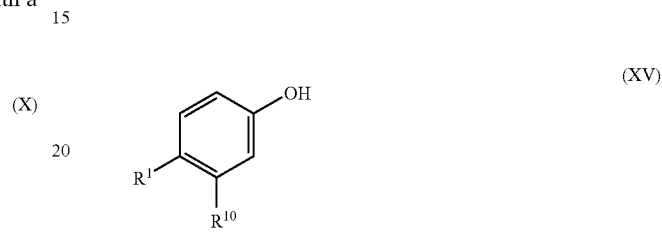

(XV)

in the presence of a base, followed by converting the carbonyl group to a carboxyl group; or (i) for a compound of formula (I) in which A is methyl, thienyl, phenyl, or phenyl substituted with $SO_2Me$, $R^9$ is H, $R^7$ and $R^8$ are independently H or Me, and $R^{10}$ is H, reacting a corresponding compound having the formula (XVI)

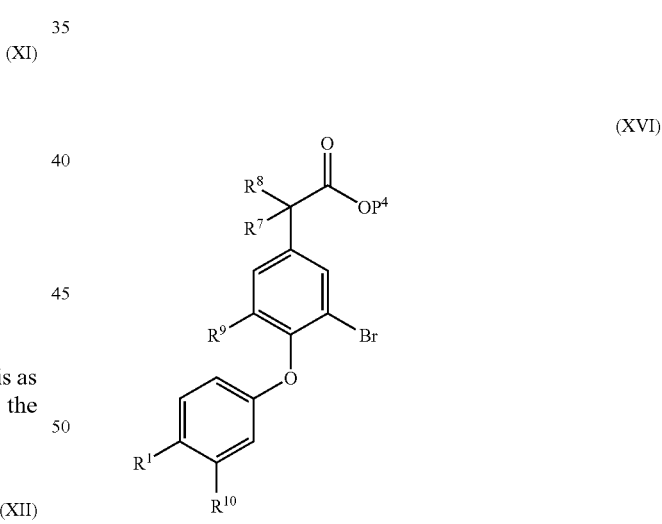

(XVI)

with a compound having the formula $A^5$-ZnX, in the presence of a palladium (0) catalyst, or with a compound having the formula $A^5B(OH)_2$ in the presence of a base and a palladium (0) catalyst, where $A^5$ is methyl, thienyl, phenyl, or phenyl substituted with $SO_2Me$ and X is a halide; or (j) for a compound of formula (I) in which $R^7$ is F, $R^8$ is H, and $R^{10}$ is H, treating a corresponding compound having the formula (XVII)

(XVII)

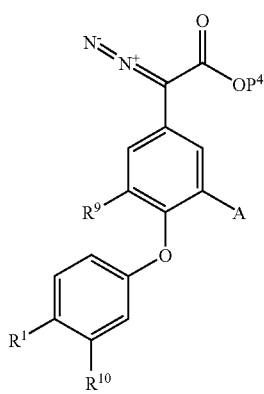

with hydrogen fluoride;

(k) for a compound of Formula (I) in which A is CH$_2$NH (1-4C alkyl) or, CH$_2$N(1-4C alkyl)$_2$, R$^7$ and R$^8$ are independently H or Me, and R$^{10}$ is H, reacting a corresponding compound having the formula

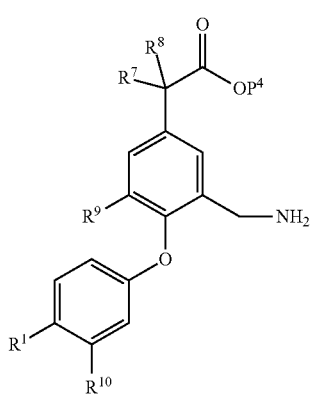

with an aldehyde having the formula HC(O)(1-4C alkyl); and removing any protecting group or groups and, if desired, forming a salt.

Referring to process (a), the leaving atom or group represented by Z$^1$ may be, for example, a halogen atom such as a fluorine atom. The carboxyl protecting group may be any convenient carboxyl protecting group, for example as described in Greene & Wuts, eds., "Protecting Groups in Organic Synthesis", John Wiley & Sons, Inc. Examples of carboxyl protecting groups include (1-6C)alkyl groups, such as methyl, ethyl and t-butyl. The base may be, for example, an alkali metal hydride or carbonate, such as sodium hydride, sodium carbonate or potassium carbonate, or a tertiary amine, such as triethylamine or N,N-diisopropylethylamine. Convenient solvents include amides, sulfoxides and nitriles, such as DMF, DMSO or acetonitrile. The reaction can be performed at an elevated temperature, such as in the range of from 50 to 150° C.

Compounds of formula (II) are known or can be prepared from the corresponding 3-halo compound, such as a 3-bromo compound, by treatment with CuCN.

Referring to process (b), the compound of formula (IV) can be reduced by hydrogenation in the presence of a Group VIII metal catalyst, such as Rancy Ni with methanol/ammonia. The reaction can be conducted at a temperature in the range of from 0 to 100° C.

Referring to process (c), the dioxoisoindolinyl group can be cleaved using HBr and acetic acid or hydrazine.

Compounds of formula (V) can be prepared by reacting a compound of formula (XIII)

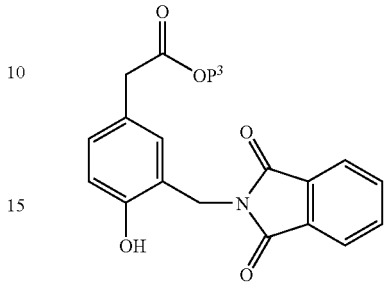

with a compound of formula (XII)

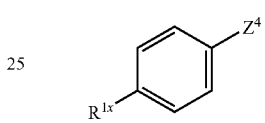

in the presence of a base, in which Z$^4$ represents a leaving atom or group, such as a fluorine atom, and R$^{1x}$ represents an electron withdrawing group convertible into a group R$^1$, for example a nitro group that can be reduced to an amino group and then acylated. The base may be, for example, an alkali metal hydride or carbonate, such as sodium hydride, sodium carbonate or potassium carbonate.

Compounds of formula (IX) can be prepared by reacting 4-hydroxyphenylacetic acid with 2-(hydroxymethyl)isoindoline-1,3-dione in the presence of a sulfonic acid, such as methanesulfonic acid, and followed if desired by introducing a protecting group P$^3$.

Referring to process (d), the leaving atom or group represented by Z$^2$ and Z$^3$ may be, for example, a halogen atom such as a fluorine atom. The reaction can be performed in the presence of a base, for example a tertiary amine such as diisopropylethylamine or pyridine. Convenient solvents include halogenated hydrocarbons, such as methylene chloride. The reaction can be conducted at a temperature in the range of from 0 to 100° C.

Referring to process (e), the coupling of the compound of formula (VII) with a compound of formula (VIII) may be performed using conventional amide bond formation conditions, for example by reacting an amine with a reactive derivative of a carboxylic acid, for example an acid halide, such as an acid chloride. An example of A$^1$ when it represents a protected form of A is a group of formula —CH$_2$NR$^4$P$^6$ in which P$^6$ represents an amine protecting group. The amine protecting group may be any convenient amine protecting group, for example as described in Greene & Wuts, eds., "Protecting Groups in Organic Synthesis", John Wiley & Sons, Inc. Examples of amine protecting groups include acyl and alkoxycarbonyl groups, such as t-butoxycarbonyl (BOC).

Referring to process (f), examples of electron withdrawing groups include NO$_2$. In embodiments wherein the electron withdrawing group is NO$_2$, this group can be removed, if desired, by reducing the nitro group to an amino group using any convenient reducing conditions (for example, Zn and NH$_4$Cl) followed by cleavage of the amino group (for example, by treating the amino compound with isobutyl nitrite).

Referring to process (g), the base may be, for example, an alkali metal hydride or carbonate, such as sodium hydride, sodium carbonate or potassium carbonate. The Z$^4$ group represents a suitable leaving atom or group, such as a fluorine atom, and R$^{1x}$ represents an electron withdrawing group convertible into a group R$^1$, for example a nitro group that can be reduced to an amino group and then acylated.

Referring to process (h), the leaving atom or group represented by Z$^5$ may be, for example, a halogen atom such as a fluorine atom. The base may be, for example, an alkali metal hydride or carbonate, such as sodium hydride, sodium carbonate, or potassium carbonate. Convenient solvents include sulfoxides such as DMSO. The reaction can be performed at elevated temperatures, for example in the range of 50-100° C., for example at 85° C. The carbonyl group can be converted to a carboxyl group by treating the coupling product with methylsulfonyl/methylthiomethane to provide an intermediate having the formula (XVIII)

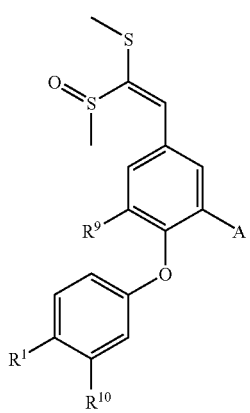

(XVIII)

followed by converting the intermediate (XVIII) to the corresponding methyl ester upon treatment with HCl in methanol. The ester can be converted to the corresponding acid under standard hydrolysis conditions.

Referring to process (i), the halide represented by X can be F, Cl or Br. Convenient solvents include ethers such as THF or dioxane. Suitable palladium (0) catalysts include Pd(PPh$_3$)$_4$ and bis(tri-t-butylphosphine)palladium (0). A convenient base when compound (XVI) is reacted with a boronic acid reagent includes DBU. The reaction can be performed at elevated temperatures, for example in the range of 50-100° C., for example 60° C.

Referring to process (j), the reaction is conveniently performed in the presence of an amine base, for example pyridine.

Referring to process (k), the reaction is conveniently performed in the presence of a base, for example a hydride such as sodium cyanoborohydride in an alcohol solvent such as methanol. The reaction is preferably performed in the presence of a catalytic amount of acid, for example acetic acid. The reaction is conveniently performed at ambient temperature.

The ability of test compounds to act as DP2 receptor modulators may be demonstrated by the assay described in Example A.

Compounds which are modulators of DP2 are useful in the treatment of diseases or disorders mediated by PGD$_2$, for example, diseases or disorders associated with overproduction or dysregulation of PGD$_2$.

As used herein, the term treatment includes prophylaxis as well as treatment of an existing condition.

Examples of disorders or diseases that may be treated with compounds according to the invention include immunologic diseases.

Examples of immunologic diseases include allergic inflammatory diseases, such as asthma, atopic dermatitis, allergic rhinitis, seasonal allergies, food allergies, contact hypersensitivity (e.g., nickel sensitivity), hyper-eosinophilic syndromes, and allergic conjunctivitis.

Additional diseases or disorders which may be treated with the compounds of this invention include inflammatory bowel diseases such as Crohn's disease, ulcerative colitis, ileitis and enteritis, vasculitis, Behcet's syndrome, psoriasis and inflammatory dermatoses such as dermatitis, eczema, urticaria, viral cutaneous pathologies such as those derived from human papillomavirus, HIV or RLV infection, bacterial, fungal and other parasital cutaneous pathologies, and cutaneous lupus erythematosus, respiratory allergic diseases such as persensitivity lung diseases, chronic obstructive pulmonary disease and the like, autoimmune diseases, such as arthritis (including rheumatoid and psoriatic), systemic lupus erythematosus, type I diabetes, myasthenia gravis, multiple sclerosis, Graves' disease, glomerulonephritis and the like, graft rejection (including allograft rejection and graft-v-host disease), e.g., skin graft rejection, solid organ transplant rejection, bone marrow transplant rejection, fever, cardiovascular disorders such as acute heart failure, hypotension, hypertension, angina pectoris, myocardial infarction, cardiomyopathy, congestive heart failure, atherosclerosis, coronary artery disease, restenosis, thrombosis and vascular stenosis, cerebrovascular disorders such as traumatic brain injury, stroke, ischemic reperfusion injury and aneurysm, cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system, fibrosis, connective tissue disease and sarcoidosis, genital and reproductive conditions such as erectile dysfunction, gastrointestinal disorders such as gastritis, ulcers, nausea, pancreatitis and vomiting; neurologic disorders, such as Alzheimer's disease, sleep disorders such as insomnia, narcolepsy, sleep apnea syndrome and Pickwick Syndrome, pain, renal disorders, ocular disorders such as glaucoma, infectious diseases, viral infections such as HIV, and bacterial infections such as sepsis, inflammation, flushing, nasal congestion, and otitis media.

Accordingly, another aspect of this invention provides a method of treating diseases or medical conditions in a mammal mediated by PGD2, comprising administering to said mammal one or more compounds of Formula I or a pharmaceutically acceptable salt or prodrug thereof in an amount effective to treat or prevent said disorder.

The phrase "effective amount" means an amount of compound that, when administered to a mammal in need of such treatment, is sufficient to (i) treat or prevent a particular disease, condition, or disorder mediated by PGD2, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

This invention also provides compounds of Formula I for use in the treatment of PGD2-mediated conditions.

An additional aspect of the invention is the use of a compound of Formula I in the preparation of a medicament for therapy, such as for the treatment or prevention PGD2-mediated conditions.

The compounds of the present invention can be used in combination with one or more additional drugs, for example an anti-inflammatory compound that works by a different mechanism of action.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of formula (I) or a pharmaceutically acceptable salt thereof, as defined hereinabove. In one embodiment, the pharmaceutical composition includes the compound of formula (I) together with a pharmaceutically acceptable diluent or carrier.

According to another aspect, the present invention provides a compound of formula (I) or a pharmaceutically acceptable salt thereof, for use in therapy.

According to a further aspect, the present invention provides the use of a compound of formula (I) or a pharmaceutically acceptable salt thereof, in the manufacture of a medicament to treat an immunologic disorder, as defined hereinabove.

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$HNMR spectra were obtained as CDCl$_3$, CD$_3$OD, D$_2$O or d$_6$-DMSO solutions (reported in ppm), using tetramethylsilane (0.00 ppm) or residual solvent (CDCl$_3$: 7.25 ppm; CD$_3$OD: 3.31 ppm; D$_2$O: 4.79 ppm; d$_6$-DMSO: 2.50 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

EXAMPLE A

DP-2 Binding Inhibition Assay

The coding sequence of human DP2 was introduced into the human Leukemic cell line K562 by electroporation and stable clones expressing DP2 were obtained by limiting dilution followed by cell surface staining with a rat monoclonal antibody specific for human DP2. Membranes were prepared from one of these DP2 expressing clones and used to determine the ability of the compounds of the present invention to inhibit binding of prostaglandin D2 (PGD2) to its receptor DP2 by the following procedure. Membranes (1.25 µg/well) were mixed with $^3$H-labeled PGD$_2$ and various concentrations of test compounds in 150 µL of binding buffer (50 mM Tris-HCl, pH 7.4, 40 mM MgCl$_2$, 0.1% bovine serum albumin, 0.1% NaN$_3$) in 96-well U-bottom polypropylene plates. After incubation for 60 minutes at room temperature, the assay was transferred to a filtration plate (#MAFB; Millipore Corporation, Bedford, MA), and washed three times with binding buffer. Radioactivity was measured by a scintillation counter (TopCount; PerkinElmer Life Sciences, Boston, MA). Nonspecific binding was determined by incubations in the presence of 1 µM unlabeled PGD$_2$ or 5 µM of a known DP2 antagonist. IC$_{50}$ values for inhibition of binding are determined for each compound tested from the inflexion point of a standard 4-parameter logistical curve fitted to the values obtained. All compounds disclosed herein had IC$_{50}$ values less than 1 micromolar.

EXAMPLE 1

2-(4-(4-(3,4-Dichlorobenzamido)phenoxy)-3-((4-fluorophenylsulfonamido)methyl)-phenyl)acetic acid

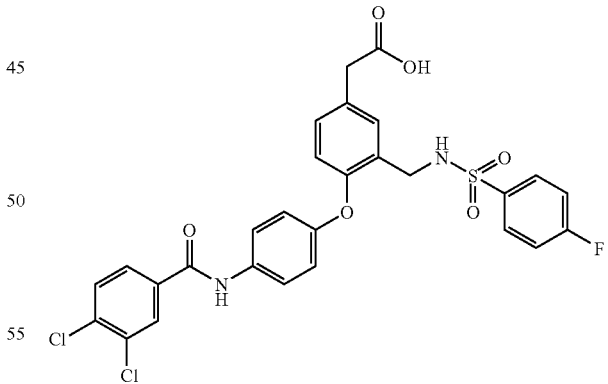

Step A: 2-(4-hydroxyphenyl)acetic acid (7.0 g, 46 mmol) was diluted with methane sulfonic acid (100 mL) and cooled to −10° C. 2-(Hydroxymethyl)isoindoline-1,3-dione (8.2 g, 46 mmol) was added portionwise over 15 minutes. The reaction was allowed to warm to room temperature and stirred overnight. The reaction was poured onto ice and stirred for 1 hour. The reaction mixture was filtered and rinsed with water. The material was air dried overnight and then placed under high vacuum for 5 hours. The material was then taken up in DMF using heat to ensure all the material was in solution. Small amounts of water were added until a precipitate persisted. The mixture was filtered and the solid material corresponded to bis alkylated material. Additional water was added to crash out the 2-(3-((1,3-dioxoisoindolin-2-yl)methyl)-4-hydroxyphenyl)acetic acid which was filtered and dried. This material was carried on to the next step without further purification.

Step B: The product of step A (6.7 g, 22 mmol) was diluted with HBr (21 g, 258 mmol) and acetic acid (20 mL). The reaction mixture was heated to reflux and stirred overnight. The reaction mixture was then cooled to 0° C. and was neutralized with solid NaOH pellets to pH~10, affording a solution of 2-(3-(aminomethyl)-4-hydroxyphenyl)acetic acid which was used in the next step without further purification.

Step C: To 2-(3-(aminomethyl)-4-hydroxyphenyl)acetic acid (3.9 g, 21.5 mmol) was added Boc$_2$O (5.40 g, 24.8 mmol) in 30 mL of dioxane. After stirring for 4 hours, the reaction was diluted with ethyl acetate and 1N HCl. The organic layer was dried over MgSO$_4$ and concentrated. The solid was taken up in minimal methylene chloride, filtered and rinsed with methylene chloride. The filtrate was concentrated to yield 3.0 g of 2-(3-((tert-butoxycarbonyl)aminomethyl)-4-hydroxyphenyl)acetic acid as a white foam.

Step D: 2-(3-((tert-Butoxycarbonyl)aminomethyl)-4-hydroxyphenyl)acetic acid (1.6 g, 5.69 mmol) was diluted with THF (10 mL) and methanol (5 mL) followed by the addition of TMSCHN$_2$ (14.2 mL, 28.4 mmol) dropwise. The reaction mixture was stirred for 30 minutes and then diluted with ethyl acetate and water. The layers were separated and the organic layer was dried over MgSO$_4$, filtered and concentrated. The material was purified using a biotage 40S cartridge eluting with hexanes:ethyl acetate (4:1) yield 860 mg of clear oil that later solidified to methyl 2-(3-((tert-butoxycarbonyl)aminomethyl)-4-hydroxyphenyl)acetate.

Step E: Methyl 2-(3-((tert-butoxycarbonyl)aminomethyl)-4-hydroxyphenyl)acetate (200 mg, 0.677 mmol) was diluted with ACN (2 mL) followed by the addition of K$_2$CO$_3$ (206 mg, 1.49 mmol) and 1-fluoro-4-nitrobenzene (0.103 mL, 0.948 mmol). The reaction mixture was heated to reflux (at about 82° C.) and stirred for 5 hours. The reaction mixture was then diluted with ethyl acetate and water. The layers were separated and the organic layer was dried over MgSO$_4$, filtered and concentrated. The material was purified using a biotage 40S eluting with hexanes/ethyl acetate (3:1) to yield 242 mg of methyl 2-(3-((tert-butoxycarbonyl)aminomethyl)-4-(4-nitrophenoxy)phenyl)acetate as a clear oil.

Step F: Methyl 2-(3-((tert-butoxycarbonyl)aminomethyl)-4-(4-nitrophenoxy)phenyl)acetate (242 mg, 0.581 mmol) was diluted with THF (3 mL) followed by the addition of Zn dust (38.0 mg, 0.581 mmol). About 2 mL of saturated ammonium chloride was added dropwise. After stirring the reaction for 10 minutes, the reaction mixture was diluted with ethyl acetate and saturated sodium bicarbonate. The layers were separated and the organic layer was dried over MgSO$_4$, filtered and concentrated to yield 225 mg of methyl 2-(4-(4-aminophenoxy)-3-((tert-butoxycarbonyl)aminomethyl)phenyl)acetate.

Step G: Methyl 2-(4-(4-aminophenoxy)-3-((tert-butoxycarbonyl)aminomethyl)phenyl)acetate (100 mg, 0.259 mmol) was diluted with methylene chloride (3 mL) followed by the addition of 3,4-dichlorobenzoyl chloride (81.3 mg, 0.388 mmol) and N,N-diisopropylethyl amine (0.0451 mL, 0.259 mmol). The reaction was stirred for 3 hours. The reaction mixture was diluted with methylene chloride and water. The layers were separated and the organic layer was dried over MgSO$_4$, filtered and concentrated. The material was purified using a biotage 12i eluting with hexanes:ethyl acetate (3:1) to yield 130 mg of methyl 2-(3-((tert-butoxycarbonyl)aminomethyl)-4-(4-(3,4-dichlorobenzamido)phenoxy)phenyl)acetate.

Step H: Methyl 2-(3-((tert-butoxycarbonyl)aminomethyl)-4-(4-(3,4-dichlorobenzamido)phenoxy)phenyl)acetate (130 mg, 0.232 mmol) was treated with HCl (0.581 mL, 2.32 mmol). After stirring for 3 hours, the material was concentrated to yield 100 mg of methyl 2-(3-(aminomethyl)-4-(4-(3,4-dichlorobenzamido)phenoxy)phenyl)acetate.

Step I: The product of step H (30 mg, 0.065 mmol) was diluted with methylene chloride (1 mL) followed by the addition of 4-fluorobenzene-1-sulfonyl chloride (15 mg, 0.078 mmol) and DIEA (0.024 mL, 0.14 mmol). After stirring the reaction for 4 hours, the reaction mixture was placed directly onto a preparative tlc plate 0.5 mm and eluted with hexanes: ethyl acetate (3:1) to yield 30 mg of methyl 2-(4-(4-(3,4-dichlorobenzamido)phenoxy)-3-((4-fluorophenyl-sulfonamido)methyl)phenyl)acetate.

Step J: Methyl 2-(4-(4-(3,4-dichlorobenzamido)phenoxy)-3-((4-fluorophenyl-sulfonamido)methyl)phenyl)acetate (40 mg, 0.065 mmol) was diluted with MeOH (1 mL) followed by the addition of NaOH (0.32 mL, 1.3 mmol). After stirring for 1 hour, the reaction mixture was diluted with ethyl acetate and 2N HCl. The layers were separated and the organic layer was dried over MgSO$_4$, filtered and concentrated. The material was purified using a 0.5 mm preparative plate eluting with methylene chloride:MeOH:AcOH (90:9:1) to yield 12 mg of the title compound as a solid. $^1$H NMR (400 MHz, CDCl$_3$/CD$_3$OD) 8.1 (m, 1H), 7.85 (m, 1H), 7.8 (m, 2H), 7.7 (d, 1H), 7.6 (d, 1H), 7.25 (s, 1H), 7.2 (m, 3H), 6.85 (d, 2H), 6.7 (d, 1H), 4.15 (s, 2H), 3.55 (s, 2H).

EXAMPLE 2

2-(4-(4-(3,4-Dichlorobenzamido)phenoxy)-3-(methylsulfonamidomethyl)phenyl)acetic acid

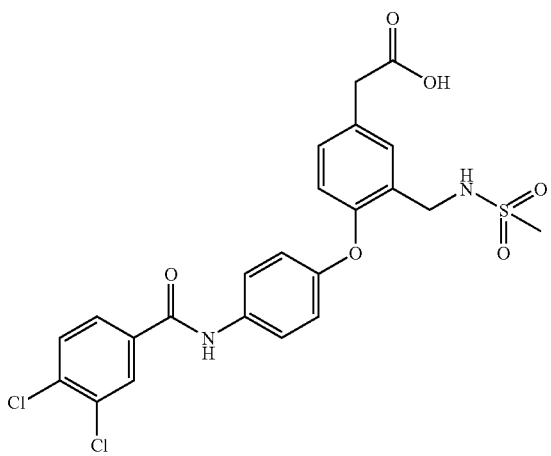

Prepared by the method of Example 1, substituting 4-fluorobenzene-1-sulfonyl chloride in Step H with methanesulfonyl chloride. $^1$H NMR (400 MHz, d$_6$-DMSO) 12.4 (s, 1H), 10.4 (s, 1H), 8.20 (m, 1H), 7.95 (m, 1H), 7.85 (d, 1H), 7.75 (d, 2H), 7.55 (t, 1H), 7.4 (m, 1H), 7.19 (m, 1H), 7.05 (d, 2H), 6.8 (d, 1H), 4.2 (d, 2H), 3.55 (s, 2H), 2.85 (s, 3H).

EXAMPLE 3

2-(4-(4-(3,4-Dichlorobenzamido)phenoxy)-3-((2,4-dichlorophenylsulfonamido)methyl)-phenyl)acetic acid

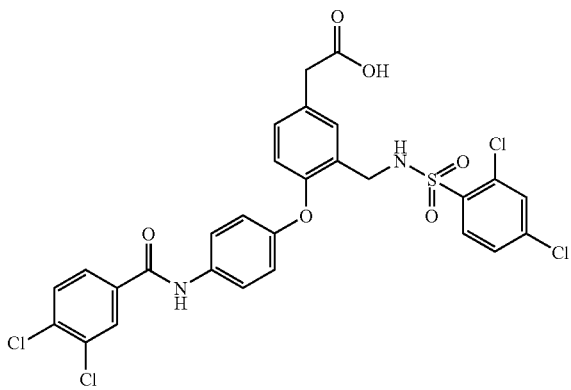

Prepared by the method of Example 1, substituting 4-fluorobenzene-1-sulfonyl chloride in Step H with 2,4-dichlorobenzyl-1-sulfonyl chloride. $^1$H NMR (400 MHz, CDCl$_3$/CD$_3$OD) 8.1 (s, 1H), 7.85 (m, 2H), 7.65 (m, 3H), 7.50 (m, 1H), 7.35 (d, 1H), 7.2 (s, 1H), 7.10 (d, 1H), 6.90 (d, 2H), 6.60 (d, 1H), 4.20 (s, 2H), 3.45 (s, 2H).

EXAMPLE 4

2-(4-(4-(3,4-Dichlorobenzamido)phenoxy)-3-(nicotinamidomethyl)phenyl)acetic acid

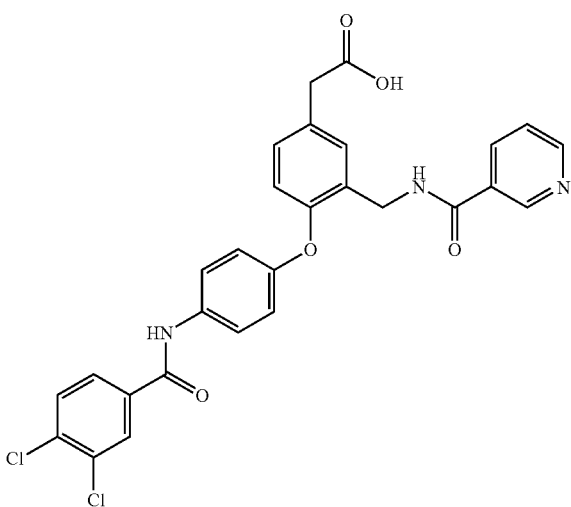

Step A: 4-Aminophenol (1.9 g, 17 mmol) was diluted with DMF (40 mL) followed by the addition of pyridine (0.978) (1.4 mL, 17 mmol) and 3,4-dichlorobenzoyl chloride (3.0 g, 14 mmol) in 5 mL of DMF. After stirring for 12 hours, the reaction mixture was diluted with ethyl acetate and 2N HCl. The aqueous layer was extracted once with ethyl acetate. The organics were combined, washed with water, brine, dried over MgSO$_4$, filtered and concentrated onto silica gel. The material was purified using a biotage 40M column eluting with hexanes:ethyl acetate (9:1) using 2 L and then (60:40) 1 L to yield 3,4-dichloro-N-(4-hydroxyphenyl)-benzamide (1.5 g, 37% yield) as a white solid.

Step B: tert-Butyl 2-(3-cyano-4-fluorophenyl)acetate (2.0 g, 8.5 mmol) and the product of step A (2.9 g, 10 mmol) were diluted with DMSO (22 mL) followed by the addition of potassium carbonate (1.4 g, 10 mmol). The reaction was heated to 125° C. and stirred for 12 hours. The reaction mixture was then cooled to room temperature, diluted with ethyl acetate and 10% aqueous sodium carbonate. The layers were separated and the organic layer was washed with 10% aqueous sodium carbonate two more times followed by water and brine. The organic material was dried over MgSO$_4$, filtered and concentrated. The material was purified using a biotage 40M column eluting with hexanes:ethyl acetate (8:2) to yield tert-butyl 2-(3-cyano-4-(4-(3,4-dichlorobenzamido)phenoxy)phenyl)acetate (2.5 g, 59% yield) as a white solid.

Step C: The product of step B (100 mg, 0.201 mmol) was diluted with 7N ammonia/methanol (10 mL), followed by addition of ethyl acetate (10 mL). Once the material dissolved, Raney Nickel (1.72 mg, 0.0201 mmol) was added and the reaction was purged three times with a balloon of hydrogen. After stirring for 12 hours, the reaction mixture was filtered through a GF/F filter and concentrated. The residue was purified using a biotage 12i column eluting with methylene chloride:MeOH:NH$_4$OH (90:9:1) to yield tert-butyl 2-(3-(aminomethyl)-4-(4-(3,4-dichlorobenzamido)phenoxy)phenyl)acetate (100 mg, 99.2% yield) as a clear oil.

Step D: The product of step C (0.050 g, 0.997 mmol) was dissolved into 1 mL of DCM in a small test tube. Pyridine (0.017 g, 0.219 mmol) and nicotinoyl chloride (0.0195 g, 0.110 mmol) were added, and the reaction mixture was stirred for 12 hours. The reaction mixture was then diluted with methylene chloride and water. The methylene chloride layer was separated and loaded directly onto a biotage 12i column eluting with methylene chloride:MeOH (95:5) to yield tert-butyl 2-(4-(4-(3,4-dichlorobenzamido)phenoxy)-3-(nicotinamidomethyl)phenyl)-acetate (44 mg, 73% yield) as a clear oil.

Step E: The product of step D (44 mg, 0.073 mmol) was diluted with methylene chloride:TFA (1:1) and stirred for 3 hours. The reaction mixture was concentrated, taken up in ether and sonicated. The solid was filtered, rinsed with ether and dried under vacuum to yield the title compound (35 mg, 88% yield) as white solid. $^1$H NMR (400 MHz, CDCl$_3$/CD$_3$OD) 8.75 (m, 1H), 8.65 (m, 1H), 8.15 (m, 1H), 8.10 (m, 1H), 8.0 (m, 1H), 7.60 (m, 3H), 7.45 (m, 1H), 7.20 (m, 1H), 6.95 (d, 2H), 6.90 (d, 1H), 4.65 (m, 2H), 3.62 (s, 2H).

EXAMPLE 5

2-(4-(4-(3,4-Dichlorobenzamido)phenoxy)-3-((N,N-dimethylsulfamoylamino)methyl)-phenyl)acetic acid

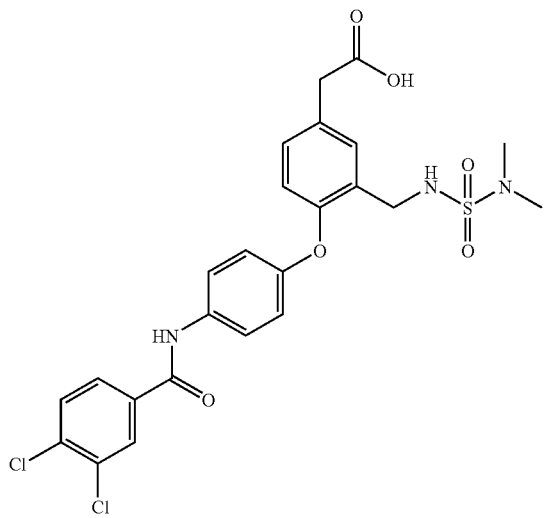

Prepared by the method of Example 4, substituting nicotinoyl chloride in Step D with dimethylsulfamoyl chloride. $^1$H NMR (400 MHz, CDCl$_3$/CD$_3$OD) 8.05 (s, 1H), 7.80 (m, 1H), 7.65 (m, 2H), 7.55 (d, 1H), 7.35 (m, 1H), 7.18 (m, 1H), 7.00 (d, 2H), 6.82 (d, 1H), 4.25 (s, 2H), 3.60 (s, 2H), 2.75 (s, 6H).

EXAMPLE 6

2-(4-(4-(3,4-Dichlorobenzamido)phenoxy)-3-(methylsulfonamidomethyl)phenyl)acetic acid

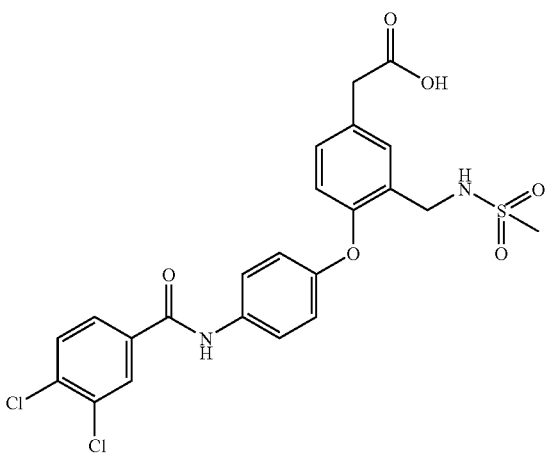

Prepared by the method of Example 4, substituting nicotinoyl chloride in Step D with methanesulfonyl chloride. $^1$H NMR (400 MHz, d$_6$-DMSO) 12.4 (s, 1H), 10.4 (s, 1H), 8.20 (m, 1H), 7.95 (m, 1H), 7.85 (d, 1H), 7.75 (d, 2H), 7.55 (t, 1H), 7.4 (m, 1H), 7.19 (m, 1H), 7.05 (d, 2H), 6.8 (d, 1H), 4.2 (d, 2H), 3.55 (s, 2H), 2.85 (s, 3H).

EXAMPLE 7

2-(3-(Cyclohexanecarboxamidomethyl)-4-(4-(3,4-dichlorobenzamido)phenoxy)phenyl)-acetic acid

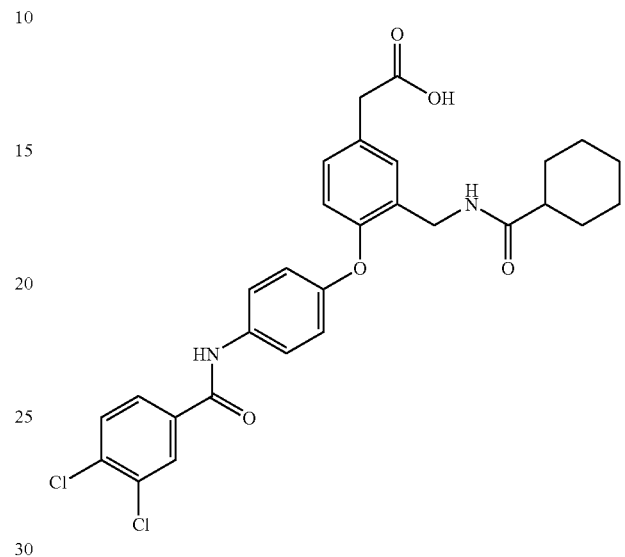

Prepared by method of Example 4, substituting nicotinoyl chloride in Step D with cyclohexanecarbonyl chloride. $^1$H NMR (400 MHz, CDCl$_3$/CD$_3$OD) 8.10 (m, 1H), 7.80 (m, 1H), 7.65 (d, 2H), 7.55 (d, 1H), 7.25 (m, 1H), 7.15 (d, 1H), 6.95 (d, 2H), 6.85 (d, 1H), 2.10 (m, 1H), 1.6-1.8 (m, 5H), 1.2-1.4 (m, 6H).

EXAMPLE 8

2-(3-(Acetamidomethyl)-4-(4-(3,4-dichlorobenzamido)phenoxy)phenyl)acetic acid

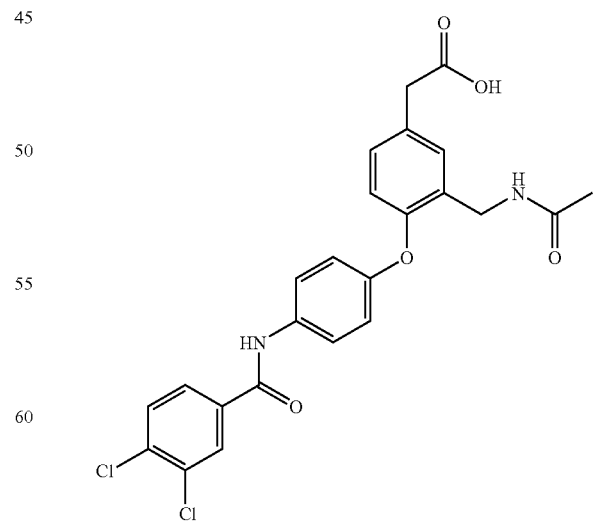

Prepared by the method of Example 4, substituting nicotinoyl chloride in Step D with acetyl chloride. $^1$H NMR (400

MHz, CDCl₃/CD₃OD) 8.10 (m, 1H), 7.80 (m, 1H), 7.60 (m, 3H), 7.30 (m, 1H), 7.15 (m. 1H), 6.95 (d, 2H), 6.85 (d, 1H), 4.42 (s, 2H), 3.40 (s, 2H), 1.95 (s, 3H).

EXAMPLE 9

2-(4-(4-(3,4-Dichlorobenzamido)phenoxy)-3-(isonicotinamidomethyl)phenyl)acetic acid

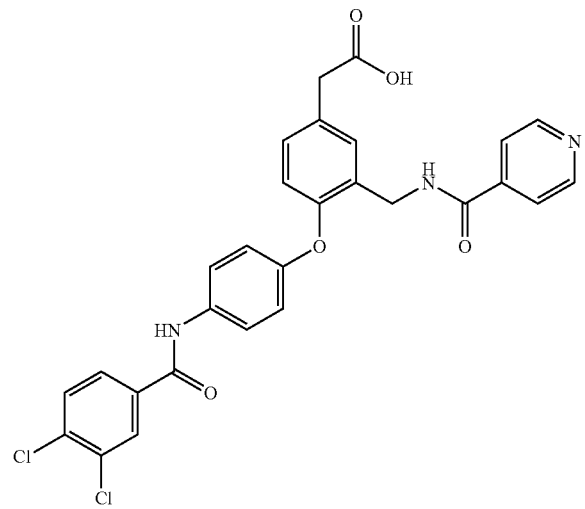

Prepared by the method of Example 4, substituting nicotinoyl chloride in Step D with isonicotinoyl chloride. ¹H NMR (400 MHz, CDCl₃/CD₃OD) 8.62 (m, 1H), 8.05 (m, 1H), 7.88 (m, 1H), 7.80 (m, 1H), 7.65 (m, 2H), 7.58 (m, 3H), 7.35 (m, 1H), 7.20 (m, 1H), 6.95 (d, 2H), 6.90 (d, 1H), 4.65 (d, 2H), 3.62 (s, 2H).

EXAMPLE 10

2-(4-(4-(3,4-Dichlorobenzamido)phenoxy)-3-((4-fluorobenzamido)methyl)phenyl)acetic acid

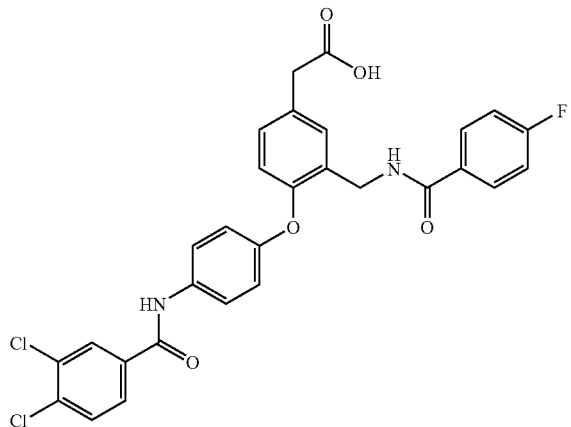

Prepared by the method of Example 4, substituting nicotinoyl chloride in Step D with 4-fluorobenzoyl chloride. ¹H NMR (400 MHz, CD₃OD) 8.10 (s, 1H), 7.85 (m, 1H), 7.80 (m, 2H), 7.70 (d, 1H), 7.62 (d, 2H), 7.35 (s, 1H), 7.25 (d, 1H), 7.35 (m, 2H), 6.95 (d, 2H), 6.90 (d, 1H), 4.62 (s, 2H), 3.60 (s, 3H).

EXAMPLE 11

2-(4-(4-(3,4-Dichlorobenzamido)phenoxy)-3-(picolinamidomethyl)phenyl)acetic acid

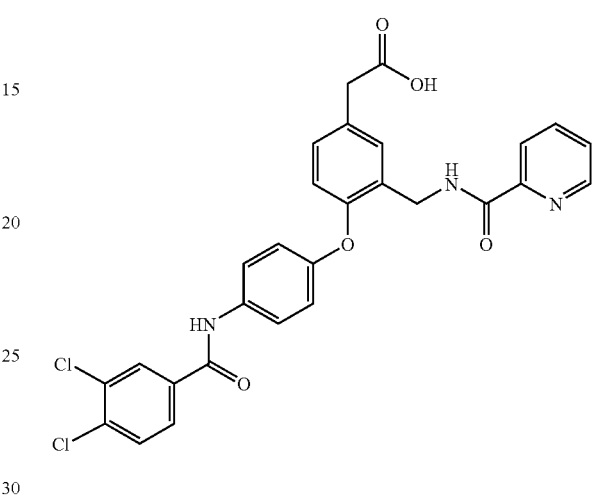

Prepared by the method of Example 4, substituting nicotinoyl chloride in Step D with picolinoyl chloride. ¹H NMR (400 MHz, CD₃OD) 8.60 (d, 1H), 8.10 (m, 1H), 8.05 (m, 1H), 7.95 (m, 1H), 7.85 (m, 1H), 7.70 (d, 1H), 7.60 (d, 2H), 7.55 (m, 1H), 7.35 (m, 1H), 7.20 (d, 1H), 7.00 (d, 2H), 6.85 (d, 1H), 4.64 (s, 2H), 3.60 (s, 2H).

EXAMPLE 12

2-(4-(4-(3,4-Dichlorobenzamido)phenoxy)-3-((methoxycarbonylamino)methyl)phenyl)-acetic acid

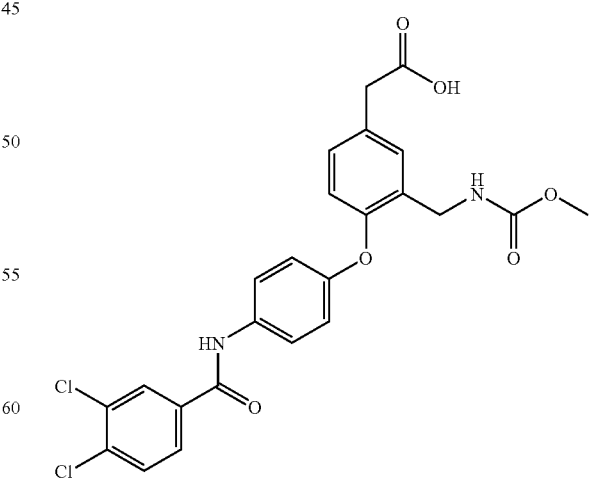

Prepared by the method of Example 4, substituting nicotinoyl chloride in Step D with methyl chloroformate. ¹H NMR (400 MHz, CDCl₃) 8.10 (m, 1H), 7.80 (m, 1H), 7.65 (m, 2H), 7.58 (m, 1H), 7.30 (m, 1H), 7.19 (m, 1H), 6.95 (m, 2H), 6.85 (m, 1H), 4.40 (s, 2H), 3.65 (s, 3H), 3.60 (s, 2H).

EXAMPLE 13

2-(4-(4-(3,4-Dichlorobenzamido)phenoxy)-3-((pyridine-3-sulfonamido)methyl)phenyl)-acetic acid

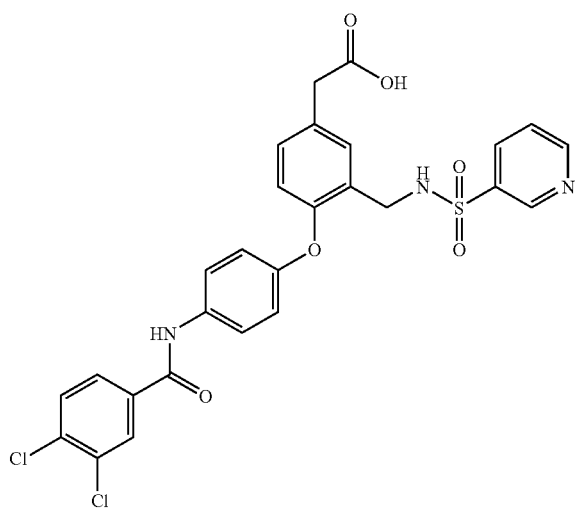

Prepared by the method of Example 4, substituting nicotinoyl chloride in Step D with pyridine-3-sulfonyl chloride. $^1$H NMR (400 MHz, CDCl$_3$) 8.95 (s, 1H), 8.60 (m, 1H), 8.10 (m, 1H), 8.05 (d, 1H), 7.80 (d, 1H), 7.60 (m, 3H), 7.35 (m, 1H), 7.22 (m, 1H), 7.05 (d, 1H), 6.80 (d, 2H), 6.62 (d, 1H), 4.25 (s, 1H), 3.55 (s, 2H).

EXAMPLE 14

2-(4-(4-(3,4-Dichlorophenylcarbamoyl)phenoxy)-3-(methylsulfonamidomethyl)phenyl)-acetic acid

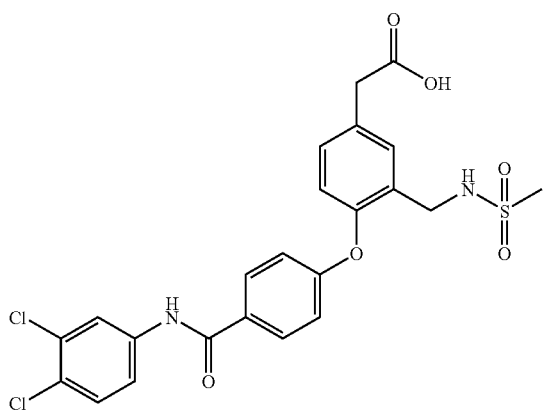

Step A: tert-Butyl 2-(3-cyano-4-fluorophenyl)acetate (2.6 g, 11.1 mmol) and methyl 4-hydroxybenzoate (3.36 g, 22.1 mmol) were diluted with DMSO (22 mL) followed by the addition of potassium carbonate (1.83 g, 13.3 mmol). The reaction mixture was heated to 125° C. and stirred for 5 hours. The reaction mixture was diluted with ethyl acetate and 10% aqueous sodium carbonate. The layers were separated and the organic layer was washed with 10% aqueous sodium carbonate two more times followed by water and brine. The organic material was dried over MgSO$_4$, filtered and concentrated. The material was purified using a biotage 40M column eluting with hexanes:ethyl acetate (9:1) to yield methyl 4-(4-(2-tert-butoxy-2-oxoethyl)-2-cyanophenoxy)benzoate (2.65 g, 65.3% yield) as a clear oil.

Step B: The product of step A (2.5 g, 6.80 mmol) was diluted with 7N ammonia/methanol (30 mL) followed by the addition of Raney Nickel (0.0583 g, 0.680 mmol). The reaction mixture was purged three times with hydrogen and stirred for 12 hours. The reaction mixture was then filtered through a GF/F filter and concentrated. The residue was purified using a biotage 40M column eluting with methylene chloride:MeOH:NH$_4$OH (90:9:1) to yield methyl 4-(2-(aminomethyl)-4-(2-tert-butoxy-2-oxoethyl)phenoxy)benzoate (1.87 g, 74.0% yield) as a clear oil.

Step C: The product of step B (1.87 g, 5.03 mmol) was diluted with methylene chloride (2 mL) followed by the addition of pyridine (0.489 mL, 6.04 mmol) and methanesulfonyl chloride (0.779 mL, 10.1 mmol). After stirring for 12 hours, the reaction mixture was diluted with methylene chloride and 2N HCl, the layers were separated and the organic layer was dried over MgSO$_4$, filtered and concentrated. The material was purified using a biotage 40M cartridge eluting with hexanes:ethyl acetate (1:1) to yield methyl 4-(4-(2-tert-butoxy-2-oxoethyl)-2-(methylsulfonamidomethyl)phenoxy)benzoate (1.53 g, 67.6% yield) as a clear oil.

Step D: The product of step C (900 mg, 2.00 mmol) was diluted with dioxane (10 mL) followed by the addition of LiOH—H$_2$O (126 mg, 3.00 mmol) dissolved in water (2 mL). After stirring for 12 hours, the reaction mixture was diluted with ethyl acetate and 2N HCl. The layers were separated and the organic layer was dried over MgSO$_4$, filtered and concentrated. The material was purified using a biotage 40M cartridge eluting with methylene chloride:MeOH (95:5) to yield 4-(4-(2-tert-butoxy-2-oxoethyl)-2-(methylsulfonamido-methyl)phenoxy)benzoic acid (710 mg, 81.4% yield) as a clear oil.

Step E: The product of step D (62 mg, 0.14 mmol) was diluted with methylene chloride (1 mL) followed by the addition of oxalyl dichloride (0.093 mL, 0.19 mmol) and 1 drop of DMF. The reaction was stirred for 30 minutes followed by the addition of 3,4-dichlorobenzenamine (46 mg, 0.28 mmol). The reaction was allowed to stir for 1 hour. The reaction mixture was loaded directly onto a 12i sim and purified on the horizon eluting with methylene chloride:MeOH (99.5-0.5 to 95:5) to yield 30 mg of tert-butyl 2-(4-(4-((3,4-dichlorophenyl)carbamoyl)phenoxy)-3-(methylsulfonamidomethyl) phenyl)acetate as a clear oil.

Step F: The product of step E (22 mg, 0.038 mmol) was diluted with methylene chloride (1 mL) followed by the addition of TFA (1 mL). After stirring for 1 hour, the reaction was concentrated, diluted with ether, sonicated and concentrated to yield 2-(4-(4-((3,4-dichlorophenyl)carbamoyl)phenoxy)-3-(methylsulfonamidomethyl)phenyl)acetic acid (15 mg, 75% yield) as a white solid. $^1$H NMR (400 MHz, CDCl$_3$/

CD$_3$OD) 7.92 (m, 1H), 7.90 (d, 2H), 7.59 (m, 1H), 7.42 (m, 2H), 7.25 (m, 1H), 7.10 (d, 2H), 6.90 (d, 1H), 4.28 (s, 2H), 3.62 (s, 2H), 2.85 (s, 3H).

EXAMPLE 15

2-(4-(4-(3,4-Dichlorophenethylcarbamoyl)phenoxy)-3-(methylsulfonamidomethyl)-phenyl)acetic acid

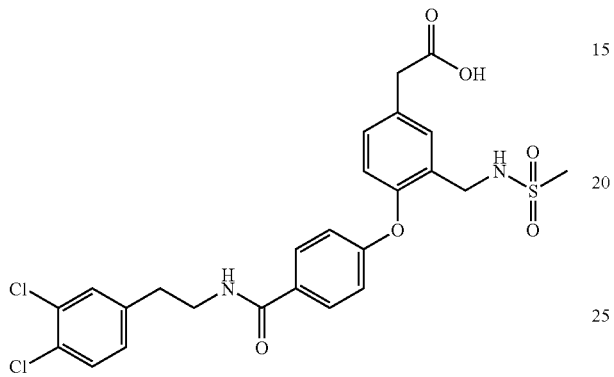

Prepared by the method of Example 14, substituting 3,4-dichlorobenzenamine in Step E with 2-(3,4-dichlorophenyl)ethanamine. $^1$H NMR (400 MHz, CDCl$_3$/CD$_3$OD) 7.75 (d, 2H), 7.35 (m, 3H), 7.22 (d, 1H), 7.10 (d, 1H), 6.95 (d, 2H), 6.90 (d, 1H), 4.25 (s, 2H), 3.62 (m, 4H), 3.40 (s, 2H), 2.90 (t, 2H), 2.85 (s, 3H).

EXAMPLE 16

2-(3-(Methylsulfonamidomethyl)-4-(4-(naphthalen-2-ylcarbamoyl)phenoxy)phenyl)-acetic acid

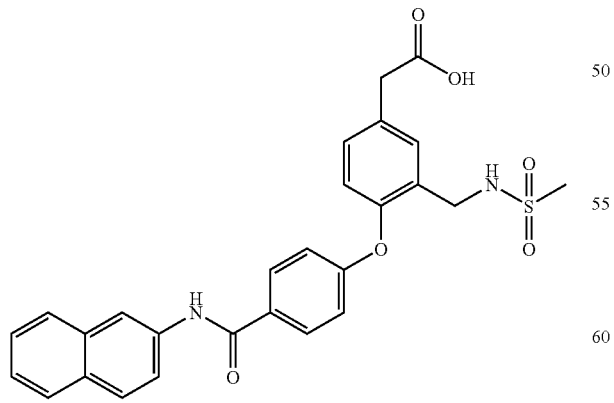

Prepared by the method of Example 14, substituting 3,4-dichlorobenzenamine in Step E with napthalen-2-amine. $^1$H NMR (400 MHz, CDCl$_3$/CD$_3$OD) 8.35 (s, 1H), 7.96 (d, 2H), 7.83 (m, 3H), 7.70 (d, 1H), 7.45 (m, 3H), 7.25 (d, 1H), 7.05 (d, 2H), 6.95 (d, 1H), 4.30 (d, 2H), 3.62 (s, 2H), 2.85 (s, 3H).

EXAMPLE 17

2-(4-(4-(4-Fluorophenethylcarbamoyl)phenoxy)-3-(methylsulfonamidomethyl)phenyl)-acetic acid

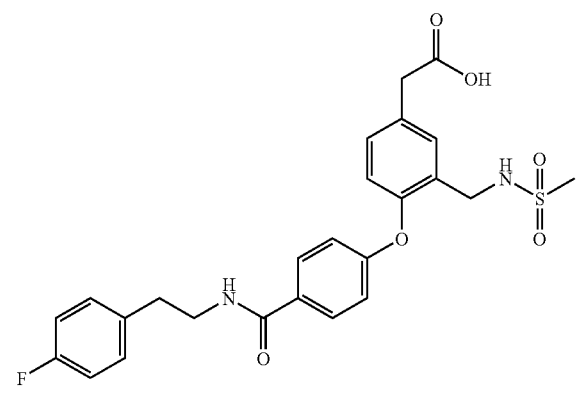

Prepared by the method of Example 14, substituting 3,4-dichlorobenzenamine in Step E with 2-(4-fluorophenyl)ethanamine. $^1$H NMR (400 MHz, CDCl$_3$/CD$_3$OD) 7.70 (d, 2H), 7.40 (m, 1H), 7.22 (m, 3H), 7.10 (m, 2H), 6.90 (d, 2H), 6.70 (d, 1H), 4.30 (s, 2H), 3.65 (m, 4H), 2.90 (t, 2H), 2.85 (s, 3H).

EXAMPLE 18

2-(3-(Methylsulfonamidomethyl)-4-(4-(phenethylcarbamoyl)phenoxy)phenyl)acetic acid

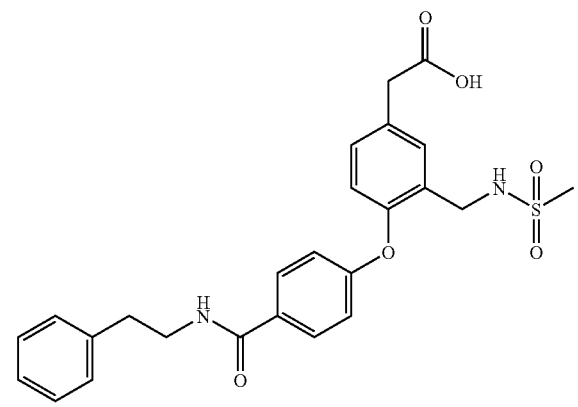

Prepared by the method of Example 14, substituting 3,4-dichlorobenzenamine in Step E with phenethylamine. $^1$H NMR (400 MHz, CDCl$_3$/CD$_3$OD) 7.70 (d, 2H), 7.40 (m, 1H), 7.31 (m, 1H), 7.25 (m, 5H), 6.95 (d, 2H), 6.90 (d, 1H), 4.30 (s, 2H), 3.68 (t, 2H), 3.61 (s, 2H), 2.90 (t, 2H), 2.85 (s, 3H).

EXAMPLE 19

2-(3-(Methylsulfonamidomethyl)-4-(4-(phenylcarbamoyl)phenoxy)phenyl)acetic acid

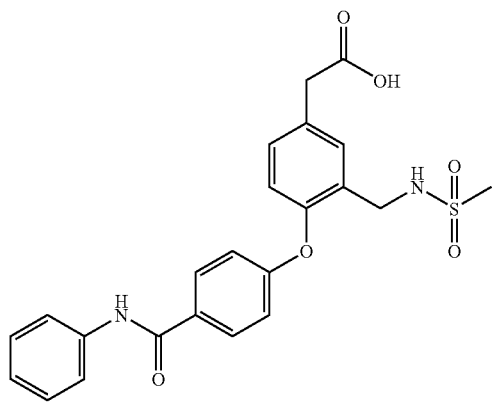

Prepared by the method of Example 14, substituting 3,4-dichlorobenzenamine in Step E with aniline. $^1$H NMR (400 MHz, CDCl$_3$/CD$_3$OD) 7.92 (d, 2H), 7.65 (d, 2H), 7.45 (s, 1H), 7.38 (m, 2H), 7.25 (d, 1H), 7.18 (m, 1H), 7.05 (d, 2H), 6.95 (d, 1H), 4.30 (s, 2H), 3.65 (s, 2H), 2.85 (s, 3H).

EXAMPLE 20

2-(4-(4-(Benzylcarbamoyl)phenoxy)-3-(methylsulfonamidomethyl)phenyl)acetic acid

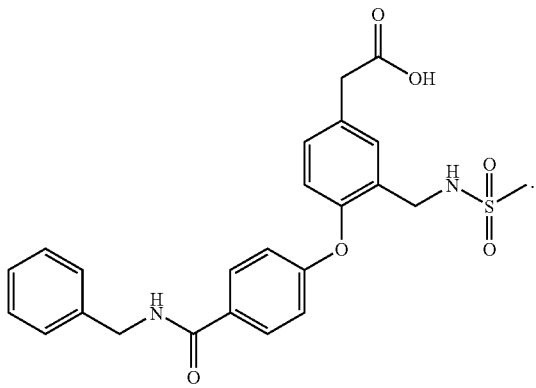

Prepared by the method of Example 14, substituting 3,4-dichlorobenzenamine in Step E with benzyl amine. $^1$H NMR (400 MHz, CDCl$_3$/CD$_3$OD) 7.80 (d, 2H), 7.40 (m, 1H), 7.35

(m, 4H), 7.22 (d, 1H), 6.95 (m, 3H), 6.90 (d, 1H), 4.62 (d, 2H), 4.30 (s, 2H), 3.62 (s, 2H), 2.85 (s, 3H).

EXAMPLE 21

2-(4-(4-(4-Chlorophenethylcarbamoyl)phenoxy)-3-(methylsulfonamidomethyl)phenyl)-acetic acid

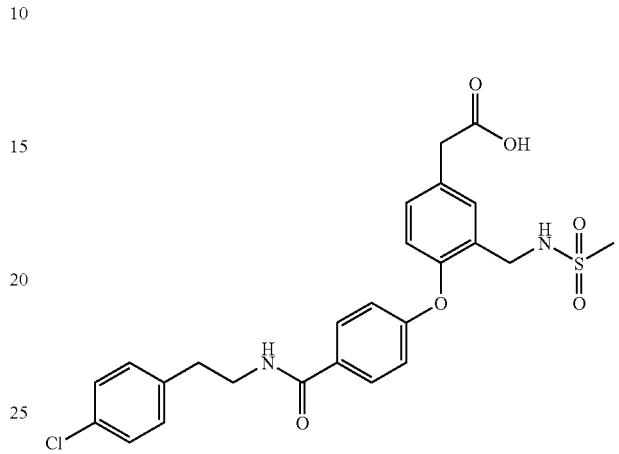

Prepared by the method of Example 14, substituting 3,4-dichlorobenzenamine in Step E with 2-(4-chlorophenyl)ethanamine. $^1$H NMR (400 MHz, CDCl$_3$/CD$_3$OD) 7.7 (d, 2H), 7.4 (s, 1H), 7.25 (d, 2H), 7.22 (d, 1H), 7.18 (d, 2H), 6.95 (d, 2H), 6.90 (d, 1H), 6.82 (br t, 1H), 4.3 (s, 2H), 3.65 (t, 2H), 3.4 (br s, 2H), 2.9 (t, 2H), 2.85 (s, 3H).

EXAMPLE 22

2-(4-(4-(2-(4-Chlorobenzylamino)-2-oxoethyl)phenoxy)-3-(methylsulfonamidomethyl)-phenyl)acetic acid

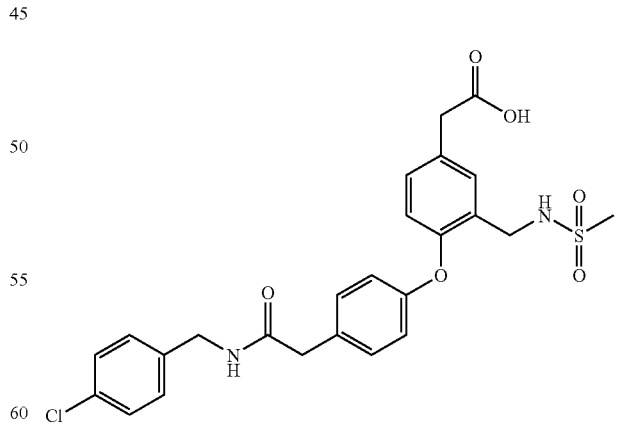

Prepared by the method of Example 14, substituting methyl 4-hydroxybenzoate in Step A with methyl 2-(4-hydroxyphenyl)acetate and substituting 3,4-dichlorobenzenamine in Step E with 4-chlorobenzyl amine. $^1$H NMR (400 MHz, CDCl$_3$/CD$_3$OD) 7.38 (m, 1H), 7.25 (m, 4H), 7.20 (m, 3H), 6.95 (d, 2H), 6.85 (d, 1H), 4.38 (m, 2H), 4.32 (s, 2H), 3.61 (s, 2H), 3.55 (s, 2H), 2.85 (s, 3H).

EXAMPLE 23

2-(4-(4-(2-(Benzylamino)-2-oxoethyl)phenoxy)-3-(methylsulfonamidomethyl)phenyl)-acetic acid

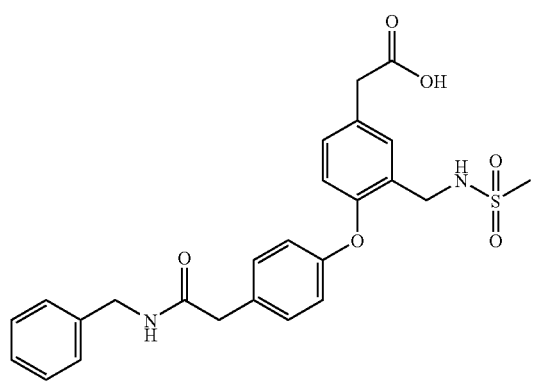

Prepared by the method of Example 14, substituting methyl 4-hydroxybenzoate in Step A with methyl 2-(4-hydroxylphenyl)acetate and substituting 3,4-dichlorobenzenamine in Step E with benzylamine. $^1$H NMR (400 MHz, CDCl$_3$/CD$_3$OD) 7.38 (m, 1H), 7.15-7.30 (m, 8H), 6.95 (d, 2H), 6.85 (d, 1H), 4.40 (d, 2H), 4.32 (s, 2H), 3.61 (s, 2H), 3.56 (s, 2H), 2.82 (s, 3H).

EXAMPLE 24

2-(3-(Methylsulfonamidomethyl)-4-(4-(2-oxo-2-(phenethylamino)ethyl)phenoxy)phenyl)-acetic acid

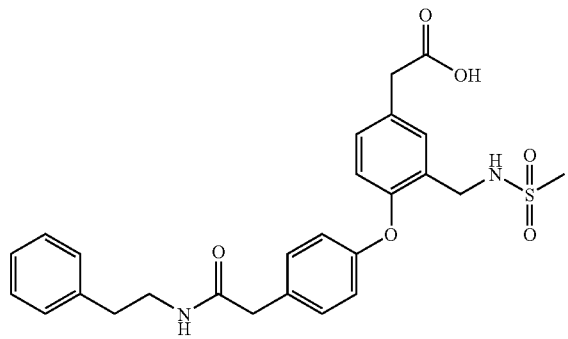

Prepared by the method of Example 14, substituting methyl 4-hydroxybenzoate in Step A with methyl 2-(4-hydroxylphenyl)acetate and substituting 3,4-dichlorobenzenamine in Step E with phenethylamine. $^1$H NMR (400 MHz, CDCl$_3$/CD$_3$OD) 7.38 (m, 1H), 7.28 (m, 1H), 7.25 (m, 1H), 7.18-7.22 (m, 2H), 7.15 (d, 2H), 7.10 (d, 1H), 6.92 (d, 2H), 6.82 (d, 1H), 4.38 (s, 2H), 3.62 (s, 2H), 3.48 (m, 4H), 2.82 (s, 3H), 2.75 (t, 2H).

EXAMPLE 25

2-(4-(4-(2-(Benzyl(methyl)amino)-2-oxoethyl)phenoxy)-3-(methylsulfonamidomethyl)-phenyl)acetic acid

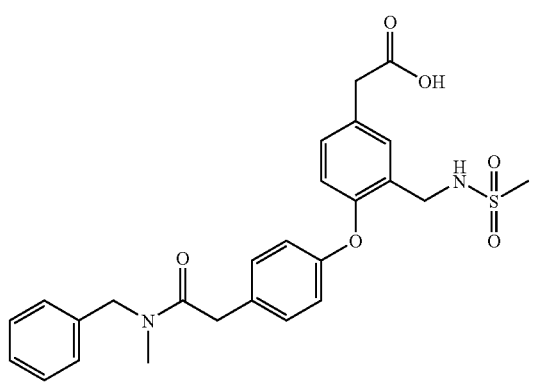

Prepared by the method of Example 14, substituting methyl 4-hydroxybenzoate in Step A with methyl 2-(4-hydroxylphenyl)acetate and substituting 3,4-dichlorobenzenamine in Step E with N-methylbenzylamine. $^1$H NMR (400 MHz, CDCl$_3$/CD$_3$OD) 7.10-7.40 (m, 9H), 6.94 (m, 2H), 6.82 (m, 1H), 4.60 (d, 2H), 4.35 (m, 2H), 3.75 (d, 2H), 3.62 (m, 2H), 2.97 (d, 3H), 2.82 (s, 3H).

EXAMPLE 26

2-(3-(Methylsulfonamidomethyl)-4-(4-(2-oxo-2-(phenylamino)ethyl)phenoxy)phenyl)-acetic acid

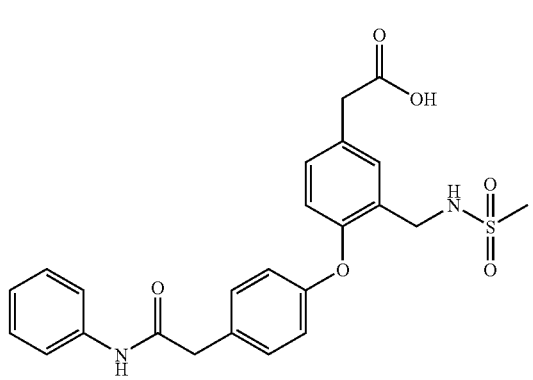

Prepared by the method of Example 14, substituting methyl 4-hydroxybenzoate in Step A with methyl 2-(4-hydroxylphenyl)acetate and substituting 3,4-dichlorobenzenamine in Step E with aniline. NMR (400 MHz, CDCl$_3$/

CD₃OD) 7.55 (d, 2H), 7.30-7.35 (m, 5H), 7.18 (m, 1H), 7.10 (m, 1H), 6.95 (d, 2H), 6.85 (d, 1H), 4.35 (s, 2H), 3.68 (s, 2H), 3.60 (s, 2H), 2.85 (s, 3H).

EXAMPLE 27

2-(4-(4-Benzamidophenoxy)-3-((4-fluorophenylsulfonamido)methyl)phenyl)acetic acid

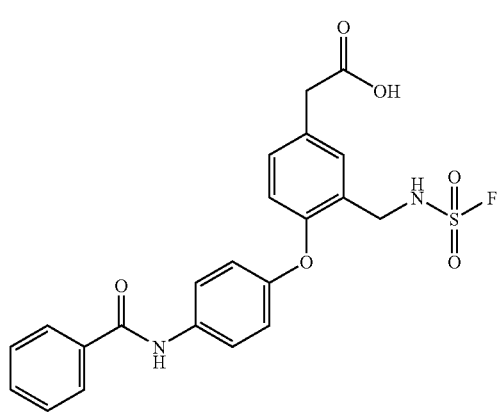

Prepared by the method of Example 1 substituting 3,4-dichlorobenzoyl chloride in Step G with benzoyl chloride. MS+534.9 [M+1].

EXAMPLE 28

2-(4-(4-(4-Chlorobenzamido)phenoxy)-3-((4-fluorophenylsulfonamido)methyl)phenyl)-acetic acid

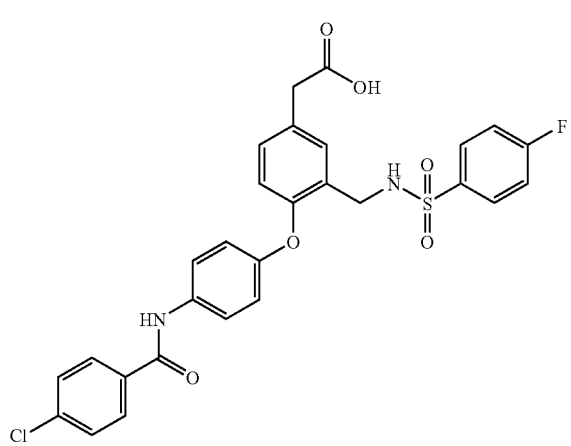

Prepared by the method of Example 1 substituting 3,4-dichlorobenzoyl chloride in Step G with 4-chlorobenzoyl chloride. ¹H NMR (400 MHz, CD₃OD) 7.85 (d, 2H), 7.70 (m, 1H), 7.45-7.55 (m, 5H), 7.35 (m, 1H), 7.15 (m, 2H), 6.60-6.70 (m, 3H), 4.55 (s, 2H), 3.58 (s, 2H).

EXAMPLE 29

2-(4-(4-(3-Chlorobenzamido)phenoxy)-3-((4-fluorophenylsulfonamido)methyl)phenyl)-acetic acid

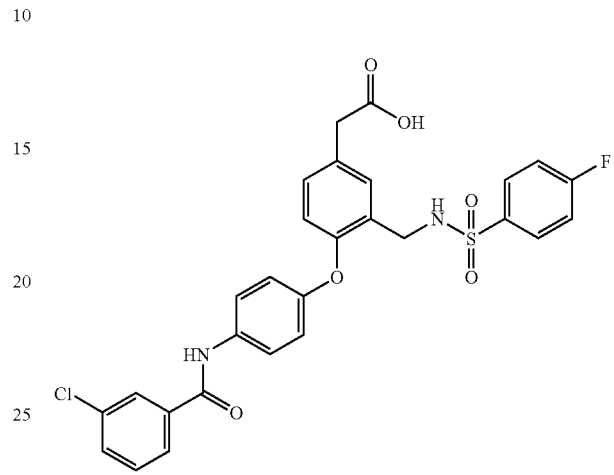

Prepared by the method of Example 1 substituting 3,4-dichlorobenzoyl chloride in Step G with 3-chlorobenzoyl chloride ¹H NMR (400 MHz, CD₃OD) 7.90 (s, 1H), 7.80 (d, 1H), 7.65 (m, 1H), 7.52 (m, 4H), 7.45 (t, 1H), 7.35 (m, 1H), 7.15 (m, 2H), 6.60 (m, 4H), 4.45 (s, 2H), 3.50 (br s, 2H).

EXAMPLE 30

2-(4-(4-(3,4-Difluorobenzamido)phenoxy)-3-(methylsulfonamidomethyl)phenyl)acetic acid

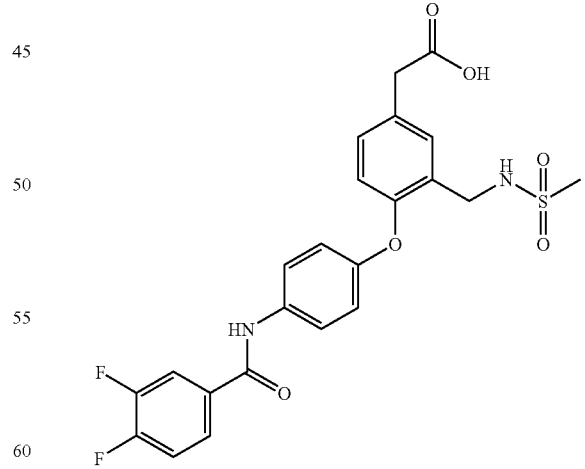

Prepared by the method of Example 1 substituting 3,4-dichlorobenzoyl chloride in Step G with 3,4-difluorobenzoyl chloride and substituting 4-fluorobenzene-1-sulfonyl chloride in Step 1 with methanesulfonyl chloride. ¹H NMR (400 MHz, CD₃OD) 7.88 (m 1H), 7.80 (m, 1H), 7.65 (d, 2H), 7.42

(m, 2H), 7.20 (m, 2H), 7.00 (d, 2H), 6.82 (m, 1H), 4.33 (s, 2H), 3.62 (s, 2H), 2.85 (s, 3H).

EXAMPLE 31

2-(4-(4-(2-Chlorobenzamido)phenoxy)-3-(methyl-sulfonamidomethyl)phenyl)acetic acid

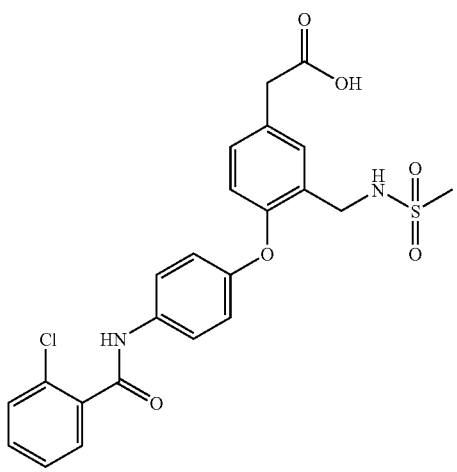

Prepared by the method of Example 1 substituting 3,4-dichlorobenzoyl chloride in Step G with 2-chlorobenzoyl chloride and substituting 4-fluorobenzene-1-sulfonyl chloride in Step I with methanesulfonyl chloride. $^1$H NMR (400 MHz, CD$_3$OD) 7.68 (d, 2H), 7.40-7.55 (m, 5H), 7.20 (d, 1H), 7.05 (d, 2H), 6.85 (d, 1H), 4.35 (s, 2H), 3.65 (br s, 2H), 2.85 (s, 3H).

EXAMPLE 32

2-(4-(4-(3,4-Dichlorobenzamido)phenoxy)-3-methoxyphenyl)acetic acid

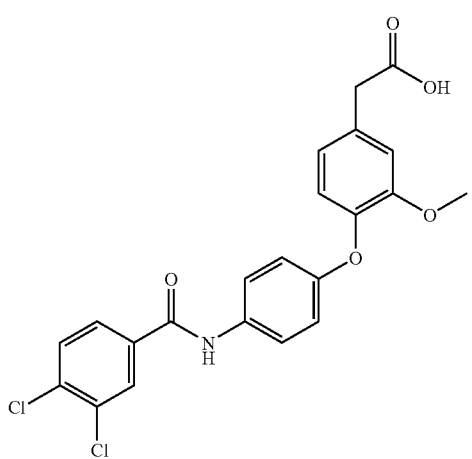

Prepared according to Steps E, F, G and J of Example, 1, substituting methyl 2-(3-((tert-butoxycarbonyl)aminomethyl)-4-hydroxyphenyl)acetate in Step E with methyl 2-(4-hydroxy-3-methoxyphenyl)acetate. $^1$H NMR (400 MHz, CDCl$_3$) 9.64 (s, 1H), 8.17 (d, 1H), 7.97 (dd, 1H), 7.72-7.75 (m, 4H), 7.13 (d, 1H), 6.99 (d, 1H), 6.93 (d, 1H), 6.87 (m, 2H), 3.80 (s, 3H), 3.66 (s, 2H).

EXAMPLE 33

2-(4-(4-(benzyloxycarbamoyl)phenoxy)-3-(methyl-sulfonamidomethyl)phenyl)acetic acid

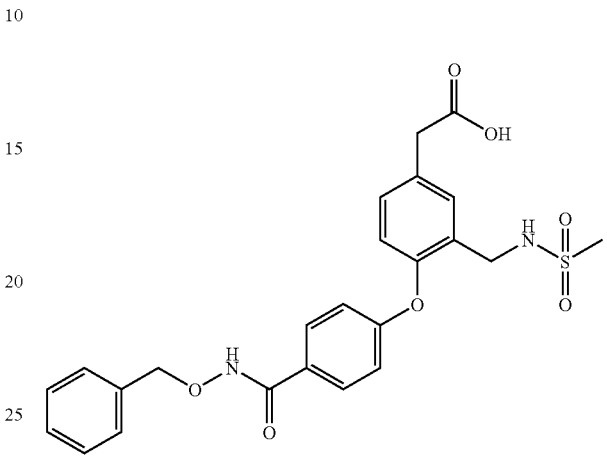

Prepared by the method of Example 14, substituting 3,4-dichlorobenzenamine in Step E with O-benzylhydroxy-lamine hydrochloride. $^1$H NMR (400 MHz, CD$_3$OD) 7.76 (d, J=8.6 Hz, 2H), 7.50 (t, J=6.3 Hz, 1H), 7.33-7.48 (m, 5H), 7.23 (d, J=6.3 Hz, 1H), 6.99 (d, J=8.7 Hz, 2H), 6.91 (d, J=8.4 Hz, 2H), 4.91 (s, 2H), 4.10 (d, J=6.3 Hz, 2H), 3.60 (s, 2H), 2.85 (s, 3H).

EXAMPLE 34

2-(3-Chloro-4-(4-(4-chlorophenethylcarbamoyl)phenoxy)phenyl)acetic acid

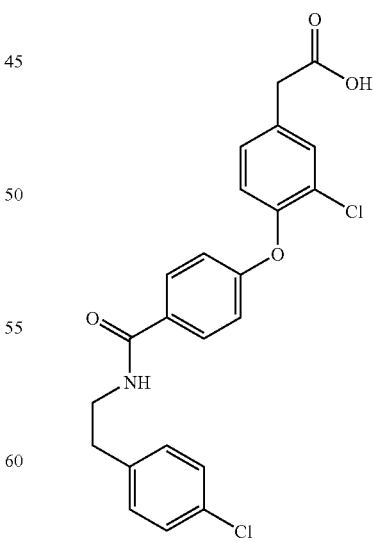

Step A: 2-(3-Chloro-4-hydroxyphenyl)acetic acid (5.0 g, 26.8 mmol) was dissolved in 30 mL of MeOH and H$_2$SO$_4$ (0.744 ml, 13.4 mmol) was added dropwise at ambient temperature. The reaction was refluxed for four hours and then concentrated in vacuo. The residue was diluted with 150 mL of EtOAc and washed sequentially with saturated NaHCO$_3$, water, and brine, dried over H$_2$SO$_4$, and concentrated in vacuo to provide methyl 2-(3-chloro-4-hydroxyphenyl)acetate (5.16 g, 96.0% yield) as a semi-opaque thick oil.

Step B: Methyl 2-(3-chloro-4-hydroxyphenyl)acetate (177 mg, 0.885 mmol) was diluted with DMSO (3 mL) followed by the addition of K$_2$CO$_3$ (122 mg, 0.885 mmol) and N-(4-chlorophenethyl)-4-chloro-3-nitrobenzamide (300 mg, 0.885 mmol) (synthesized in step C). The reaction was heated to 85° C. and stirred for 12 hours. The reaction was cooled, diluted with DCM and washed with 10% aq. sodium carbonate, water and brine. The layers were separated and the organic layer was dried over H$_2$SO$_4$, filtered and concentrated. The material was purified using a biotage 40S cartridge eluting with DCM:MeOH (99:1) to yield methyl 2-(4-(4-((4-chlorophenethyl)carbamoyl)-2-nitrophenoxy)-3-chlorophenyl)acetate (206 mg, 46.3% yield).

Step C: 2-(4-Chlorophenyl)ethanamine (2.3 ml, 16 mmol) was diluted with DCM (40 mL) followed by the addition of DIEA (2.9 ml, 16 mmol) and 4-chloro-3-nitrobenzoyl chloride (3.0 g, 14 mmol) in 10 mL of DCM. After stirring for 30 minutes the reaction was loaded directly onto a biotage 40M cartridge and eluted with hexanes:ethyl acetate (2:1) to yield N-(4-chlorophenethyl)-4-chloro-3-nitrobenzamide (4.0 g, 86% yield) as a white solid.

Step D: Methyl 2-(4-(4-((4-chlorophenethyl)carbamoyl)-2-nitrophenoxy)-3-chlorophenyl)acetate (110 mg, 0.219 mmol) was diluted with THF (1 mL) followed by the addition of Zn dust (14.3 mg, 0.219 mmol) and saturated NH$_4$Cl (1 mL). After stirring for 1 hour, the reaction was diluted DCM and 10% aq. sodium carbonate. The layers were separated and the organic layer was dried over MgSO$_4$, filtered and concentrated to yield methyl 2-(4-(4-((4-chlorophenethyl)carbamoyl)-2-aminophenoxy)-3-chlorophenyl)acetate (102 mg, 98.6% yield).

Step E: Isobutyl nitrite (0.0751 ml, 0.634 mmol) was diluted with DMF (1 mL), placed under nitrogen and heated to 60° C. Methyl 2-(4-(4-((4-chlorophenethyl)carbamoyl)-2-aminophenoxy)-3-chlorophenyl)acetate (100 mg, 0.211 mmol) in DMF (1 mL) was added dropwise and the reaction was stirred for 1 hour. The reaction was cooled, diluted with ethyl acetate and washed with 2N HCl, saturated sodium bicarbonate and brine. The organic layer was dried over MgSO$_4$, filtered and concentrated. The material was purified using a biotage 12i column, eluting with DCM:MeOH (99:1) to yield methyl 2-(4-(4-((4-chlorophenethyl)carbamoyl)phenoxy)-3-chlorophenyl)acetate (70 mg, 72.3% yield).

Step F: Methyl 2-(4-(4-((4-chlorophenethyl)carbamoyl) phenoxy)-3-chlorophenyl)acetate (33 mg, 0.0720 mmol) was diluted with THF (500 µL) followed by the addition NaOH (0.144 ml, 0.720 mmol) and 100 µL of water. After stirring for 2 hours, the reaction was diluted with DCM and 2N HCl. The layers were separated and the organic layer was dried over MgSO$_4$, filtered and concentrated to yield 2-(4-(4-((4-chlorophenethyl)carbamoyl)phenoxy)-3-chlorophenyl)acetic acid (19 mg, 59.4% yield) as a white solid. $^1$H NMR (400 MHz, CDCl$_3$/CD$_3$OD) δ 7.65 (d, 2H), 7.42 (m, 1H), 7.25 (d, 2H), 7.20 (d, 1H), 7.15 (d, 2H), 7.05 (d, 1H), 6.85 (d, 2H), 3.65 (1, 2H), 3.60 (s, 2H), 2.90 (t, 2H).

EXAMPLE 35

2-(3-cyano-4-(4-(3,4-dichlorobenzamido)phenoxy) phenyl)propanoic acid

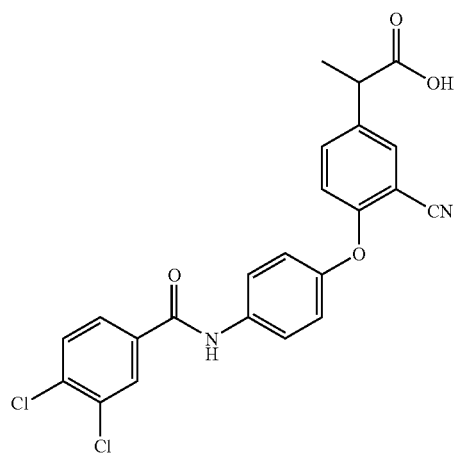

Step A: To a stirred solution of diisopropylamine (357 µl, 2.55 mmol) in THF (3 ml) at −78° C. was added n-butyllithium (2.5M in hexanes, 1.02 ml, 2.55 mmol). The reaction was stirred for 30 minutes after which time a solution of the acetate (500 mg, 2.13 mmol) in THF (3.5 ml) was added dropwise and stirred for 20 minutes at −78° C., then warmed to 0° C. MeI (133 µl, 2.13 mmol) was added and the reaction stirred for an additional 30 minutes. The reaction was acidified with 2M HCl and extracted with EtOAc. The combined organics were then washed with brine and dried over MgSO$_4$. The residue was purified on the Biotage Horizon (40+M, 5% to 50% B:EtOAc, 21 ml-1008 ml) to give tert-butyl 2-(3-cyano-4-fluorophenyl)propanoate (0.368 g, 1.48 mmol, 70%). $^1$H NMR (400 MHz, CDCl$_3$) δ 7.50-7.60 (m, 2H), 7.17 (t, J=8.7 Hz, 1H), 3.63 (q, J=7.1 Hz, 1H), 4.60 (d, J=7.2H; 3H), 1.40 (s, 9H).

Step B: To a stirred solution of 4-aminophenol (2.50 g, 22.9 mmol) in DMF (55 ml) was added pyridine (1.85 ml, 22.9 mmol) followed by 3,4-dichlorobenzoyl chloride (4.0 g, 19.1 mmol) in DMF (7 ml). The reaction stirred at ambient temperature overnight, then diluted with 2M HCl and EtOAc. The aqueous layer was then extracted with EtOAc and the combined organics washed with brine and dried over MgSO$_4$. The residue was purified on the Biotage Horizon (65+M 5% to 75% B:EtOAc, 51 ml-2448 ml). 3,4-Dichloro-N-(4-hydroxyphenyl)benzamide was collected as a white solid (3.91 g, 13.9 mmol, 73%). $^1$H NMR (400 MHz, CD$_3$OD) δ 8.09 (s, 1H), 7.84 (d, J=8.5 Hz, 1H), 7.67 (d, J=8.6 Hz, 1H), 7.45 (d, J=8.8 Hz, 2H), 6.78 (d, J=8.4 Hz, 2H).

Step C: To a stirred solution of tert-butyl 2-(3-cyano-4-fluorophenyl)propanoate (360 mg, 1.44 mmol) from Step A and 3,4-dichloro-N-(4-hydroxyphenyl)benzamide (488 mg, 1.73 mmol) from Step B in DMSO (4 ml) was added K$_2$CO$_3$ (240 mg, 1.73 mmol). The reaction was stirred 125° C. overnight, then cooled to ambient temperature and diluted with EtOAc and 10% aqueous sodium carbonate. The aqueous phase was extracted with EtOAc and the combined organics washed with 10% aqueous sodium carbonate and brine, dried over MgSO₄, concentrated and purified on a Biotage Horizon (40+M 5% to 50% B:EtOAc, 21 ml-1008 ml). The appropriate fractions were then combined and concentrated to give tert-butyl 2-(3-cyano-4-(4-(3,4-dichlorobenzamido)phenoxy)phenyl)propanoate (0.476 g, 0.797 mmol, 55%). ¹H NMR (400 MHz, CDCl₃) δ 7.99 (s, 1H), 7.84 (bs, N—H), 7.72 (d, J=9.3 Hz, 1H), 7.67 (d, J=8.7 Hz, 2H), 7.60 (m, 2H), 7.42 (d, J=8.6 Hz, 1H), 7.11 (d, J=7.7, 2H), 6.83 (d, J=8.7 Hz, 1H), 3.61 (q, J=7.1 Hz, 1H), 1.45 (d, J=7.5 Hz, 3H), 1.42 (s, 9H).

Step D: To a stirred solution of tert-butyl 2-(3-cyano-4-(4-(3,4-dichlorobenzamido)phenoxy)phenyl)propanoate (25 mg, 0.049 mmol) in DCM (1 ml) was added TFA (250 μl). The reaction was stirred at ambient temperature for 4 hours and then concentrated. The crude product was purified via preparative TLC (5% MeOH/DCM) to give 2-(3-cyano-4-(4-(3,4-dichlorobenzamido)phenoxy)phenyl)propanoic acid (0.0174 g, 0.0382 mmol, 78%). ¹H NMR (400 MHz, CDCl₃): 8.04 (bs, N—H), 7.96 (s, 1H), 7.64-7.71 (m, 3H), 7.61 (s, 1H), 7.55 (d, J=7.7 Hz, 1H), 7.44 (dd, J=8.6, 2.2H; 1H), 7.08 (d, J=8.9 Hz, 2H), 6.83 (d, J=8.5 Hz, 1H), 3.74 (q, J=7.4 Hz, 1H), 1.53 (d, J=6.9 Hz, 3H).

EXAMPLE 36

2-(4-(4-(3,4-dichlorobenzamido)phenoxy)-3-(methylsulfonamidomethyl)phenyl)propanoic acid

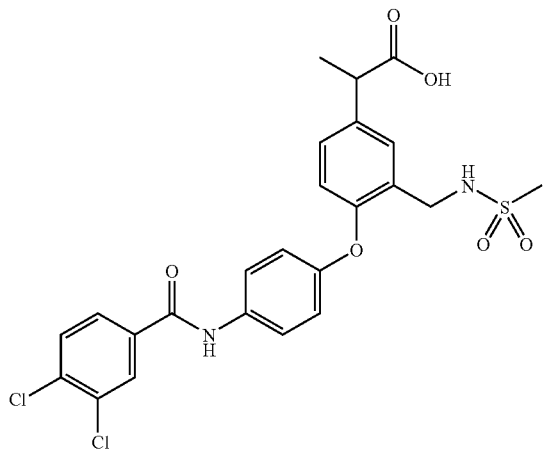

Prepared by the method of Example 14 substituting methyl 4-(4-(2-tert-butoxy-2-oxoethyl)-2-cyanophenoxy)benzoate in Step B with tert-butyl 2-(3-cyano-4-(4-(3,4-dichlorobenzamido)phenoxy)phenyl)propanoate and following steps C and F. ¹H NMR (400 MHz, CD₃OD): 8.10 (s, 1H), 7.85 (s, 1H), 7.60-7.70 (m, 3H), 7.50 (s, 1H), 7.20 (d, 1H), 7.1 (d, 2H), 6.80 (d, 1H), 4.30 (s, 2H), 3.75 (q, 1H), 2.80 (2, 3H), 1.45 (d, 3H).

EXAMPLE 37

2-(4-(4-(3,4-dichlorobenzamido)phenoxy)-3-(methylsulfonamidomethyl)phenyl)-2-methylpropanoic acid

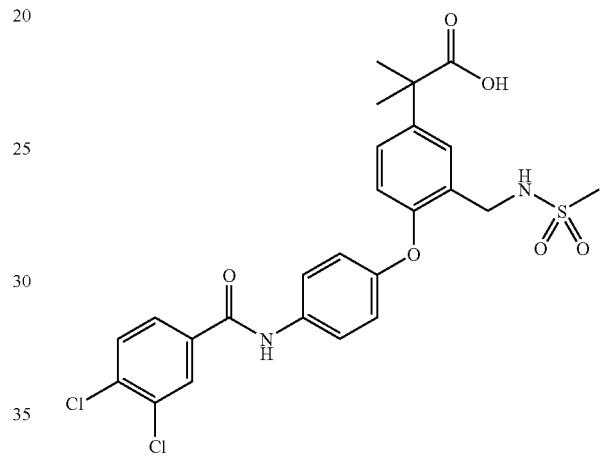

Step A: To a stirred solution of NaH (60% in oil, 195 mg, 4.88 mmol) in DMF (10 ml) at 0° C. was added a solution of tert-butyl 2-(3-cyano-4-fluorophenyl)acetate (500 mg, 2.125 mmol) and MeI (330 μl, 5.31 mmol) in DMF (1 ml) dropwise. The reaction was warmed to ambient temperature, stirred overnight, and then diluted with 1N HCl and EtOAc. The aqueous was extracted with EtOAc and the combined organics washed with brine and dried over MgSO₄. The crude concentrated product was then purified on the Biotage Horizon (40+M 5% to 50% B:EtOAc, 18 ml-864 ml) to give tert-butyl 2-(3-cyano-4-fluorophenyl)-2-methylpropanoate (0.423 g, 1.602 mmol, 75%). ¹H NMR (400 MHz, CDCl₃) δ 7.56-7.63 (m, 2H), 7.17 (t, J=8.1 Hz, 1H), 1.54 (s, 6H), 1.38 (s, 9H).

Step B: 2-(4-(4-(3,4-Dichlorobenzamido)phenoxy)-3-(methylsulfonamidomethyl)phenyl)-2-methylpropanoic acid was prepared from tert-butyl 2-(3-cyano-4-fluorophenyl)-2-methylpropanoate by the method of Example 35 substituting tert-butyl 2-(3-cyano-4-fluorophenyl)propanoate in Step B with tert-butyl 2-(3-cyano-4-fluorophenyl)-2-methylpropanoate and following steps B, C and F of Example 14. ¹H NMR (400 MHz, CD₃OD): 8.15 (s, 1H), 7.85 (d, 1H), 7.65-

7.75 (m, 3H), 7.55 (s, 1H), 7.30 (d, 1H), 7.05 (d, 2H), 6.80 (d, 1H), 4.35 (s, 2H), 2.80 (s, 3H), 1.55 (s, 6H).

EXAMPLE 38

2-(3-(Methylsulfonamidomethyl)-4-(4-(4-(trifluoromethyl)phenylcarbamoyl)phenoxy)phenyl)acetic acid

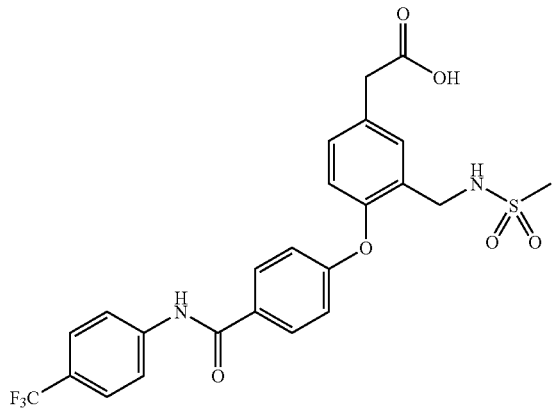

Prepared by the method of Example 14, substituting 3,4-dichlorobenzenamine in Step E with 4-trifluoromethylbenzenamine. $^1$H NMR (400 MHz, CD$_3$Cl$_3$, CD$_3$OD) 7.95 (d, 2H), 7.82 (d, 2H), 7.62 (d, 1H), 7.45 (s, 1H), 7.25 (d, 1H), 7.05 (d, 2H), 6.95 (d, 1H), 4.30 (s, 2H), 3.62 (s, 2H), 2.82 (s, 3H).

EXAMPLE 39

2-(3-(Methylsulfonamidomethyl)-4-(4-(3-(trifluoromethyl)phenylcarbamoyl)phenoxy)phenyl)acetic acid

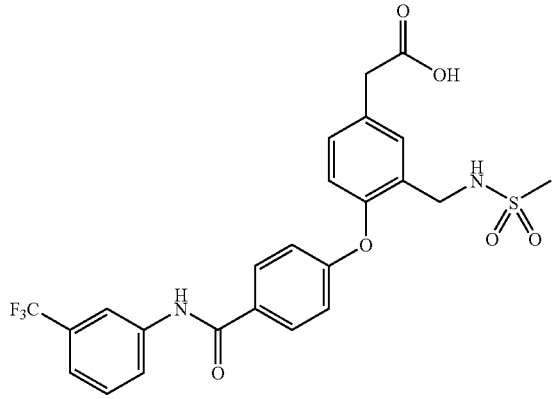

Prepared by the method of Example 14, substituting 3,4-dichlorobenzenamine in Step E with 3-trifluoromethylbenzenamine. $^1$H NMR (400 MHz, CD$_3$Cl$_3$, CD$_3$OD) 8.05 (s, 1H),
7.90 (m, 3H), 7.50 (m, 1H), 7.45 (s, 1H), 7.40 (m, 1H), 7.25 (d, 1H), 7.05 (d, 2H), 6.85 (d, 1H), 4.30 (s, 2H), 3.65 (s, 2H), 2.85 (s, 3H).

EXAMPLE 40

2-(4-(4-(4-chloro-3-fluorophenylcarbamoyl)phenoxy)-3-(methylsulfonamidomethyl)phenyl)acetic acid

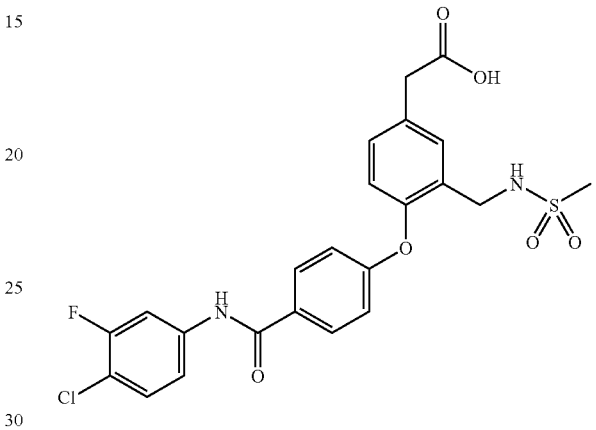

Prepared by the method of Example 14, substituting 3,4-dichlorobenzenamine in Step E with 4-chloro-3-fluorobenzenamine. $^1$H NMR (400 MHz, CD$_3$Cl$_3$, CD$_3$OD) 7.90 (d, 2H), 7.75 (m, 1H), 7.30-7.45 (m, 3H), 7.25 (d, 1H), 7.05 (d, 2H), 6.95 (d, 1H), 4.3 (s, 2H), 3.65 (s, 2H), 2.85 (s, 3H).

EXAMPLE 41

2-(4-(4-(3-chloro-4-fluorophenylcarbamoyl)phenoxy)-3-(methylsulfonamidomethyl)phenyl)acetic acid

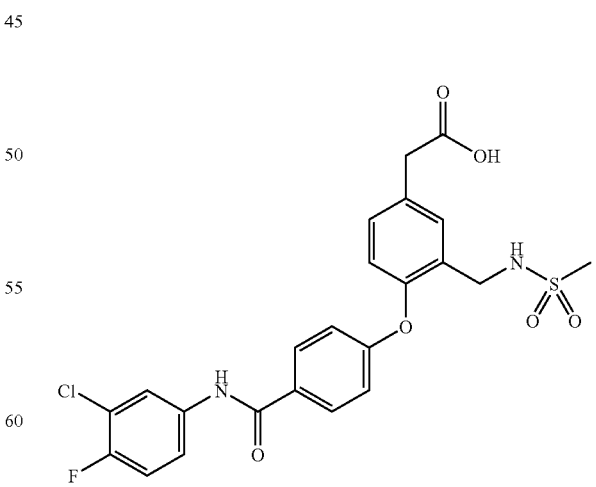

Prepared by the method of Example 14, substituting 3,4-dichlorobenzenamine in Step E with 3-chloro-4-fluorobenzenamine. $^1$H NMR (400 MHz, CD$_3$Cl$_3$, CD$_3$OD) 7.93 (d, 2H), 7.85 (m, 1H), 7.55 (m, 1H), 7.45 (s, 1H), 7.25 (d, 1H), 7.15 (t, 1H), 7.05 (d, 2H), 6.85 (d, 1H), 4.30 (s, 2H), 3.65 (s, 2H), 2.85 (s, 3H).

EXAMPLE 42

2-(4-(4-(4-chlorophenethylcarbamoyl)phenoxy)phenyl)acetic acid

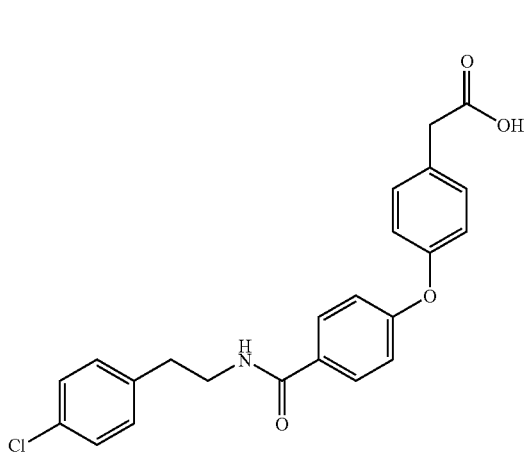

Step A: 2-(4-hydroxyphenyl)acetic acid (1.0 g, 6.57 mmol) was diluted with THF (4 mL) followed by the addition of Reactant 2 (2.63 g, 13.1 mmol). The reaction was stirred for hours 12 hours. The reaction was filtered and loaded directly onto a biotage 40M cartridge eluting with hexanes:ethyl acetate (3:1) to yield tert-butyl 2-(4-hydroxyphenyl)acetate (800 mg, 58.4% yield) as a clear oil that later solidified to a white solid.

Step B: 2-(4-chlorophenyl)ethanamine (0.321 ml, 2.27 mmol) was diluted with DCM (10 mL) followed by the addition of DIEA (d 0.742) (0.395 ml, 2.27 mmol) and 4-fluorobenzoyl chloride (0.231 ml, 1.89 mmol). After stirring for 30 minutes the reaction was loaded directly onto a biotage 40S cartridge and eluted with hexanes:ethyl acetate (2:1) to yield N-(4-chlorophenethyl)-4-fluorobenzamide (393 mg, 74.8% yield) as a white solid.

Step C: Tert-butyl 2-(4-hydroxyphenyl)acetate (200 mg, 0.960 mmol) was diluted with DMSO (4 mL) followed by the addition of $K_2CO_3$ (133 mg, 0.960 mmol) and N-(4-chlorophenethyl)-4-fluorobenzamide (267 mg, 0.960 mmol). The reaction was stirred at 85° C. overnight, and then stirred at 138° C. for 12 hours. The reaction was cooled to ambient temperature, diluted with DCM and 10% aq. sodium carbonate. The layers were separated and the organic layer was dried over $MgSO_4$, filtered and concentrated. The crude material was purified by silica gel chromatography, eluting with hexanes:ethyl acetate (4:1) to yield tert-butyl 2-(4-(4-((4-chlorophenethyl)carbamoyl)phenoxy)phenyl)acetate (20 mg, 4.47% yield) as an off white solid.

Step D: Tert-butyl 2-(4-(4-((4-chlorophenethyl)carbamoyl)phenoxy)phenyl)acetate (20 mg, 0.043 mmol) was diluted with DCM (1 mL) followed by the addition of TFA (1 mL). After stirring for 2 hours, the reaction was concentrated, diluted with ether and concentrated to yield 2-(4-(4-((4-chlorophenethyl)carbamoyl)phenoxy)phenyl)acetic acid (17 mg, 97% yield) as a white solid. $^1$H NMR (400 MHz, $CD_3Cl_3$, $CD_3OD$) 7.70 (d, 2H), 7.30 (m, 4H), 7.19 (m, 2H), 7.00 (m, 4H), 3.62 (m, 4H), 2.90 (t, 2H).

EXAMPLE 43

2-(4-(4-(4-chlorophenethylcarbamoyl)phenoxy)-3-fluorophenyl)acetic acid

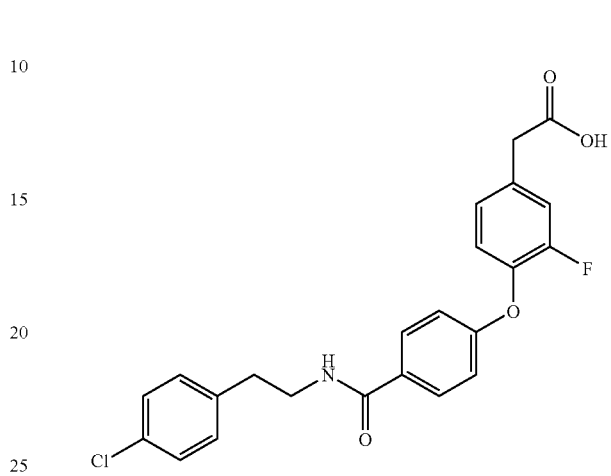

Step A: 2-(3-Fluoro-4-hydroxyphenyl)acetic acid (1.0 g, 5.88 mmol) was diluted with THF:MeOH (3:1) (10 mL) followed by the addition of $TMSCHN_2$ (5.88 ml, 11.8 mmol). After stirring for 1 hour, the reaction was quenched with 2N HCl and diluted with DCM. The layers were separated and the organic layer was dried over $MgSO_4$, filtered and concentrated. The material was purified by silica gel chromatography, eluting with hexanes:ethyl acetate (2:1) to yield methyl 2-(3-fluoro-4-hydroxyphenyl)acetate (700 mg, 64.7% yield) as a clear oil.

Step B: 2-(4-Chlorophenyl)ethanamine (2.3 ml, 16 mmol) was diluted with DCM (40 mL) followed by the addition of DIEA (2.9 ml, 16 mmol) and 4-chloro-3-nitrobenzoyl chloride (3.0 g, 14 mmol) dropwise in 10 mL of DCM. After stirring for 30 minutes the reaction was loaded directly onto a silica gel column and eluted with hexanes:ethyl acetate (2:1) to yield N-(4-chlorophenethyl)-4-chloro-3-nitrobenzamide (4.0 g, 86% yield) as a white solid.

Step C: Methyl 2-(3-fluoro-4-hydroxyphenyl)acetate (prepared in Step A; 163 mg, 0.885 mmol) was diluted with DMSO (3 mL) followed by the addition of $K_2CO_3$ (122 mg, 0.885 mmol) and N-(4-chlorophenethyl)-4-chloro-3-nitrobenzamide (prepared in Step B; 300 mg, 0.885 mmol). The reaction was stirred at 80° C. for 12 hours. The reaction was cooled, diluted with DCM and washed with 10% aq. sodium carbonate, water and brine. The layers were separated and the organic layer was dried over $MgSO_4$, filtered and concentrated. The material was purified by silica gel chromatography, eluting with hexane:acetone (2:1) to yield methyl 2-(4-(4-((4-chlorophenethyl)carbamoyl)-2-nitrophenoxy)-3-fluorophenyl)acetate (200 mg, 46.4% yield).

Step D: Methyl 2-(4-(4-((4-chlorophenethyl)carbamoyl)-2-nitrophenoxy)-3-fluorophenyl)acetate (100 mg, 0.205 mmol) was diluted with THF (2 mL) followed by the addition of Zn dust (13.4 mg, 0.205 mmol) and saturated aq. NH4Cl (1 mL). After stirring for 1 hour, the reaction was diluted with ethyl acetate and 10% aq sodium carbonate. The layers were separated and the organic layer was dried over $MgSO_4$, filtered and concentrated to yield methyl 2-(4-(4-((4-chlorophenethyl)carbamoyl)-2-aminophenoxy)-3-fluorophenyl)acetate (93 mg, 99.1% yield).

Step E: Isobutyl nitrile (0.060 ml, 0.51 mmol) was diluted with DMF (2 mL), placed under nitrogen and heated to 60° C. followed by the addition of methyl 2-(4-(4-((4-chlorophenethyl)carbamoyl)-2-aminophenoxy)-3-fluorophenyl)acetate (93 mg, 0.20 mmol) in 500 μL of DMF. The reaction was stirred 30 minutes and then cooled. The reaction was diluted with ethyl acetate and washed with 2N HCl and saturated sodium bicarbonate. The layers were separated and the organic layer was dried over $MgSO_4$, filtered and concentrated. The material was purified by silica gel chromatography, eluting with hexanes:ethyl acetate (2:1) to yield methyl 2-(4-(4-((4-chlorophenethyl)carbamoyl)phenoxy)-3-fluorophenyl)acetate (35 mg, 39% yield).

Step F: Methyl 2-(4-(4-((4-chlorophenethyl)carbamoyl)phenoxy)-3-fluorophenyl)acetate (32 mg, 0.072 mmol) was diluted with dioxane (1 mL) followed by the addition of NaOH (0.072 ml, 0.36 mmol) and 200 μL of water. After stirring for 3 hours, the reaction was diluted with ethyl acetate and 2N HCl. The organic layer was dried over $MgSO_4$, filtered and concentrated to yield 2-(4-(4-((4-chlorophenethyl)carbamoyl)phenoxy)-3-fluorophenyl)acetic acid (15 mg, 48% yield) as a white solid. $^1$H NMR (400 MHz, $CD_3Cl_3$, $CD_3OD$) 7.70 (d, 2H), 7.25 (d, 2H), 7.19 (m, 3H), 7.10 (m, 2H), 6.95 (d, 2H), 3.65 (m, 4H), 2.90 (t, 2H).

EXAMPLE 44

2-(3-cyano-4-(4-(4-chlorophenethylcarbamoyl)phenoxy)phenyl)acetic acid

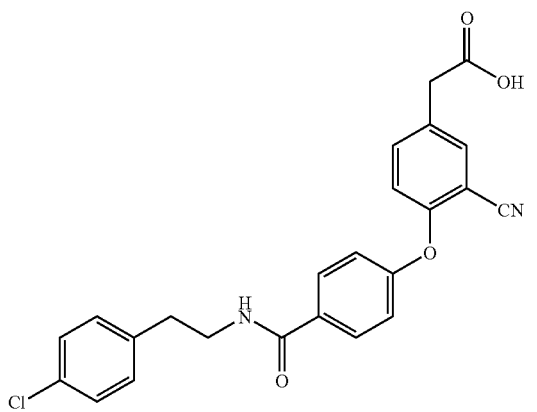

Step A: A flask was charged with tert-butyl 2-(3-cyano-4-fluorophenyl)acetate (9.410 g, 40.00 mmol), methyl 4-hydroxybenzoate (7.303 g, 48.00 mmol), $K_2CO_3$ (6.634 g, 48.00 mmol), and DMSO (160 mL). The mixture was heated to 90° C. under a nitrogen atmosphere for 17 hours. The mixture was cooled to ambient temperature and poured into a mixture of EtOAc (250 mL) and 10% $K_2CO_3$ solution (250 mL). The resulting insoluble residue was dissolved in water and added to the EtOAc-aqueous mixture. The mixture was stirred for 1 hour and layers were separated. The aqueous layer was extracted with EtOAc, and the combined extracts were washed with saturated $K_2CO_3$, water, and brine, dried over $MgSO_4$, filtered through a Celite pad, and concentrated under reduced pressure to give 14.7 g of crude product as an oil. The crude material was purified by silica gel chromatography to provide methyl 4-(4-(2-tert-butoxy-2-oxoethyl)-2-cyanophenoxy)benzoate (11.6 g, 79%) as a white solid.

Step B: Methyl 4-(4-(2-tert-butoxy-2-oxoethyl)-2-cyanophenoxy)benzoate (11.60 g, 31.57 mmol) was dissolved in dioxane (160 mL) and the solution was cooled to 10° C. in an ice bath. $LiOH—H_2O$, 1M (37.89 ml, 37.89 mmol) was added to the solution and the mixture was stirred at ambient temperature for 5 hours. The mixture was diluted with 2N HCl (100 mL) and $CH_2Cl_2$ (200 mL). Layers were separated and aqueous layer was extracted with $CH_2Cl_2$. The combined extracts were washed with brine (100 mL), dried over $MgSO_4$, filtered through a Celite pad and concentrated under reduced pressure. The crude material was purified by silica gel chromatography to provide 4-(4-(2-tert-butoxy-2-oxoethyl)-2-cyanophenoxy)benzoic acid (7.29 g) as a white solid.

Step C: To 4-(4-(2-tert-butoxy-2-oxoethyl)-2-cyanophenoxy)benzoic acid (0.34 g, 0.962 mmol), 2-(4-chlorophenyl)ethanamine (0.165 g, 1.06 mmol) in DMF (5 ml) was added diisopropylamine (0.200 ml, 1.15 mmol) and HBTU (0.149 g, 1.15 mmol). The reaction was stirred at ambient temperature for 90 minutes. The reaction was diluted with water and the product extracted into ethyl acetate. The combined organic layers were dried ($MgSO_4$), filtered and concentrated to give tert-butyl 2-(4-(4-((4-chlorophenethyl)carbamoyl)phenoxy)-3-cyanophenyl)acetate (0.40 g, 85%) as a white solid after column chromatography.

Step D: To tert-butyl 2-(4-(4-((4-chlorophenethyl)carbamoyl)phenoxy)-3-cyanophenyl)acetate (4.40 g, 8.96 mmol) in DCM (20 ml) was treated with TFA (20 ml). After stirring for 2 hours. The reaction mixture was concentrated and the crude material was purified by silica gel chromatography using a gradient of 0.5% MeOH/DCM containing 0.5% AcOH to 10% MeOH/DCM containing 0.5% AcOH to provide 2-(4-(4-((4-chlorophenethyl)carbamoyl)phenoxy)-3-cyanophenyl)acetic acid (3.30 g, 84.7% yield). $^1$H NMR (400 MHz, $CD_3OD$) 7.85 (d, 2H), 7.65 (s, 1H), 7.45 (d, 1H), 7.35 (s, 1H), 7.25 (d, 2H), 7.20 (d, 2H), 7.10 (d, 2H), 6.95 (d, 1H), 3.62 (m, 4H), 2.90 (t, 2H).

EXAMPLE 45

2-(3-cyano-4-(4-(2,4-dichlorophenethylcarbamoyl)phenoxy)phenyl)acetic acid

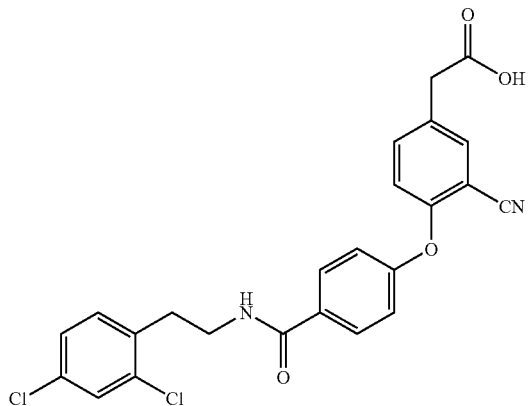

Prepared by the method of Example 44 substituting 2-(2,4-dichlorophenyl)ethanamine for 2-(4-chlorophenyl)ethanamine in Step D. $^1$H NMR (400 MHz, $CD_3Cl_3$, $CD_3OD$)

7.79 (d, 2H), 7.65 (m, 1H), 7.45 (d, 1H), 7.40 (m, 1H), 711 (m, 2H), 7.10 (d, 2H), 6.85 (d, 1H), 3.65 (m. 4H), 3.05 (t, 2H).

EXAMPLE 46

2-(3-bromo-4-(4-(2,4-dichlorophenethylcarbamoyl)phenoxy)phenyl)acetic acid

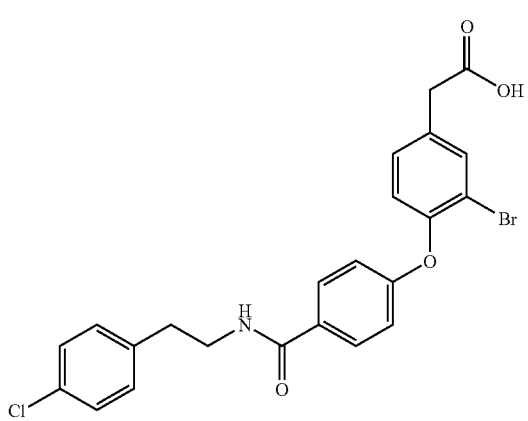

Step A: N-(4-chlorophenethyl)-4-hydroxybenzamide (1.5 g, 5.4 mmol) was diluted with DMSO (15 mL) followed by the addition of K$_2$CO$_3$ (0.89 g, 6.4 mmol) and 3-bromo-4-fluorobenzaldehyde (1.0 g, 4.9 mmol). The reaction was stirred at 85° C. overnight and then cooled to ambient temperature. The reaction mixture was diluted with ethyl acetate and washed with twice with 10% sodium carbonate, water and brine, and then concentrated. The crude material was purified by silica gel chromatography eluting with hexanes:ethyl acetate (1:1) and then 100% ethyl acetate to yield N-(4-chlorophenethyl)-4-(2-bromo-4-formylphenoxy)benzamide (1.6 g, 71% yield).

Step B: N-(4-chlorophenethyl)-4-(2-bromo-4-formylphenoxy)benzamide (1.6 g, 3.5 mmol) was diluted with THF (10 mL) followed by the addition of N,N,N-trimethyl(phenyl)methanaminium hydroxide (0.79 ml, 1.7 mmol) and methylsulfinyl(methylthio)methane (0.87 g, 7.0 mmol). The reaction was stirred at 70° C. for 2 hours. The reaction mixture was loaded directly onto a silica gel column and eluted with DCM:MeOH (98:2) to yield (Z)-N-(4-chlorophenethyl)-4-(2-bromo-4-(2-(methylsulfinyl)-2-(methylthio)vinyl)phenoxy)benzamide (1.9 g, 96% yield).

Step C: (Z)-N-(4-chlorophenethyl)-4-(2-bromo-4-(2-(methylsulfinyl)-2-(methylthio) vinyl)phenoxy)benzamide (2.0 g, 3.5 mmol) was treated with HCl (8.9 ml, 18 mmol) in ethanol. The reaction was stirred at 70° C. for 2 hours. The reaction was cooled and loaded directly onto a silica gel column eluting with hexanes:ethyl acetate (3:1) to yield ethyl 2-(4-(4-((4-chlorophenethyl)carbamoyl)phenoxy)-3-bromophenyl)acetate.

Step D: Ethyl 2-(4-(4-((4-chlorophenethyl)carbamoyl)phenoxy)-3-bromophenyl)acetate (30 mg, 0.058 mmol) was diluted with dioxane (500 μL) followed by the addition of NaOH (0.093 ml, 0.46 mmol) and 200 μL of water. After stirring for 3 hours, the reaction was diluted with ethyl acetate and 2N HCl. The layers were separated and the organic layer was dried over MgSO$_4$, filtered and concentrated to yield 2-(4-(4-((4-chlorophenethyl)carbamoyl)phenoxy)-3-bromophenyl)acetic acid (24 mg, 85% yield) as a white solid. $^1$H NMR (400 MHz, CD$_3$Cl$_3$, CD$_3$OD) 7.70 (d, 2H), 7.60 (s, 1H), 7.22-7.32 (m, 3H), 7.19 (d, 2H), 7.05 (d, 1H), 6.90 (d, 2H), 3.62 (m, 4H), 2.90 (t, 2H).

EXAMPLE 47

2-(4-(4-(4-chlorophenethylcarbamoyl)phenoxy)3,5-dimethylphenyl)acetic acid

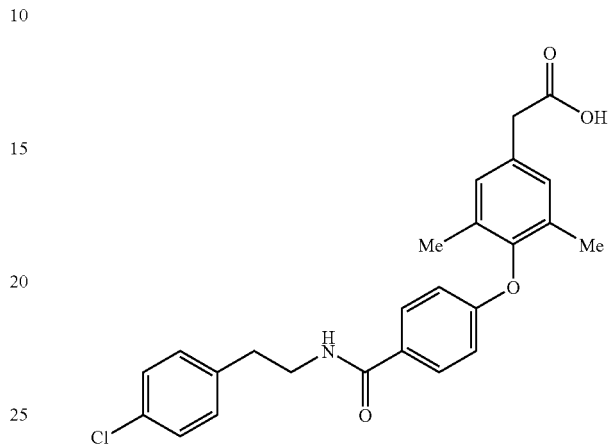

Prepared by the method of Example 46 substituting 4-fluoro-3,5-dimethylbenzaldehyde for 3-bromo-4-fluorobenzaldehyde in step A. $^1$H NMR (400 MHz, CD$_3$Cl$_3$, CD$_3$OD) 7.60 (d, 2H), 7.25 (d, 2H), 7.15 (d, 2H), 7.05 (s, 2H), 6.78 (d, 2H), 3.65 (t, 2H), 3.58 (s, 2H), 2.90 (t, 2H), 2.15 (s, 6H).

EXAMPLE 48

2-(4-(4-(4-chlorophenethylcarbamoyl)phenoxy)-3-methylphenyl)acetic acid

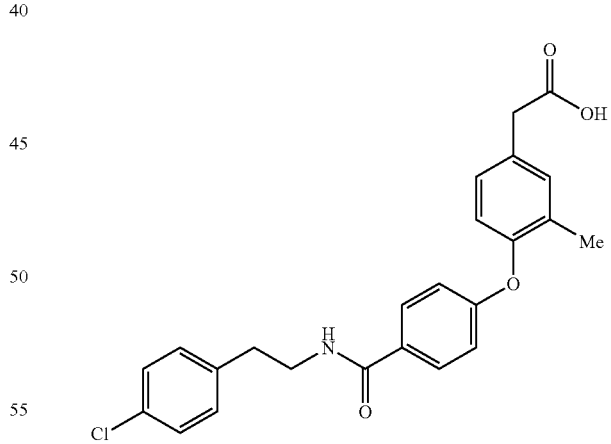

Step A: Ethyl 2-(4-(4-((4-chlorophenethyl)carbamoyl)phenoxy)-3-bromophenyl)acetate (Example 46 step C; 30 mg, 0.058 mmol) was diluted with THF (1 mL) followed by the addition of bis(tri-t-butylphosphine)palladium (0) (3.0 mg, 0.0058 mmol) and methylzinc chloride (0.087 ml, 0.17 mmol). After stirring for 2 hours, the reaction was loaded directly onto a silica gel column, eluting with hexanes:ethyl acetate (3:1) to yield ethyl 2-(4-(4-((4-chlorophenethyl)carbamoyl)phenoxy)-3-methylphenyl)acetate (20 mg, 76% yield) as a clear oil.

Step B: Ethyl 2-(4-(4-((4-chlorophenethyl)carbamoyl)phenoxy)-3-methylphenyl)acetate (20 mg, 0.0443 mmol) was diluted with dioxane (500 µL) followed by the addition of NaOH (0.0885 ml, 0.443 mmol) and 200 µL of water. After stirring for 3 hours, the reaction was diluted with ethyl acetate and 2N HCl. The layers were separated and the organic layer was dried over MgSO$_4$, filtered and concentrated to yield 2-(4-(4-((4-chlorophenethyl)carbamoyl)phenoxy)-3-methylphenyl)acetic acid (16.0 mg, 85.3% yield). NMR (400 MHz, CD$_3$Cl$_3$, CD$_3$OD) 7.62 (d, 2H), 7.30 (d, 2H), 7.10-7.22 (m, 4H), 6.92 (d, 1H), 6.85 (d, 2H), 3.65 (t, 2H), 3.60 (s, 2H), 2.90 (t, 2H), 2.15 (s, 3H).

EXAMPLE 49

2-(4-(4-(4-chlorophenethylcarbamoyl)phenoxy)-3-(thiophen-2-yl)phenyl)acetic acid

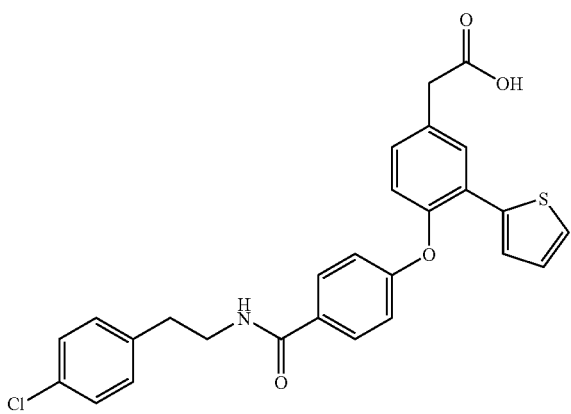

Step A: Ethyl 2-(4-(4-((4-chlorophenethyl)carbamoyl)phenoxy)-3-bromophenyl)acetate (Example 46 step C; 24 mg, 0.046 mmol) was diluted with THF (1 mL) followed by the addition of bis(tri-t-butylphosphine)palladium (0) (2.4 mg, 0.0046 mmol) and 2-thienylzinc bromide (0.23 ml, 0.12 mmol). After stirring for 2 hours, the reaction was purified by silica gel chromatography, eluting with hexanes:ethyl acetate (3:1) to yield ethyl 2-(4-(4-((4-chlorophenethyl) carbamoyl)phenoxy)-3-(thiophen-2-yl)phenyl)acetate (20 mg, 83% yield) as a clear oil.

Step B: Ethyl 2-(4-(4-((4-chlorophenethyl)carbamoyl)phenoxy)-3-(thiophen-2-yl)phenyl)acetate (20 mg, 0.038 mmol) was diluted with dioxane (500 µL) followed by the addition of NaOH (0.052 ml, 0.26 mmol) and 200 µL of water. After stirring for 3 hours, the reaction was diluted with ethyl acetate and 2N HCl. The layers were separated and the organic layer was dried over MgSO$_4$, filtered and concentrated to yield 2-(4-(4-((4-chlorophenethyl)carbamoyl)phenoxy)-3-(thiophen-2-yl)phenyl)acetic acid (7 mg, 37% yield) as a white solid. $^1$H NMR (400 MHz, CD$_3$Cl$_3$, CD$_3$OD) 7.69 (s, 1H), 7.64 (d, 2H), 7.45 (d, 1H), 7.30 (d, 2H), 7.22 (d, 1H), 7.15 (d, 2H), 6.98-7.05 (m, 2H), 6.90 (d, 2H), 3.65 (m, 4H), 2.90 (t, 2H).

EXAMPLE 50

2-(6-(4-(4-chlorophenethylcarbamoyl)phenoxy)biphenyl-3-yl)acetic acid

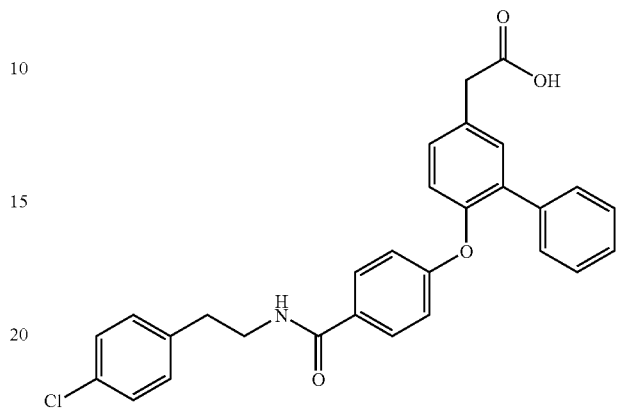

Step A: Ethyl 2-(4-(4-((4-chlorophenethyl)carbamoyl)phenoxy)-3-bromophenyl)acetate (Example 46 step C; 24 mg, 0.046 mmol) was diluted with THF (1 mL) followed by the addition of bis(tri-1-butylphosphine)palladium (0) (2.4 mg, 0.0046 mmol) and phenylzinc iodide (0.23 ml, 0.12 mmol). After stirring for 2 hours, the reaction was loaded directly onto a silica gel column and eluted with hexanes:ethyl acetate (3:1) to yield Ethyl 2-(6-(4-(4-chlorophenethylcarbamoyl)phenoxy)biphenyl-3-yl)acetate (15 mg, 63% yield) as a clear oil.

Step B: Ethyl 2-(6-(4-(4-chlorophenethylcarbamoyl)phenoxy)biphenyl-3-yl)acetate (10 mg, 0.0195 mmol) was diluted with dioxane (1 mL) followed by the addition of NaOH (0.0389 ml, 0.195 mmol) and 200 µL of water. After stirring for 2 hours, the reaction was diluted with ethyl acetate and 2N HCl. The layers were separated and the organic layer was dried over MgSO$_4$, filtered and concentrated to yield 2-(6-(4-(4-chlorophenethylcarbamoyl)phenoxy)biphenyl-3-yl)acetic acid (1.6 mg, 16.9% yield) as a white solid. MS ESI negative M−H=485.

EXAMPLE 51

2-(6-(4-(4-chlorophenethylcarbamoyl)phenoxy)-3'-(methylsulfonyl)biphenyl-3-yl)acetic acid

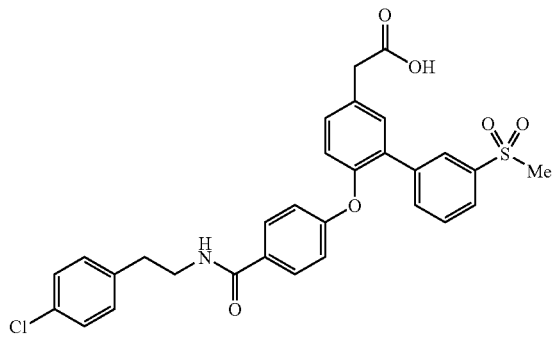

Step A: Ethyl 2-(4-(4-((4-chlorophenethyl)carbamoyl) phenoxy)-3-bromophenyl)acetate (Example 46 step C; 100 mg, 0.193 mmol), 3-(methanesulfonyl)phenylboronic acid (58.1 mg, 0.290 mmol), K$_2$CO$_3$ (80.2 mg, 0.580 mmol) and Pd(PPh$_3$), (22.4 mg, 0.0193 mmol) were diluted with dioxane (2 mL) and water (1 mL). The reaction was purged three times with nitrogen and stirred at 60° C. overnight. The reaction was cooled and loaded directly onto a silica gel column eluting with hexanes:ethyl acetate (2:1) to yield ethyl 2-(6-(4-(4-chlorophenethylcarbamoyl)phenoxy)-3'-(methylsulfonyl)biphenyl-3-yl)acetate (80 mg, 69.8% yield).

Step B: Ethyl 2-(6-(4-(4-chlorophenethylcarbamoyl)phenoxy)-3'-(methylsulfonyl)biphenyl-3-yl)acetate (80 mg, 0.135 mmol) was diluted with dioxane (1 mL) followed by the addition of NaOH (0.270 ml, 1.35 mmol) and 300 μL of water. After stirring for 2 hours, the reaction was diluted with ethyl acetate and 2N HCl. The layers were separated and the organic layer was dried over MgSO$_4$, filtered and concentrated. The material was purified using a biotage 12i cartridge eluting with 1-4% methanol/DCM to yield 2-(6-(4-(4-chlorophenethylcarbamoyl)phenoxy)-3'-(methylsulfonyl)biphenyl-3-yl)acetic acid (5 mg, 6.56% yield). $^1$H NMR (400 MHz, CD$_3$Cl$_3$, CD$_3$OD) 8.05 (s, 1H), 7.81 (d, 1H), 7.78 (d, 1H), 7.50-7.60 (m, 3H), 7.42 (s, 1H), 7.38 (d, 1H), 7.25 (d, 2H), 7.19 (d, 2H), 7.05 (d, 1H), 6.85 (d, 1H), 3.75 (s, 2H), 3.62 (q, 2H), 3.0 (s, 3H), 2.90 (t, 2H).

EXAMPLE 52

2-(4-(4-(4-chlorophenethylcarbamoyl)phenoxy)-3-cyclopropylphenyl)acetic acid

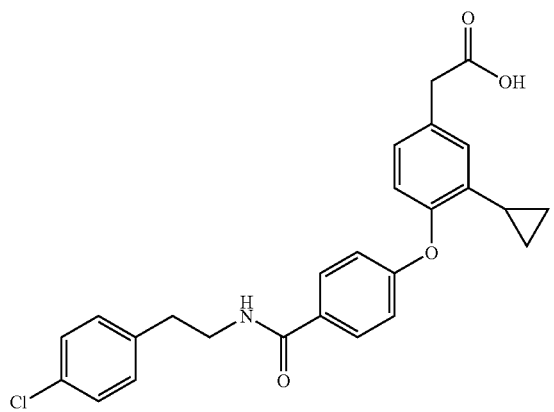

Step A: A flask was charged with cyclopropyl magnesium bromide (29.6 ml, 14.8 mmol) and placed under nitrogen. Zinc chloride (14.8 ml, 14.8 mmol) was added and the reaction was stirred for 20 minutes. 3-Bromo-4-fluorobenzaldehyde (1.0 g, 4.93 mmol) and bis(tri-t-butylphosphine)palladium (0) (0.126 g, 0.246 mmol) were diluted in 600 μL of THF and added to the reaction mixture. After stirring for 4 hours, the reaction was heated to 50° C. and stirred overnight. The reaction was cooled and quenched with saturated NH$_4$Cl and extracted with DCM. The organic layer was dried over MgSO$_4$, filtered and concentrated. The material was purified using a biotage 40M cartridge eluting with hexanes:ethyl acetate (4:1) to yield 3-cyclopropyl-4-fluorobenzaldehyde (400 mg, 49.5% yield)

Step B: N-(4-Chlorophenethyl)-4-hydroxybenzamide (504 mg, 1.83 mmol) was diluted with DMSO (8 mL) and K$_2$CO$_3$ (379 mg, 2.74 mmol) and 3-cyclopropyl-4-fluorobenzaldehyde (300 mg, 1.83 mmol) were added. The reaction was stirred 85° C. overnight. The reaction was cooled to ambient temperature, diluted with ethyl acetate and washed with twice with 10% sodium carbonate, water and brine, and concentrated. The crude material was purified by silica gel chromatography eluting with hexanes:ethyl acetate (3:1) to provide N-(4-chlorophenethyl)-4-(2-cyclopropyl-4-formylphenoxy)benzamide (160 mg, 20.9% yield).

Step C: N-(4-Chlorophenethyl)-4-(2-cyclopropyl-4-formylphenoxy)benzamide (160 mg, 0.381 mmol) was diluted with THF (3 mL) followed by the addition of N,N,N-trimethyl(phenyl)methanaminium hydroxide (0.0866 ml, 0.191 mmol) and methylsulfinyl(methylthio)methane (94.7 mg, 0.762 mmol). The reaction was heated to 70° C. and stirred for 2 hours. The reaction was cooled and loaded directly onto a silica gel column, eluting with ethyl acetate to yield (Z)-N-(4-chlorophenethyl)-4-(2-cyclopropyl-4-(2-(methylsulfinyl)-2-(methylthio)vinyl)phenoxy)benzamide (100 mg, 49.9% yield).

Step D: (Z)-N-(4-chlorophenethyl)-4-(2-cyclopropyl-4-(2-(methylsulfinyl)-2-(methylthio)vinyl)phenoxy)benzamide (100 mg, 0.190 mmol) was diluted with HCl (0.950 ml, 1.90 mmol), heated to 70° C. and stirred for 4 hours. The reaction was cooled and loaded directly onto a biotage 25 cartridge and eluted with hexanes:ethyl acetate (3:1) to yield ethyl 2-(4-(4-((4-chlorophenethyl)carbamoyl)phenoxy)-3-cyclopropylphenyl)acetate (70 mg, 77.0% yield) as a white solid.

Step E: Ethyl 2-(4-(4-((4-chlorophenethyl)carbamoyl) phenoxy)-3-cyclopropylphenyl)acetate (70 mg, 0.146 mmol) was diluted with dioxane (1 mL) followed by the addition of NaOH (0.293 ml, 1.46 mmol) and water (300 μL). After stirring for 3 hours, the reaction was diluted with ethyl acetate and 2N HCl. The layers were separated and the organic layer was dried over MgSO$_4$, filtered and concentrated to yield 2-(4-(4-((4-chlorophenethyl) carbamoyl)phenoxy)-3-cyclopropylphenyl)acetic acid (50 mg, 75.9% yield) as a white solid. $^1$H NMR (400 MHz, CD$_3$Cl$_3$, CD$_3$OD) 7.65 (d, 2H), 7.30 (d, 2H), 7.15 (d, 2H), 7.10 (d, 1H), 6.90 (m, 4H), 3.65 (1, 2H), 3.60 (s, 2H), 2.90 (t, 2H), 2.05 (m, 1H), 0.80 (m, 2H), 0.62 (m, 2H).

EXAMPLE 53

2-(4-(4-(4-chlorophenethylcarbamoyl)phenoxy)-3-ethylphenyl)acetic acid

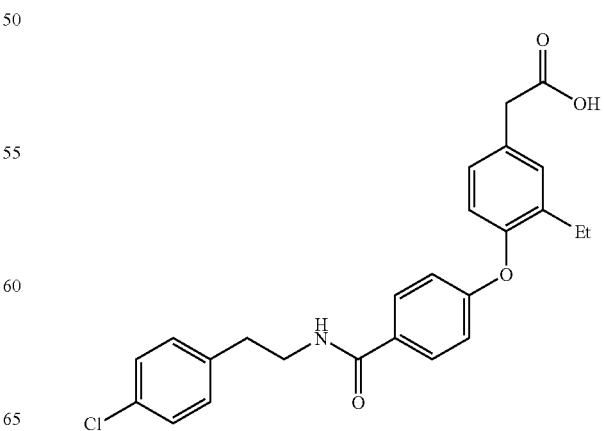

Step A: Ethyl 2-(4-(4-((4-chlorophenethyl)carbamoyl)phenoxy)-3-bromophenyl)acetate (Example 46 step C; 30 mg, 0.058 mmol) was diluted with THF (1 mL) followed by the addition of 1,1'-bis(diphenylphosphino)ferrocenedichloropalladium(II) (4.8 mg, 0.0058 mmol) and diethylzinc (0.13 ml, 0.15 mmol). After stirring for 4 hours, the reaction loaded directly onto a silica gel column, eluting with 5-50% ethyl acetate/hexane to yield ethyl 2-(4-(4-((4-chlorophenethyl)carbamoyl)phenoxy)-3-ethylphenyl)acetate (10 mg, 37% yield).

Step B: Ethyl 2-(4-(4-((4-chlorophenethyl)carbamoyl)phenoxy)-3-ethylphenyl)acetate (10 mg, 0.0215 mmol) was diluted with dioxane (500 μL) followed by the addition of NaOH (0.0429 ml, 0.215 mmol) and 5 drops of water. After stirring for 3 hours, the reaction was diluted with ethyl acetate and 2N HCl, and the layers were separated. The organic layer was dried over MgSO$_4$, filtered and concentrated. The crude material was purified by silica gel chromatography eluting with 10% MeOH/DCM to yield 2-(4-(4-((4-chlorophenethyl)carbamoyl)phenoxy)-3-ethylphenyl)acetic acid (2 mg, 21.3% yield). (400 MHz, CD$_3$Cl$_3$, CD$_3$OD) 7.65 (d, 2H), 7.30 (d, 2H), 7.10-7.25 (m, 4H), 6.90 (m, 3H), 3.62 (m, 2H), 3.40 (s, 1H), 2.90 (t, 2H), 2.55 (q, 2H), 1.15 (t, 3H).

EXAMPLE 54

2-(6-(4-(4-chlorophenethylcarbamoyl)phenoxy)-4'-(methylsulfonyl)biphenyl-3-yl)acetic acid

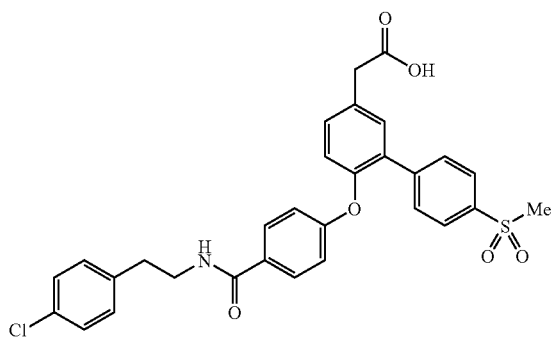

Step A: Ethyl 2-(4-(4-((4-chlorophenethyl)carbamoyl)phenoxy)-3-bromophenyl)acetate (Example 46 step C; 40 mg, 0.077 mmol), K$_2$CO$_3$ (32 mg, 0.23 mmol) and 4-(methylsulfonyl)phenylboronic acid (23 mg, 0.12 mmol) were diluted with dioxane (1 mL)/water (300 μL) followed by the addition of Pd(PPh$_3$)$_4$ (8.9 mg, 0.0077 mmol). The reaction was purged with nitrogen and stirred at 55° C. for 12 hours. The reaction was cooled and concentrated. The residue was taken up in minimal DCM and purified by silica gel chromatography, eluting with hexanes:ethyl acetate (1:1) to yield ethyl 2-(6-(4-(4-chlorophenethylcarbamoyl)phenoxy)-4'-(methylsulfonyl)biphenyl-3-yl)acetate (20 mg, 44% yield) as a clear oil.

Step B: Ethyl 2-(6-(4-(4-chlorophenethylcarbamoyl)phenoxy)-4'-(methylsulfonyl)biphenyl-3-yl)acetate (20 mg, 0.0338 mmol) was diluted with dioxane (1 mL) followed by the addition of NaOH (0.0676 ml, 0.338 mmol) and 300 μL of water. After stirring for 3 hours, the reaction was diluted with ethyl acetate and 2N HCl. The layers were separated and the organic layer was dried over MgSO$_4$, filtered and concentrated to yield 2-(6-(4-(4-chlorophenethylcarbamoyl)phenoxy)-4'-(methylsulfonyl)biphenyl-3-yl)acetic acid (10 mg, 52.5% yield). (400 MHz, CD$_3$Cl$_3$, CD$_3$OD) 7.90 (d, 2H), 7.70 (d, 2H), 7.60 (d, 2H), 7.40 (s, 1H), 7.35 (d, 1H), 7.25 (d, 2H), 7.15 (d, 2H), 7.05 (d, 1H), 6.85 (d, 2H), 6.55 (t, 1H), 3.63 (m, 4H), 3.05 (s, 3H), 2.90 (t, 2H).

EXAMPLE 55

2-(3-(methylsulfonamidomethyl)-4-(4-(3-(trifluoromethyl)phenethylcarbamoyl)phenoxy)phenyl)acetic acid

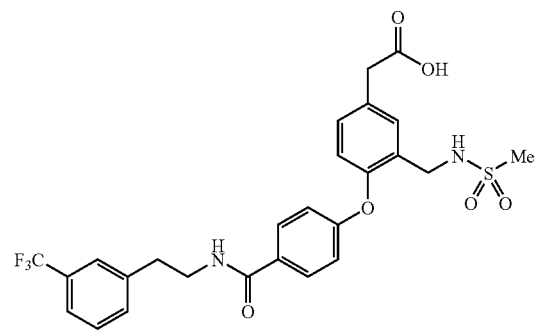

Prepared by the method of Example 14, substituting 3,4-dichlorobenzenamine in Step E with 2-(3-trifluoromethylphenyl)ethyanamine. MS+551.1 [M+1].

EXAMPLE 56

2-(3-(methylsulfonamidomethyl)-4-(4-(4-trifluoromethyl)phenethylcarbamoyl)phenoxy)phenyl)acetic acid

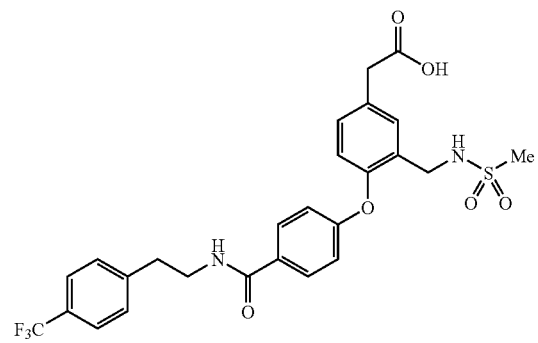

Prepared by the method of Example 14, substituting 3,4-dichlorobenzenamine in Step E with 2-(4-trifluoromethylphenyl)ethyanamine. MS+550.9 [M+1].

EXAMPLE 57

2-(4-(4-((1-(4-chlorophenyl)cyclopropyl)methylcarbamoyl)phenoxy)-3-(methylsulfonamidomethyl)phenyl)acetic acid

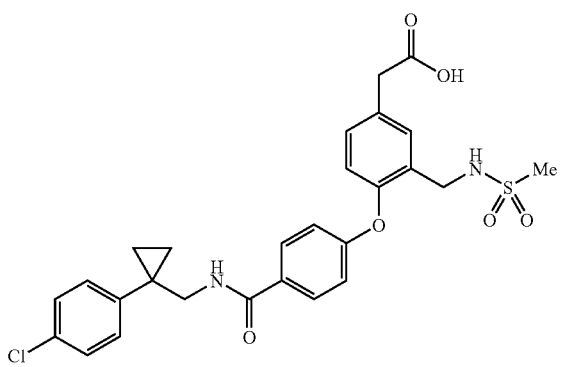

Prepared by the method of Example 14, substituting 3,4-dichlorobenzenamine in Step E with (1-(4-chlorophenyl)cyclopropyl)methanamine. MS–541.1 [M–1].

EXAMPLE 58

2-(4-(4-(4-chlorophenethylcarbamoyl)phenoxy)-3-(nicotinamidomethyl)phenyl)acetic acid

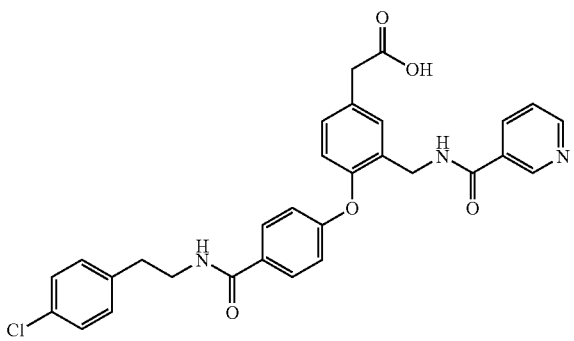

Step A: A mixture of tert-butyl 2-(3-cyano-4-fluorophenyl)acetate (1.32 g, 5.59 mmol), N-(4-chlorophenethyl)-4-hydroxybenzamide (1.85 g, 671 mmol), and potassium carbonate (0.93 g, 6.70 mmol) in DMSO (10 ml) was stirred at 90° C. for 1 day. The reaction was cooled, diluted with ethyl acetate, and washed with 10% aqueous $Na_2CO_3$. The aqueous layer was back extracted with ethyl acetate. The organic washes were combined, washed with 10% $Na_2CO_3$ and brine, dried over sodium sulfate and concentrated. The crude material was purified by silica gel chromatography, eluting with a gradient of 5% ethyl acetate/hexanes to 60% ethyl acetate/hexanes gave tert-butyl 2-(4-(4-((4-chlorophenethyl)carbamoyl)phenoxy)-3-cyanophenyl)acetate (1.09 g, 40%).

Step B: To tert-Butyl 2-(4-(4-((4-chlorophenethyl)carbamoyl)phenoxy)-3-cyanophenyl)acetate (1.09 g, 2.22 mmol) in 6 ml of 7 N ammonia in methanol at ambient temperature was added Raney-Ni (0.019 g) and the reaction was stirred under a balloon of hydrogen gas at ambient temperature. The reaction was filtered and concentrated to give tert-butyl 2-(4-(4-((4-chlorophenethyl)carbamoyl)phenoxy)-3-(aminomethyl)phenyl)acetate (0.160 g, 15%).

Step C: A mixture of tert-butyl 2-(4-(4-((4-chlorophenethyl)carbamoyl)phenoxy)-3-(aminomethyl)phenyl)acetate (0.015 g, 0.030 mmol), nicotinoyl chloride hydrochloride (0.007 g, 0.039 mmol), and triethylamine (0.013 ml, 0.091 mmol) in dichloromethane (1 ml) was stirred at ambient temperature for 1 hour. The reaction was loaded onto a silica gel sample and the product was eluted using a gradient system of 0.5% methanol/dichloromethane to 5% methanol/dichloromethane to provide tert-butyl 2-(4-(4-((4-chlorophenethyl)carbamoyl)phenoxy)-3-(nicotinamidomethyl)phenyl)acetate (0.005 g, 275%).

Step D: To a solution of tert-butyl 2-(4-(4-((4-chlorophenethyl)carbamoyl)phenoxy)-3-(nicotinamidomethyl)phenyl)acetate (0.005 g, 0.008 mmol) in dichloromethane (1.0 ml) was added TFA (1.0 ml) and the reaction was stirred at ambient temperature. After 1 hour the reaction was concentrated to give 2-(4-(4-((4-chlorophenethyl)carbamoyl)phenoxy)-3-(nicotinamidomethyl)phenyl)acetic acid (0.005 g). MS–449.1 [M–CO2H].

EXAMPLE 59

2-(4-(4-(4-chlorophenethylcarbamoyl)phenoxy)-3-((pyridine-3-sulfonamido)methyl)phenyl)acetic acid

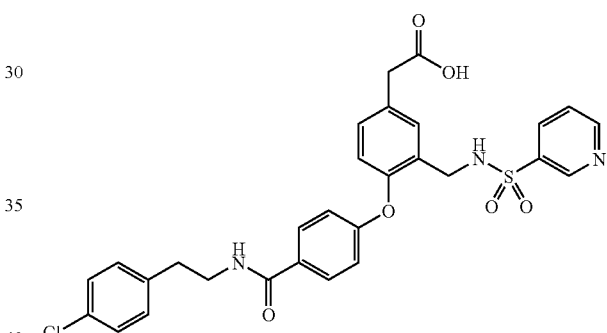

Prepared by the method of Example 58, substituting nicotinoyl chloride hydrochloride in Step C with pyridine-3-sulfonyl chloride hydrochloride. MS–578.1 [M–1].

EXAMPLE 60

2-(4-(4-(4-chlorophenethylcarbamoyl)phenoxy)-3-((1-methyl-1H-imidazole-5-sulfonamido)methyl)phenyl)acetic acid

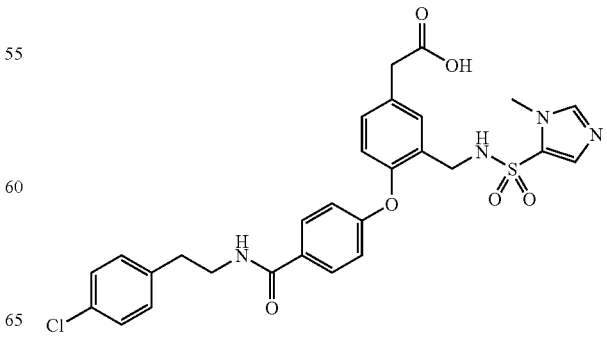

Prepared by the method of Example 58, substituting nicotinoyl chloride hydrochloride in Step C with 1-methyl-1H-imidazole-4-sulfonyl chloride. MS−581.2 [M−1].

EXAMPLE 61

2-(4-(4-(4-chlorophenethylcarbamoyl)phenoxy)-3-((6-dimethylamino)nicotinamido)methyl)phenyl)acetic acid

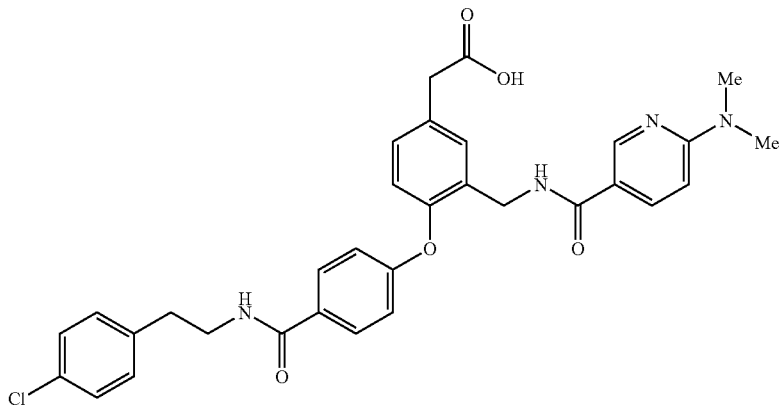

Prepared by the method of Example 58, substituting nicotinoyl chloride hydrochloride in Step C with 6-(dimethylamino)nicotinic acid. MS−585.2 [M−1].

EXAMPLE 62

2-(4-(4-(4-chlorophenethylcarbamoyl)phenoxy)-3-((2-(4-fluorophenylsulfonamido)acetamido)methyl)phenyl)acetic acid

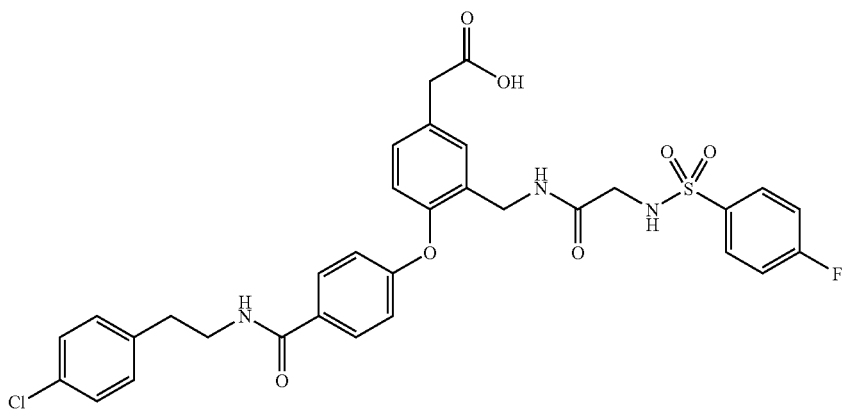

Prepared by the method of Example 58, substituting nicotinoyl chloride hydrochloride in Step C with 2-(4-fluorophenylsulfonamido)acetic acid. MS–608.4 [M–CO2H].

EXAMPLE 63

2-(3-((6-aminonicotinamido)methyl)-4-(4-(4-chlorophenethylcarbamoyl)phenoxy)phenyl)acetic acid

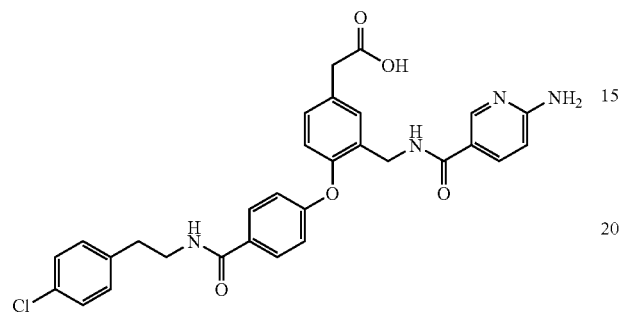

Prepared by the method of Example 58, substituting nicotinoyl chloride hydrochloride in Step C with 6-aminonicotinic acid. MS–557.1 [M–1].

EXAMPLE 64

2-(4-(4-(4-chlorophenethylcarbamoyl)phenoxy)-3-((dimethylamino)methyl)phenyl)acetic acid

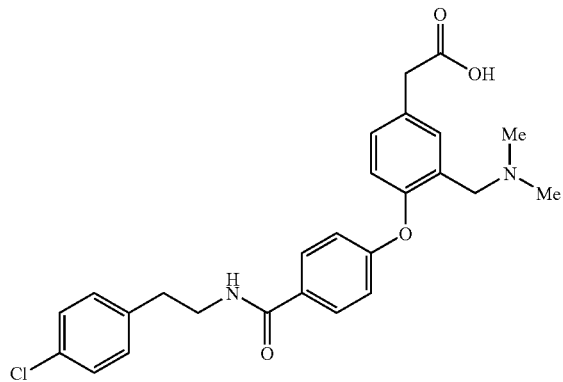

Step A: To a stirred solution of tert-butyl 2-(3-(aminomethyl)-4-(4-(phenethylcarbamoyl)phenoxy)phenyl)acetate (0.015 g, 0.030 mmol) in methanol (1 ml) was added acetic acid (0.012 ml, 0.212 mmol), sodium cyanoborohydride (0.010 g, 0.152 mmol) and paraformaldehyde (0.007 g, 0.152 mmol). The reaction was stirred at ambient temperature for 1 hour. The reaction was loaded directly onto a silica gel sample and the product eluted using a gradient of 0.5% methanol/dichloromethane to 5% methanol/dichloromethane to provide tert-butyl 2-(4-(4-((4-chlorophenethyl)carbamoyl)phenoxy)-3-((dimethylamino)methyl)phenyl)acetate (0.005 g, 0.010 mmol).

Step B: To tert-butyl 2-(4-(4-((4-chlorophenethyl)carbamoyl)phenoxy)-3-((dimethylamino)methyl)phenyl)acetate (0.005 g, 0.010 mmol) in dichloromethane (1.0 ml) was added TFA (1.0 ml) and the reaction stirred for 1 hour at ambient temperature. The reaction was concentrated to give 2-(4-(4-((4-chlorophenethyl)carbamoyl)phenoxy)-3-((dimethylamino)methyl)phenyl)acetic acid (0.005 g). MS–465.1 [M–1].

EXAMPLE 65

2-(4-(4-(4-chlorophenethylcarbamoyl)phenoxy)-3-((N-methylmethylsulfonamido)methyl)phenyl)acetic acid

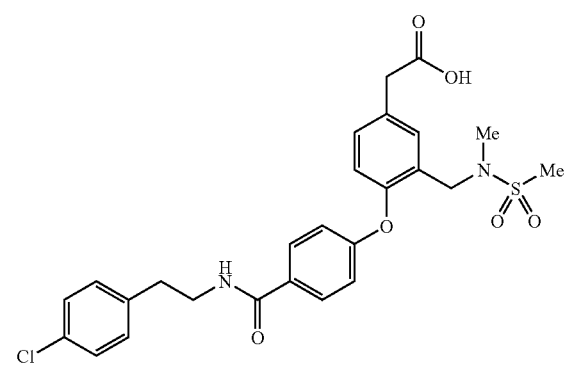

Step A: To a stirred solution of tert-butyl 2-(3-cyano-4-fluorophenyl)acetate (1.00 mg, 4.25 mmol) and methyl 4-hydroxybenzoate (776 mg, 5.10 mmol) in DMSO (20 ml) was added $K_2CO_3$ (704 mg, 5.10 mmol). The reaction was heated to 90° C. overnight via an oil bath. The reaction was diluted with ethyl acetate and 10% aqueous sodium carbonate. The aqueous phase was extracted with ethyl acetate and the combined organic layers were washed with 10% aqueous sodium carbonate and brine, dried over $MgSO_4$, concentrated and purified by silica gel chromatography to give methyl 4-(4-(2-tert-butoxy-2-oxoethyl)-2-cyanophenoxy)benzoate (1.08 g).

Step B: To a stirred solution of the methyl 4-(4-(2-tert-butoxy-2-oxoethyl)-2-cyanophenoxy)benzoate (1.086 mg, 2.96 mmol) in 7N ammonia/methanol (30 ml) under nitrogen was added Raney Nickel (25.3 mg, 0.296 mmol). The reaction was purged with a hydrogen balloon and stirred under hydrogen overnight. The reaction was filtered through GF paper and the solid catalyst was rinsed with methanol and ethyl acetate. The filtrate was concentrated, and the crude product was purified by silica gel chromatography to give methyl 4-(2-(aminomethyl)-4-(2-tert-butoxy-2-oxoethyl)phenoxy)benzoate (0.69 g).

Step C: To a stirred solution of the methyl 4-(2-(aminomethyl)-4-(2-tert-butoxy-2-oxoethyl)phenoxy)benzoate (690 mg, 1.86 mmol) in dichloromethane (6 ml) was added pyridine (225 µL, 2.78 mmol) followed by methanesulfonyl chloride (287 µL, 3.71 mmol). The reaction was stirred at ambient temperature for 4 hours, after which time additional pyridine (1.5 eq) and methanesulfonyl chloride (2 eq) were added. The reaction was stirred for an additional hour and then diluted with ethyl acetate and 1M HCl. The aqueous layer was extracted with ethyl acetate and the combined organics washed with brine and dried over $MgSO_4$. The crude product was then purified on the Biotage Horizon (40+M, 5% to 75% B:ethyl acetate) to give methyl 4-(4-(2-tert-butoxy-2-oxoethyl)-2-(methylsulfonamidomethyl)phenoxy)benzoate (0.754 g).

Step D: To a stirred solution of the methyl 4-(4-(2-tert-butoxy-2-oxoethyl)-2-(methylsulfonamidomethyl)phenoxy)benzoate (745 mg, 1.65 mmol) in DMF (10 ml) was added MeI (155 µL, 2.48 mmol) followed by $K_2CO_3$ (343 mg, 2.48 mmol). The reaction was stirred at ambient temperature for 3 hours, then diluted with ethyl acetate and 2M HCl. The aqueous phase was extracted with ethyl acetate, and the combined organic layers were washed with brine and dried over MgSO$_4$. The crude mixture was purified by silica gel chromatography to give methyl 4-(4-(2-tert-butoxy-2-oxoethyl)-2-((N-methylmethylsulfonamido)methyl)phenoxy)benzoate (0.368 g).

Step E: To a stirred solution of methyl 4-(4-(2-tert-butoxy-2-oxoethyl)-2-((N-methylmethylsulfonamido)methyl)phenoxy)benzoate (370 mg, 0.797 mmol) in dioxane (8 ml) was added a solution of LiOH monohydrate (43.5 mg, 1.04 mmol) in water (2 ml) (0.1 M solution 4:1 dioxane/water). The reaction was stirred for 5 hours, then diluted with dichloromethane and 2 N HCl. The aqueous phase was extracted with dichloromethane and the combined organic layers were washed with brine and dried over MgSO$_4$. The crude product was purified by silica gel chromatography to give 4-(4-(2-tert-butoxy-2-oxoethyl)-2-((N-methylmethylsulfonamido)methyl)phenoxy)benzoic acid (0.253 g).

Step F: To a stirred solution of 4 (4 (2 tert-butoxy-2-oxoethyl)-2-((N-methylmethylsulfonamido)methyl)phenoxy)benzoic acid (50 mg, 0.111 mmol) and HATU (46.5 mg, 0.122 mmol) in DMF (1 ml) was added DIEA (23.2 µL, 0.133 mmol) followed by 2-(4-chlorophenyl)ethanamine (11.2 µL, 0.111 mmol). The reaction was diluted with water and extracted with ethyl acetate. The combined organics were washed with brine and dried over MgSO$_4$. The crude product was purified by silica gel chromatography to give tert-butyl 2-(4-(4-((4-chlorophenethyl)carbamoyl)phenoxy)-3-((N-methylmethylsulfonamido)methyl)phenyl)acetate (0.0115 g).

Step G: To a stirred solution of tert-butyl 2-(4-(4-((4-chlorophenethyl)carbamoyl)phenoxy)-3-((N-methylmethylsulfonamido)methyl)phenyl)acetate (11.5 mg, 0.019 mmol) in dichloromethane (1 ml) was added TFA (500 µl). The reaction was stirred at ambient temperature for 4 hours and then concentrated. The crude product was then purified by preparative TLC (20% methanol/dichloromethane/0.5% AcOH) to give 2-(4-(4-((4-chlorophenethyl)carbamoyl)phenoxy)-3-((N-methylmethan-2-ylsulfonamido)methyl)phenyl)acetic acid (0.0123 g). MS +531.0 [M+1].

EXAMPLE 66

2-(3-cyano-4-(4-(phenethylcarbamoyl)phenoxy)phenyl)acetic acid

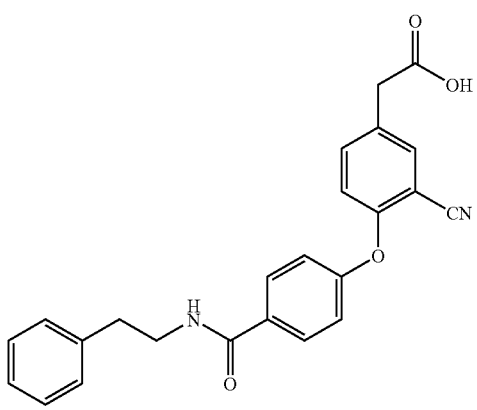

Step A: A mixture of tert-butyl 2-(3-cyano-4-fluorophenyl)acetate (0.122 g), N-(4-chlorophenethyl)-4-hydroxybenzamide (0.150 g), and potassium carbonate (0.086 g) was dissolved in 2 ml of DMSO and stirred at 90° C. After 1 day, the reaction was cooled, loaded onto a silica gel sample and product eluted with a solvent system gradient of 0.5% methanol/dichloromethane to 5% methanol/dichloromethane to give tert-butyl 2-(3-cyano-4-(4-(phenethylcarbamoyl)phenoxy)phenyl)acetate (0.120 g).

Step B: To a solution of tert-butyl 2-(3-cyano-4-(4-(phenethylcarbamoyl)phenoxy)phenyl)acetate 0.120 g) in 2 ml of dichloromethane was added 2 ml of TFA and the reaction was stirred at ambient temperature. After 1 hour the reaction was concentrated and dried under vacuum to give 2-(3-cyano-4-(4-(phenethylcarbamoyl)phenoxy)phenyl)acetic acid (0.100 g). MS–355.3 [M–CO2H].

EXAMPLE 67

2-(4-(4-(4-chlorophenethylcarbamoyl)-3-(trifluoromethyl)phenyl)acetic acid

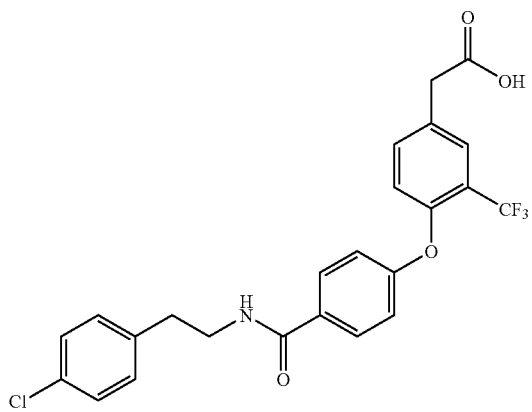

Step A: To a stirred solution of the 4-fluoro-3-(trifluoromethyl)benzaldehyde (177 µL, 1.30 mmol) and N-(4-chlorophenethyl)-4-hydroxybenzamide (359 mg, 1.30 mmol) in DMSO (3 ml) was added K$_2$CO$_3$ (270 mg, 1.95 mmol). The reaction was stirred at 95° C. for 2 hours and then directly purified by silica gel chromatography to give N-(4-chlorophenethyl)-4-(4-formyl-2-(trifluoromethyl)phenoxy)benzamide (0.541 g).

Step B: To a solution of N-(4-chlorophenethyl)-4-(4-formyl-2-(trifluoromethyl)phenoxy)benzamide (0.225 g, 0.502 mmol) in THF (5 ml) was added methylsulfinyl(methylthio)methane (0.125 g, 1.00 mmol) followed by benzyltrimethylammonium hydroxide (0.114 ml, 0.251 mmol) and the reaction was stirred at 70° C. fort hour. The reaction was cooled, loaded onto a silica gel sample and the product was eluted using a gradient of 0.5% methanol/dichloromethane to 15% methanol/dichloromethane. Isolated (Z)-N-(4-chlorophenethyl)-4-(4-(2-(methylsulfinyl)-2-(methylthio)vinyl)-2-(trifluoromethyl)phenoxy)benzamide (0.220 g, 79.0% yield) which by TLC appeared to be a 4:1 mixture of olefin isomers. The crude material was used directly in the next step.

Step C: To (Z)-N-(4-chlorophenethyl)-4-(4-(2-(methylsulfinyl)-2-(methylthio)vinyl)-2-(trifluoromethyl)phenoxy)benzamide (0.220 g, 0.397 mmol) was added HCl (in ethanol) (0.993 ml, 1.99 mmol) and the reaction heated to 70° C. for 1 hour. The reaction was concentrated, loaded onto silica gel and the product eluted using a gradient of 5% ethyl acetate/hexanes to 75% ethyl acetate/hexanes. Isolated ethyl 2-(4-(4-((4-chlorophenethyl)carbamoyl)phenoxy)-3-(trifluoromethyl)phenyl)acetate (0.165 g, 82.1% yield) as a white solid.

Step D: To a solution of ethyl 2-(4-(4-((4-chlorophenethyl)carbamoyl)phenoxy)-3-(trifluoromethyl)phenyl)acetate (0.165 g, 0.326 mmol) in methanol/THF (1:1), 5 ml was added LiOH—H$_2$O (0.0684 g, 1.63 mmol) and 3 drops of water, and the reaction was stirred for 1 hour The reaction was diluted with ethyl acetate, washed with 2N HCl and brine, dried over magnesium sulfate and concentrated. The crude material was purified by silica gel chromatography, eluting with a gradient of 0.5% methanol/dichloromethane containing 0.5% AcOH to 7% methanol/dichloromethane containing 0.5% AcOH to provide 2-(4-(4-((4-chlorophenethyl) carbamoyl)phenoxy)-3-(trifluoromethyl)phenyl)acetic acid (0.112 g). MS+478.3 [M+1]. $^1$H NMR (400 MHz, CD$_3$OD) δ 8.49 (bt, NH), 7.79 (d, J=8.7 Hz, 2H), 7.68 (s, 1H), 7.53 (d, J=4.3 Hz, 1H), 7.28 (d, J=8.5 Hz, 2H), 7.23 (d, J=8.6 Hz, 2H), 7.02-7.06 (m, 3H), 3.71 (s, 2H), 3.56 (t, J=6.8 Hz, 2H), 2.90 (t, J=7.3 Hz, 2H).

EXAMPLE 68

2-(4-(4-(4-chlorophenethylcarbamoyl)phenoxy)-3-cyanophenyl)propanoic acid

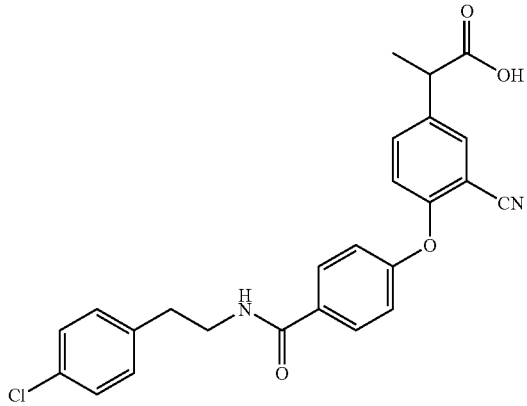

Step A: To a stirred solution of diisopropylamine in 2 ml of THF at −78° C. was added n-butyl lithium (0.61 ml). The reaction was stirred for 30 minutes after which time a solution of tert-butyl 2-(3-cyano-4-fluorophenyl)acetate (0.300 g) in THF (2 ml) was added dropwise over 20 minutes at −78° C. The reaction was warmed to 0° C. and then transferred a flask containing 2 ml THF and MeI (0.080 ml). The reaction was acidified with 2M HCl and extracted with ethyl acetate. The combined organics were then washed with brine and dried over MgSO$_4$. The concentrated product was purified by silica gel chromatography using a solvent system of 5% to 50% ethyl acetate/hexanes to provide tert-butyl 2-(3-cyano-4-fluorophenyl)propanoate (0.140 g).

Step B: A flask was charged with tert-butyl -(3-cyano-4-fluorophenyl)propanoate (0.070 g), N-(4-chlorophenethyl)-4-hydroxybenzamide (0.105 g), and potassium carbonate (0.047 g) in 1 ml of DMSO and stirred at 95 ° C. for one day. The reaction was taken up in dichloromethane and washed with water. The organic layer was collected, dried over MgSO$_4$, filtered, and concentrated. The crude material was purified by silica gel chromatography, eluting with a solvent system of 5%-80% ethyl acetate/hexanes gave tert-butyl 2-(4-(4-((2,4-dichlorophenethyl)carbamoyl)phenoxy)-3-cyanophenyl)propanoate (0.102 g).

Step C: A flask was charged with tert-butyl 2-(4-(4-((4-chlorophenethyl)carbamoyl)phenoxy)-3-cyanophenyl)propanoate (0.098 g) in 1 ml of dichloromethane and 1 ml of TFA, and the reaction was stirred for 1 hour. The reaction was concentrated and dried under vacuum. Isolated 2-(4-(4-((4-chlorophenethyl)carbamoyl)phenoxy)-3-cyanophenyl)propanoic acid (0.080 g). MS+449.1 [M+1].

EXAMPLE 69

2-(3-cyano-4-(2,4-dichlorophenethylcarbamoyl)phenoxy)phenyl)propanoic acid

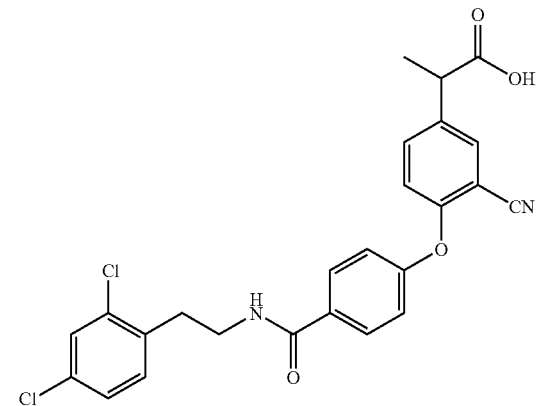

Prepared by the method of Example 68 substituting N-(4-chlorophenethyl)-4-hydroxybenzamide in step B with N-(2, 4-dichlorophenethyl)-4-hydroxybenzamide. MS+483.0 [M+1].

EXAMPLE 70

2-(4-(4-(4-chlorophenethylcarbamoyl)phenoxy)-3-methoxyphenyl)acetic acid

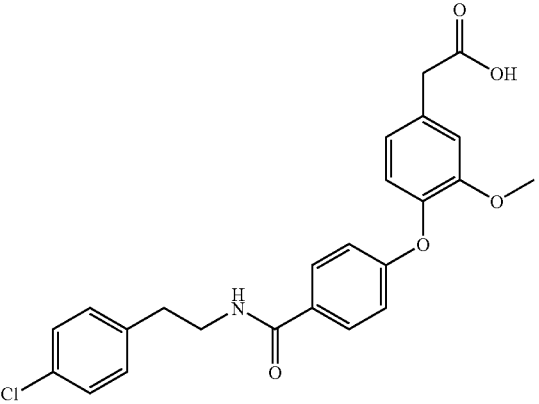

Step A: Methyl 2-(4-hydroxy-3-methoxyphenyl)acetate (0.204 g, 1.04 mmol), N-(4-chlorophenethyl)-4-iodobenzamide (0.200 g, 0.519 mmol), 2,2,6,6-tetramethyl-3,5-heptanedione (0.00956 g, 0.0519 mmol), Cu(I)Cl (0.0257 g, 0.259 mmol) and Cs$_2$CO$_3$ (0.338 g, 1.04 mmol) were stirred together in NMP (2 ml) for 1 hour. The reaction was loaded onto silica gel and the product eluted using a gradient of 5% ethyl acetate/hexanes to 100% ethyl acetate/hexanes. Isolated methyl 2-(4-(4-((4-chlorophenethyl)carbamoyl)phenoxy)-3-methoxyphenyl)acetate (0.105 g, 44.6% yield) as a yellow solid.

Step B: To a solution of methyl 2-(4-(4-((4-chlorophenethyl)carbamoyl)phenoxy)-3-methoxyphenyl)acetate (0.065 g, 0.143 mmol) in methanol/THF (1:1, 3 ml) was added NaOH (0.100 ml, 0.500 mmol). After 5 minutes, reaction was quenched with 10 ml of 2N HCl and the product was extracted into ethyl acetate. The organic layer was washed with brine, dried over magnesium sulfate and concentrated. The crude material was purified by silica gel chromatography, eluting with a gradient of 0.5% methanol/dichloromethane (containing 0.5% AcOH) to 7.5% methanol/dichloromethane containing (0.5% AcOH) to provide 2-(4-(4-((4-chlorophenethyl)carbamoyl)phenoxy)-3-methoxyphenyl)acetic acid (0.041 g, 65.1% yield) as a white solid. $^1$H NMR (400 MHz, CD$_3$OD) δ 8.37-8.41 (bt, NH), 7.70 (d, J=8.7 Hz, 2H), 7.28 (d, J=8.6 Hz, 2H), 7.23 (d, J=8.5 Hz, 2H), 7.08 (s, 1H), 7.02 (d, J=8.6 Hz, 1H), 6.91 (d, J=8.6 Hz, 2H), 3.64 (s, 2H), 3.56 (t, J=6.8 Hz, 2H), 2.88 (t, J=7.4 Hz, 2H).

EXAMPLE 71

2-(3-cyano-4-(4-(2,4-dichlorophenethylcarbamoyl)-3-fluorophenoxy)phenyl)acetic acid

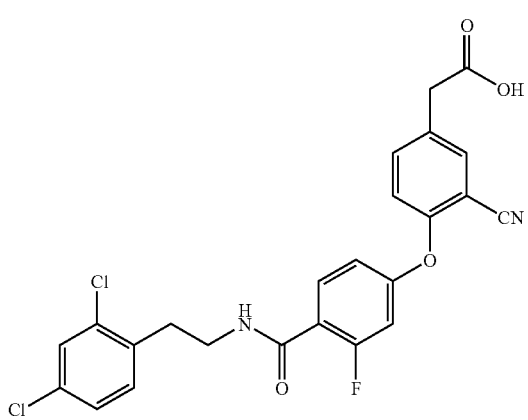

Step A: To a stirred solution of 2-fluoro-4-hydroxybenzoic acid (200 mg, 1.28 mmol) in DMF (3 ml) at ambient temperature were added HATU (536 mg, 1.41 mmol) and DIEA (268 μL, 1.54 mmol). The reaction was stirred for 30 minutes and then 2-(2,4-dichlorophenyl)ethanamine (193 μL, 1.28 mmol) was added. The reaction was stirred overnight, then concentrated and diluted with water and dichloromethane. The aqueous layer was extracted with dichloromethane and the combined organic layers were washed with brine and dried over MgSO$_4$. The crude product was purified by silica gel chromatography) to give N-(2,4-dichlorophenethyl)-2-fluoro-4-hydroxybenzamide (0.420 g).

Step B: To a stirred solution of N-(2,4-dichlorophenethyl)-2-fluoro-4-hydroxybenzamide (420 mg, 1.28 mmol) and tert-butyl 2-(3-cyano-4-fluorophenyl)acetate (361 mg, 1.54 mmol) in DMSO (6 ml) was added K$_2$CO$_3$ (265 mg, 1.92 mmol). The reaction was heated stirred at 70° C. for one hour. The reaction was then stirred at 90° C. overnight. The reaction was diluted with water and ethyl acetate. The aqueous phase was extracted with ethyl acetate and the combined organic layers were washed with 10% Na$_2$CO$_3$ and brine, dried over MgSO$_4$, filtered and concentrated. The crude product was purified by silica gel chromatography to give tert-butyl 2-(4-(4-((2,4-dichlorophenethyl)carbamoyl)-3-fluorophenoxy)-3-cyanophenyl)acetate (0.0157 g).

Step C: To a stirred solution of tert-butyl 2-(4-(4-((2,4-dichlorophenethyl)carbamoyl)-3-fluorophenoxy)-3-cyanophenyl)acetate (15 mg, 0.0276 mmol) in dichloromethane was added TFA. The reaction was stirred for 2 hours and then concentrated. The crude material was purified by preparative TLC (10% methanol/0.5% AcOH/dichloromethane). The appropriate section was collected and then purified a second time by preparative TLC to provide 2-(4-(4-((2,4-dichlorophenethyl)carbamoyl)-3-fluorophenoxy)-3-cyanophenyl)acetic acid (0.0042 g). $^1$H NMR (400 MHz, CD$_3$OD) δ 7.70-7.74 (m, 2H), 7.61 (d, J=7.8 Hz, 1H), 7.43 (s, 1H), 7.33 (d, J=8.6 Hz, 1H), 7.26 (d, J=7.8 Hz, 1H), 7.13 (d, J=8.7 Hz, 1H), 6.88-6.94 (m, 2H), 3.52-3.65 (m, 4H), 3.05 (t, J=7.0 Hz, 2H).

EXAMPLE 72

2-(3-cyano-4-(4-(2,6-dichlorophenethylcarbamoyl)phenoxy)phenyl)acetic acid

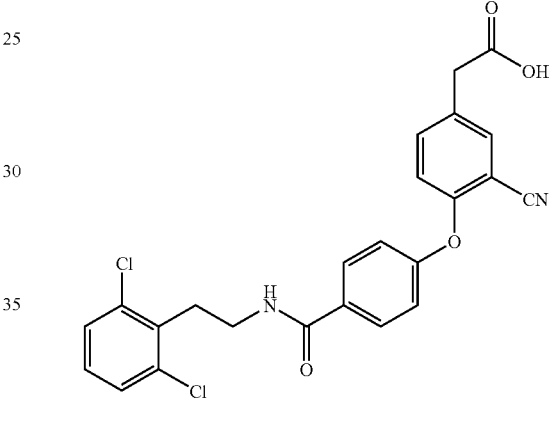

Step A: TFP Resin (1.33 mmol/g; 2.872 g, 3.820 mmol) was placed in a vessel and DMA (5 mL) was added to swell the resin. The vessel was placed on a shaker for 15 minutes, and 4-(4-(2-tert-butoxy-2-oxoethyl)-2-cyanophenoxy)benzoic acid (1.500 g, 4.245 mmol), DIC (0.7311 ml, 4.669 mmol), and DMAP (0.5704 g, 4.669 mmol) were added to the mixture and the vessel was placed on the shaker. The mixture was filtered, washed with DMA, THF, dichloromethane, and ether, and air-dried to give 3.11 g of the resin bound (4-(4-(2-tert-butoxy-2-oxoethyl)-2-cyanophenoxy)benzoate.

Step B: TFP resin bound ester (4-(4-(2-tert-butoxy-2-oxoethyl)-2-cyanophenoxy)benzoate) (0.1968 g, 0.09840 mmol) was added to a vial. THF (2 ml) was added and the resin was allowed to swell. 2-(2,6-Dichlorophenyl)ethanamine, (1M in THF; 0.08200 ml, 0.082 mmol) was added to the vial and the vial was place on a shaker. After 16 hours, the mixture was decanted and the resin was rinsed with THF (3×2 ml). The combined THF solution was concentrated under reduced pressure. The residue was dried under high vacuum to give tert-butyl 2-(4-(4-((2,6-dichlorophenethyl)carbamoyl)phenoxy)-3-cyanophenyl)acetate (0.034 g), which was used in the nest step without further purification.

Step C: tert-Butyl 2-(4-(4-((2,6-dichlorophenethyl)carbamoyl)phenoxy)-3-cyanophenyl)acetate (34 mg, 0.065 mmol) was dissolved in dichloromethane (1 ml) and TFA (1 ml) was added. After stirring for 45 minutes, the mixture was concentrated under reduced pressure to give 2-(3-cyano-4-(4-(2,6-dichlorophenethylcarbamoyl)phenoxy)phenyl)acetic acid (0.034 g).

EXAMPLE 73

2-(3-cyano-4-(4-(4-fluorophenethylcarbamoyl)phenoxy)phenyl)acetic acid

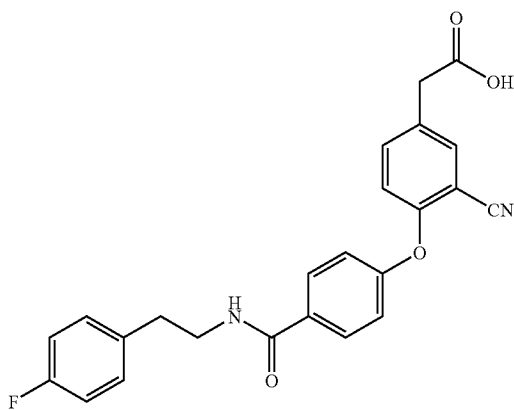

Prepared by the method of Example 72 substituting 2-(2,6-dichlorophenyl)ethanamine in Step B with 2-(4-fluorophenyl)ethanamine.

EXAMPLE 74

2-(3-cyano-4-(4-(3-methoxyphenethylcarbamoyl)phenoxy)phenyl)acetic acid

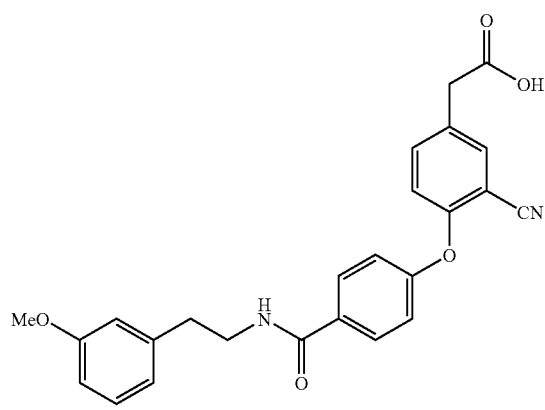

Prepared by the method of Example 72 substituting 2-(2,6-dichlorophenyl)ethanamine in Step B with 2-(3-methoxyphenyl)ethanamine.

EXAMPLE 75

2-(3-cyano-4-(4-(4-tert-butylphenethylcarbamoyl)phenoxy)phenyl)acetic acid

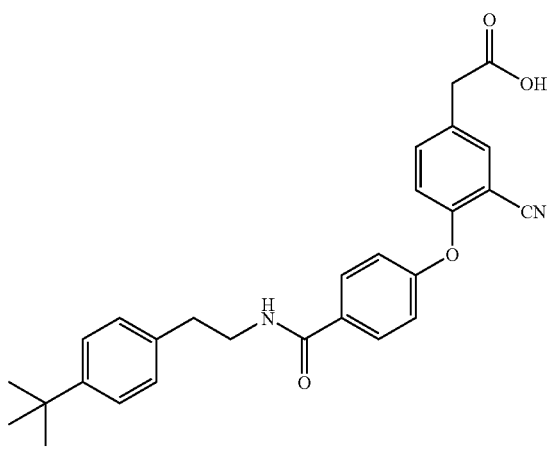

Prepared by the method of Example 72 substituting 2-(2,6-dichlorophenyl)ethanamine in Step B with 2-(4-tert-butylphenyl)ethanamine.

EXAMPLE 76

2-(3-cyano-4-(4-(4-trifluoromethylphenethylcarbamoyl)phenoxy)phenyl)acetic acid

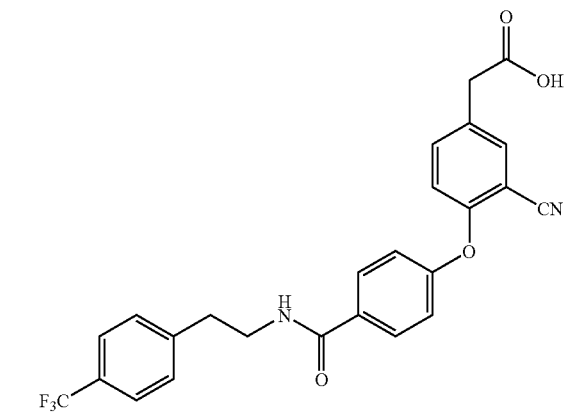

71

Prepared by the method of Example 72 substituting 2-(2,6-dichlorophenyl)ethanamine in Step B with 2-(4-trifluoromethylphenyl)ethanamine.

EXAMPLE 77

2-(3-cyano-4-(4-(3-chlorophenethylcarbamoyl)phenoxy)phenyl)acetic acid

72

Prepared by the method of Example 72 substituting 2-(2,6-dichlorophenyl)ethanamine in Step B with 2-(3-fluorophenyl)ethanamine.

EXAMPLE 79

2-(3-cyano-4-(4-(4-methoxyphenethylcarbamoyl)phenoxy)phenyl)acetic acid

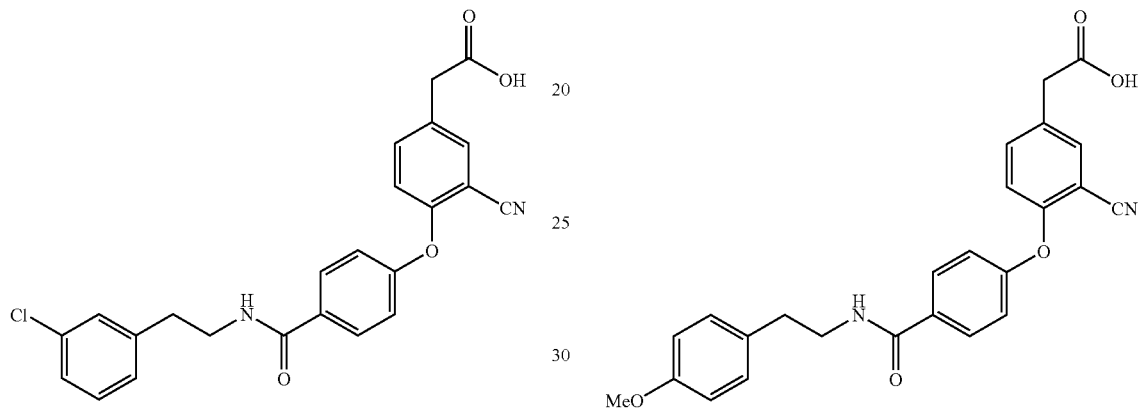

Prepared by the method of Example 72 substituting 2-(2,6-dichlorophenyl)ethanamine in Step B with 2-(3-chlorophenyl)ethanamine.

EXAMPLE 78

2-(3-cyano-4-(4-(3-fluorophenethylcarbamoyl)phenoxy)phenyl)acetic acid

Prepared by the method of Example 72, substituting 2-(2,6-dichlorophenyl)ethanamine in Step B with 2-(4-methoxyphenyl)ethanamine.

EXAMPLE 80

2-(3-cyano-4-(4-(4-methylphenethylcarbamoyl)phenoxy)phenyl)acetic acid

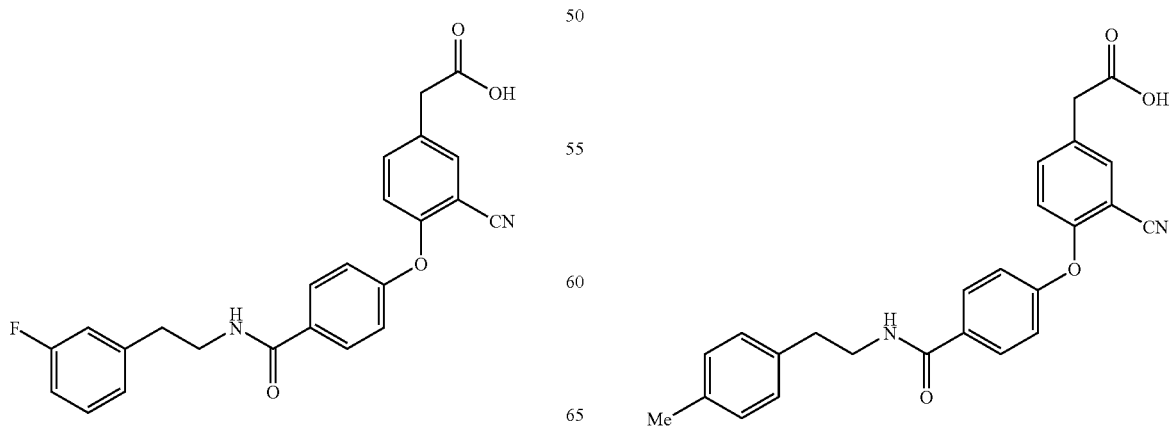

Prepared by the method of Example 72, substituting 2-(2,6-dichlorophenyl)ethanamine in Step B with 2-(4-methylphenyl)ethanamine

EXAMPLE 81

2-(3-cyano-4-(4-(3,4-dichlorophenethylcarbamoyl)phenoxy)phenyl)acetic acid

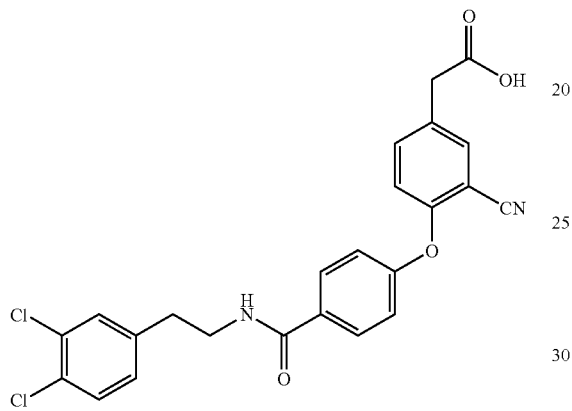

Prepared by the method of Example 72, substituting 2-(2,6-dichlorophenyl)ethanamine in Step B with 2-(3,4-dichlorophenyl)ethanamine.

EXAMPLE 82

2-(4-(4-(2-(4-chlorophenyl)-2-hydroxyethylcarbamoyl)phenoxy)-3-cyanophenyl)acetic acid

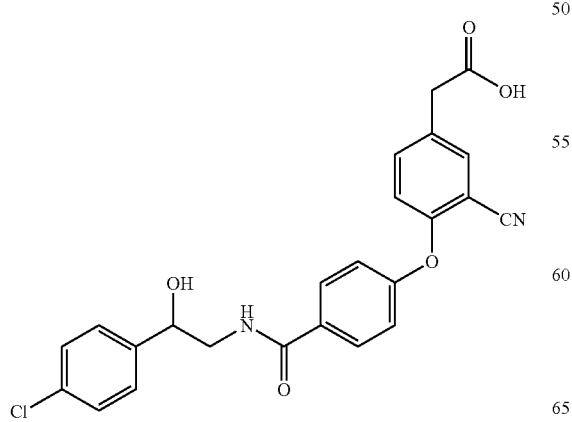

Prepared by the method of Example 72 substituting 2-(2,6-dichlorophenyl)ethanamine in Step B with 2-amino-1-(4-chlorophenyl)ethanol hydrochloride.

EXAMPLE 83

2-(4-(4-(1-(4-chlorophenyl)cyclopropylcarbamoyl)phenoxy)-3-cyanophenyl)acetic acid

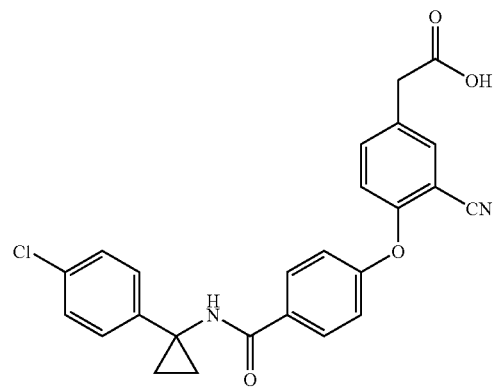

Prepared by the method of Example 72 substituting 2-(2,6-dichlorophenyl)ethanamine in Step B with 1-(4-chlorophenyl)cyclopropanamine hydrochloride.

EXAMPLE 84

2-(3-cyano-4-(4-(2-phenylcyclopropylcarbamoyl)phenoxy)phenyl)acetic acid

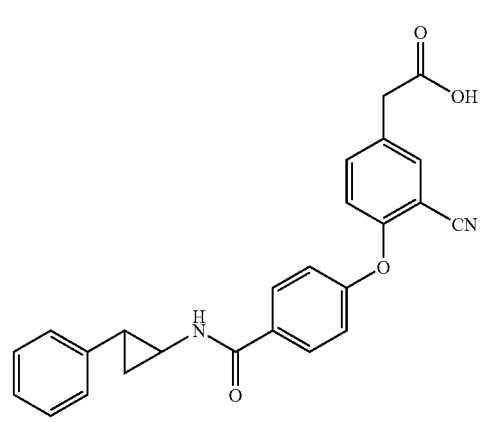

Prepared by the method of Example 72 substituting 2-(2,6-dichlorophenyl)ethanamine in Step B with 2-phenylcyclopropylamine.

EXAMPLE 85

2-(4-(4-(4-chlorophenethylcarbamoyl)phenoxy)-3-cyanophenyl)-2-fluoroacetic acid

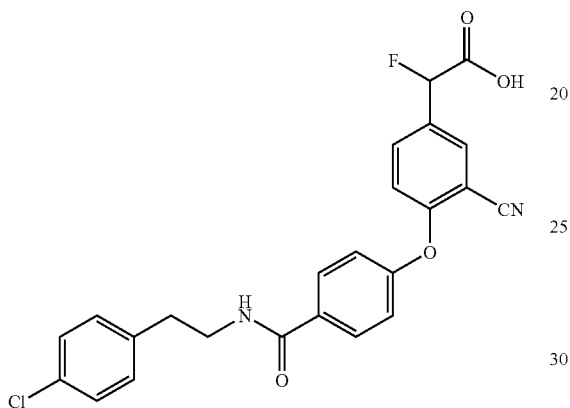

Step A: tert-Butyl 2-(4-(4-(4-chlorophenethylcarbamoyl)phenoxy)-3-cyanophenyl)acetate (0.400 g) and 4-methylbenzenesulfonyl azide (0.193 g) were dissolved in 5 ml of acetonitrile and treated with DBU (0.152 ml). The reaction was stirred for 4 hours, then concentrated, diluted with ethyl acetate and washed with water. The organic layer was dried, filtered, concentrated onto silica gel and purified by silica gel chromatography to provide tert-butyl 2-(4-(4-(4-chlorophenethylcarbamoyl)phenoxy)-3-cyanophenyl)-2-diazoacetate (0.48 g) as a bright yellow solid.

Step B: A flask was charged with tert-butyl 2-(4-(4-(4-chlorophenethylcarbamoyl)phenoxy)-3-cyanophenyl)-2-diazoacetate (0.108 g), 5 ml of ether and HF pyridine (0.30 g). The reaction was stirred at 40° C. for 30 minutes. The reaction mixture was diluted with ethyl acetate and neutralized with saturated aqueous bicarbonate solution. The organic layer was separated and washed with brine, dried, filtered and concentrated onto silica gel. The crude material was purified by silica gel chromatography to provide tert-butyl 2-(4-(4-((4-chlorophenethyl)carbamoyl)phenoxy)-3-cyanophenyl)-2-fluoroacetate (0.026 g) as a colorless oil.

Step C: A flask was charged with tert-butyl 2-(4-(4-((4-chlorophenethyl)carbamoyl)phenoxy)-3-cyanophenyl)-2-fluoroacetate (0.026 g), 0.5 ml of dichloromethane and 0.2 ml of TFA. The reaction was concentrated, and the residue was dissolved in a minimal amount of dichloromethane and placed under high vacuum to give a solid. The procedure was repeated to give 2-(4-(4-((4-chlorophenethyl)carbamoyl)phenoxy)-3-cyanophenyl)-2-fluoroacetic acid (0.024 g) as a tan solid.

EXAMPLE 86

2-(4-(4-((1-(4-chlorophenyl)cyclopropyl)methylcarbamoyl)phenoxy)-3-cyanophenyl)acetic acid

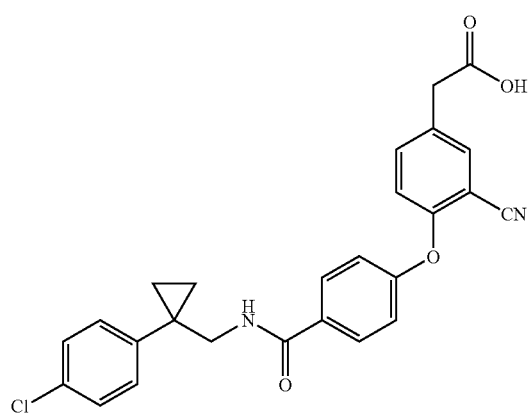

Prepared by the method of Example 72 substituting 2-(2,6-dichlorophenyl)ethanamine in Step B with (1-(4-chlorophenyl)cyclopropyl)methanamine.

EXAMPLE 87

2-(4-(4-(2-(4-chlorophenyl)cyclopropylcarbamoyl)phenoxy)-3-cyanophenyl)acetic acid

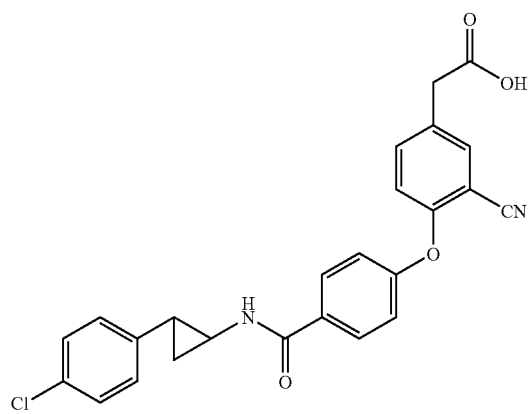

Prepared by the method of Example 72 substituting 2-(2,6-dichlorophenyl)ethanamine in Step B with 2-(4-chlorophenyl)cyclopropanamine.

EXAMPLE 88

2-(3-cyano-4-(4-(1,2,3,4-tetrahydronaphthalen-2-ylcarbamoyl)phenoxy)phenyl)acetic acid

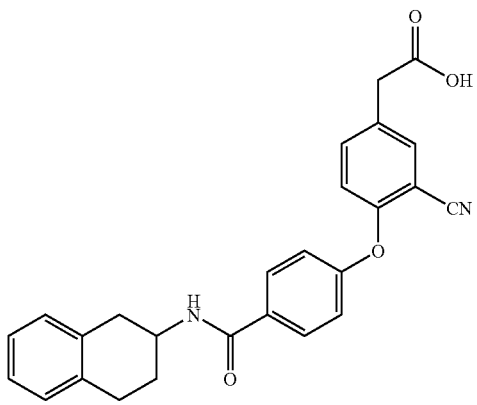

Prepared by the method of Example 72 substituting 2-(2,6-dichlorophenyl)ethanamine in Step B with 1,2,3,4-tetrahydronaphthalen-2-amine hydrochloride.

EXAMPLE 89

2-(3-cyano-4-(4-(6-methoxy-1,2,3,4-tetrahydronaphthalen-2-ylcarbamoyl)phenoxy)phenyl)acetic acid

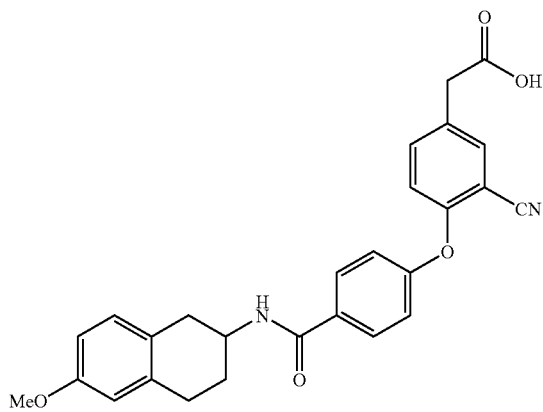

Prepared by the method of Example 72 substituting 2-(2,6-dichlorophenyl)ethanamine in Step B with 6-methoxy-1,2,3,4-tetrahydronaphthalen-2-amine hydrochloride.

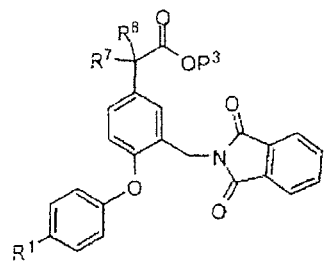

The invention claimed is:
1. A compound having the formula Ia

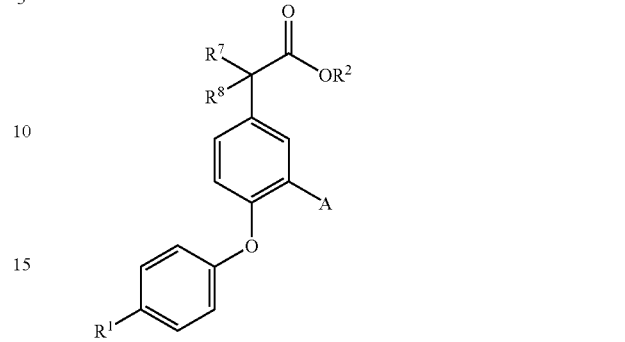

wherein
$R^1$ is $Ar^1$-$L^1$-W-$L^2$-;
$L^2$ is —$(CR^cR^d)_m$—;
W is —CONR$^{3a}$— or —NR$^{3b}$—(CO)—;
$R^{3a}$ and $R^{3b}$ are each H or methyl;
$L^1$ is —$(CR^aR^b)_n$—, —(CH=CH)—, or —O$(CR^aR^b)$—, provided that when W is —NR$^3$CO— then $L^1$ is not —(CH=CH)—;
n and m are independently 0, 1 or 2;
each $R^a$, $R^b$, $R^c$ and $R^d$ is independently H, F, methyl or cyclopropyl, or $R^a$ and $R^b$ or $R^c$ and $R^d$ together with the carbon to which they are attached form a cyclopropyl ring;
$Ar^1$ is phenyl or naphthyl, each of which is unsubstituted or substituted with one or more substituents selected independently from F, Cl, CN, $CF_3$, $CHF_2$, $CH_2F$, $SF_5$, methyl, ethyl and cyclopropyl, provided that when $Ar^1$ is naphthyl then n is 0;
$R^2$ is H, $C_1$-$C_6$ alkyl, an amino acid residue, or CHR$^e$(CH$_2$)$_q$R$^f$;
q is 1 to 6;
$R^e$ is H, methyl or ethyl;
$R^f$ is NR$^g$R$^h$ in which R$^g$ and R$^h$ each independently represents a hydrogen atom or a $C_1$-$C_4$ alkyl group, or R$^g$ and R$^h$ together with the nitrogen atom to which they are attached form a 5-6 membered heterocyclic ring optionally containing a second ring heteroatom selected from N and O, wherein said heterocyclic ring is optionally substituted with one or more groups independently selected from $C_1$-$C_6$ alkyl;
A is CN, $CH_2NH_2$, $CH_2NR^{4a}C(=O)R^5$, $CH_2NR^{4b}SO_2R^6$, Cl, OMe, (1-4C)alkyl, or cyclopropyl;
$R^{4a}$ and $R^{4b}$ are each H or methyl;
$R^5$ is $C_1$-$C_6$ alkyl, $C_1$-$C_6$ alkoxy, $C_3$-$C_6$ cycloalkyl, hetAr$^1$, or Ar$^2$;
$R^6$ is $C_1$-$C_6$ alkyl, NH($C_1$-$C_6$ alkyl), N($C_1$-$C_6$ alkyl)$_2$, Ar$^3$, or hetAr$^2$;
hetAr$^1$ is a 6 membered heteroaryl which is unsubstituted or substituted with one or more groups independently selected from a halogen atom and a group of formula —NR$^{5a}$R$^{5b}$ in which each of R$^{5a}$ and R$^{5b}$ independently represents a hydrogen atom or a (1-4C) alkyl group, or together with the nitrogen atom to which they are attached form a pyrrolidinyl, piperidinyl or morpholino group;
hetAr$^2$ is a 5-6 membered heteroaryl which is unsubstituted or substituted with one or more groups independently selected from $C_1$-$C_4$ alkyl;

Ar² is phenyl which is unsubstituted or substituted with one or more groups independently selected from a halogen atom, CN, SF₅, cyclopropyl, a $C_1$-$C_4$ alkyl group, a $C_1$-$C_4$ alkoxy group and a fluoro$C_1$-$C_4$ alkyl group;

Ar³ is as defined for Ar²; and

R⁷ and R⁸ are independently H or methyl.

2. A compound according to claim 1, wherein -L¹-W-L²- is selected from —CONH—, —CH₂CONH—, —CH₂CH₂CONH—, —CONHCH₂—, —CH₂CONHCH₂—, —NHCO—, —CH₂NHCO—, —NHCOCH₂—, —CH₂CH₂NHCO—, —CH₂NHCOCH₂—, —CH₂CH₂NHCOCH₂—, —CH₂N(CH₃)COCH₂—, cyclopropylideneCH₂NHCO, —CH₂ONHCO—, and -cyclopropylidineNHCO—.

3. A compound according to claim 1, wherein Ar¹ is a naphthyl group or a phenyl group that is unsubstituted or substituted by one or two substituents selected independently from F, Cl, CF₃, and Me.

4. A compound as claimed in claim 3, wherein Ar¹ is naphthyl, phenyl, 4-fluorophenyl, 3,4-difluorophenyl, 2-chlorophenyl, 3-chlorophenyl, 4-chlorophenyl, 3,4-dichlorophenyl, 4-chloro-3-fluorophenyl, 3-chloro-4-fluorophenyl, 4-trifluoromethylphenyl, 3-fluoro-4-trifluoromethylphenyl, 3-trifluoromethylphenyl, 2,6dichlorophenyl, 2,4-dichlorophenyl, 3 fluorophenyl and 4-methylphenyl.

5. The compound according to claim 1, wherein the 6 membered heteroaryl group in hetAr¹ is a pyridyl group and the 5-6 membered heteroaryl in hetAr² is an imidazolyl or pyridyl group.

6. A compound as claimed in claim 5, in which R⁵ is $C_1$-$C_6$ alkyl; $C_1$-$C_6$ alkoxy; $C_3$-$C_6$ cycloalkyl; pyridyl which is unsubstituted or substituted by a halogen atom or a group of formula —NR⁵ᵃR⁵ᵇ in which each of R⁵ᵃ and R⁵ᵇ independently represents a hydrogen atom or a (1-4C) alkyl group, or together with the nitrogen atom to which they are attached form a pyrrolidinyl, piperidinyl or morpholino group; or a phenyl group that is unsubstituted or substituted by one or two halogen atoms, and R⁶ is $C_1$-$C_6$ alkyl, NH(C,—$C_6$ alkyl), N($C_1$-$C_6$ alkyl)₂, a phenyl group that is unsubstituted or substituted by one or two halogen atoms, pyridyl or imidazolyl that is unsubstituted or substituted with a $C_1$-$C_3$ alkyl group.

7. A compound as claimed in claim 6, in which R⁵ is methyl, methoxy, cyclohexyl, pyrid-2-yl, pyrid-3-yl, pyrid-4-yl, 6-chloro-pyrid-3-yl, 6-amino-pyrid-3-yl, 6-pyrrolidin-1-ylpyrid-3-yl or 4-fluorophenyl and R⁶ is methyl, dimethylamino, 4-fluorophenyl, 2,4-dichlorophenyl, pyrid-3-yl, 1-methylimidazol-5-yl, or 6-dimethylaminopyrid-3-yl.

8. A compound as claimed in claim 1, in which A is selected from cyano, acetamidomethyl, cyclohexylamidomethyl, methoxycarbonylaminomethyl, picolinamidomethyl, nicotinamidomethyl, isonicotinamidomethyl, 6-chloropyrid-3-ylamidomethyl, 6-aminopyrid-3-ylamidomethyl, 6-pyrrolidin-1-ylpyrid-3-ylamidomethyl, 4-fluorobenzamidomethyl, methylsulfonamidomethyl, N,N-dimethylsulfamoylamino, 4-fluorophenylsulfonamidomethyl, 2,4-dichlorophenylsulfonamidomethyl, 1-methylimidazol-5-ylsulfonamidomethyl, pyrid-3-ylsulfonamidomethyl, 6-dimethylaminopyrid-3-ylamidomethyl, 2-(4-fluorophenylsulfonamido)acetamidomethyl, (N—methylmethylsulfonamido)methyl, Cl, methyl, ethyl, cyclopropyl, and CH₂NH₂.

9. A compound as claimed in claim 8, in which A is selected from cyano, acetamidomethyl, cyclohexylamidomethyl, methoxycarbonylaminomethyl, picolinamidomethyl, nicotinamidomethyl, isonicotinamidomethyl, 4-fluorobenzamidomethyl, methylsulfonamido-methyl, N,N-dimethylsulfamoylamino, 4-fluorophenylsulfonamidomethyl, 2,4-dichloro-phenylsulfonamidomethyl, pyrid-3-ylsulfonamidomethyl, 6-dimethylaminopyrid-3-ylamidomethyl, 2-(4-fluorophenylsulfonamido)acetamidomethyl, (N—methylmethylsulfonamido)methyl, Cl, methyl, ethyl, cyclopropyl, and CH₂NH₂.

10. A compound as claimed in claim 1, in which R² is hydrogen.

11. A compound as claimed in claim 1, in which R⁷ and R⁸ are H.

12. A pharmaceutical composition, which comprises a compound of formula (I) as defined in claim 1, or a pharmaceutically acceptable salt thereof, and a pharmaceutically acceptable diluent or carrier.

13. A process for the preparation a compound as defined in claim 1, which comprises:

(a) for a compound of formula (I) in which A is CN, and R⁷ and R⁸ are independently H or Me, reacting a corresponding compound having the formula:

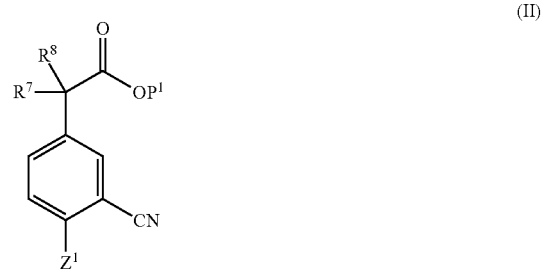

(II)

in which P¹ represents a hydrogen atom or a carboxyl protecting group and Z¹ represents a leaving atom or group, with a corresponding compound having the formula

(III)

in the presence of a base; or (b) for a compound of formula (I) in which A is —CH₂NH₂, and R⁷ and R⁸ are independently H or Me, reducing a corresponding compound formula (IV)

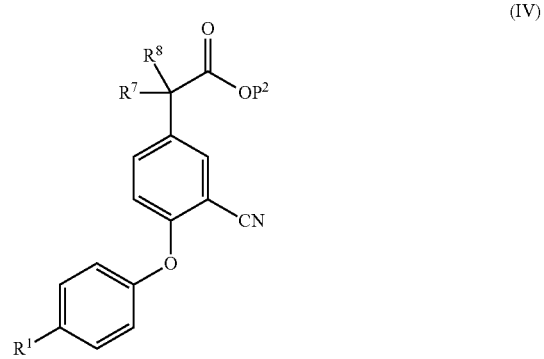

(IV)

in which P² is as defined for P¹; or (c) for a compound of formula (I) in which A is —CH₂NH₂, and R⁷ and R⁸ are independently H or Me, cleaving a corresponding compound of formula (V)

(V)

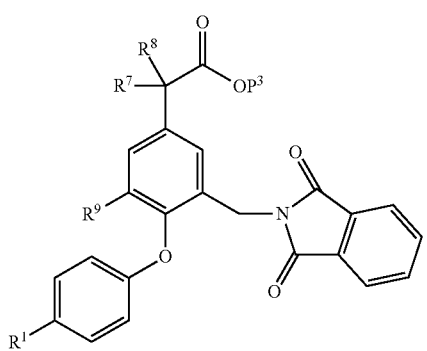

in which $P^3$ is as defined for $P^1$; or (d) for a compound of formula (I) in which A is $CH_2NR^4C(=O)R^5$ or $CH_2NR^4SO_2R^6$, and $R^7$ and $R^8$ are independently H or Me, reacting a corresponding compound of formula (VI)

(VI)

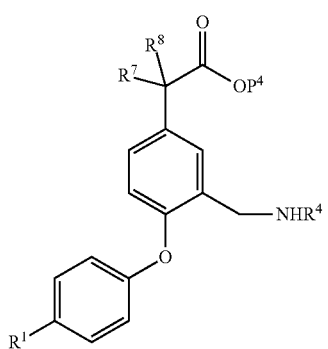

in which $P^4$ is as defined for $P^1$; with a compound of formula $R^5COZ^2$ or $R^6SO_2Z^3$ in which $Z^2$ and $Z^3$ each represents a leaving atom or group; or (e) for a compound of formula (I) in which $R^7$ and $R^8$ are independently H or Me, coupling a compound of formula (VII)

(VII)

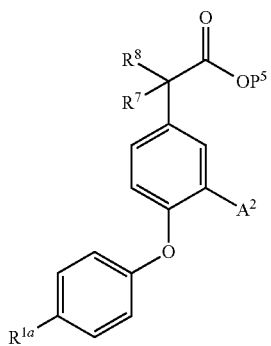

in which $P^5$ is as defined for $P^1$, $A^2$ represents A or a protected form thereof and $R^{1a}$ represents H—$X^a$-$L^2$- in which $X^a$ represents HN or OC(=O), or a reactive derivative thereof; with a compound of formula (VIII)

$Ar^1\text{-}L^1\text{-}X^b\text{—}H$ (VIII)

in which $X^b$ represents C(=O)O or NH, or a reactive derivative thereof; or (f) for a compound of formula (I) in which A is Cl, and $R^7$ and $R^8$ are independently H or Me, coupling a corresponding compound having the formula (IX)

(IX)

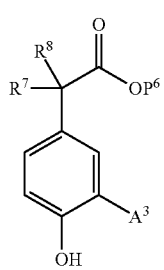

in which $A^3$ is Cl, and $P^6$ is as defined for $P^1$, with a corresponding compound having the formula (X)

(X)

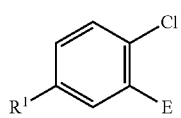

wherein E is an electron withdrawing group, in the presence of a base; and if desired removing said electron withdrawing group; or (g) for a compound of formula (I) in which A is OMe or (1-4C)alkyl, and $R^7$ and $R^8$ are independently H or Me, coupling a corresponding compound having the formula (XI)

(XI)

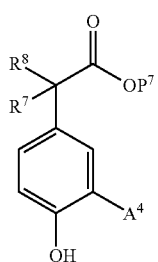

in which $A^4$ is OMe or (1-4C)alkyl, respectively, and $P^7$ is as defined for $P^1$, with a corresponding compound having the formula (XII)

(XII)

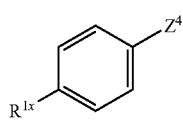

in the presence of a base, in which $Z^4$ represents a leaving atom or group, and $R^{1x}$ represents an electron withdrawing group convertible into a group $R^1$; or (h) for a compound of formula (I) in which A is cyclopropyl, and $R^7$ and $R^8$ are H, coupling a corresponding compound having the formula (XIV)

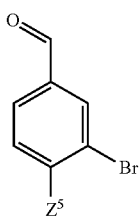

(XIV)

in which $Z^5$ is a leaving group or atom, with a compound having the formula (XV)

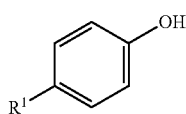

(XV)

in the presence of a base, followed by converting the carbonyl group to a carboxyl group; or (i) for a compound of formula (I) in which A is methyl, and $R^7$ and $R^8$ are independently H or Me, reacting a corresponding compound having the formula (XVI)

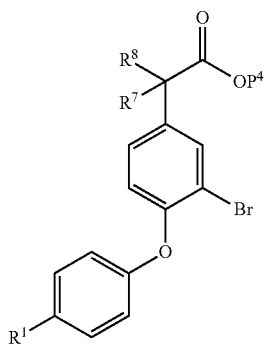

(XVI)

with a compound having the formula $A^5$-ZnX, in the presence of a palladium (0) catalyst, or with a compound having the formula $A^5B(OH)_2$ in the presence of a base and a palladium (0) catalyst, where $A^5$ is methyl, and X is a halide; or (j) for a compound of formula (I) in which $R^7$ is F, and $R^8$ is H, treating a corresponding compound having the formula (XVII)

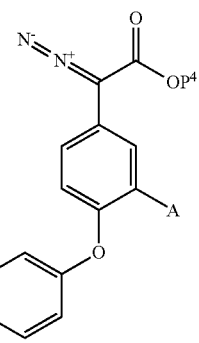

(XVII)

with hydrogen fluoride; and removing any protecting group or groups and, if desired, forming a salt.

* * * * *

UNITED STATES PATENT AND TRADEMARK OFFICE
CERTIFICATE OF CORRECTION

PATENT NO. : 8,183,289 B2  
APPLICATION NO. : 12/438112  
DATED : May 22, 2012  
INVENTOR(S) : Doherty et al.

Page 1 of 2

It is certified that error appears in the above-identified patent and that said Letters Patent is hereby corrected as shown below:

In the Claims

Column 79, lines 22-23, Claim 4:  
Replace "3 -chloro-4-fluorophenyl" with --3-chloro-4-fluorophenyl--.

Column 79, lines 23-24, Claim 4:  
Replace "3 -fluoro-4-trifluoromethylphenyl" with --3-fluoro-4-trifluoromethylphenyl--.

Column 79, line 24, Claim 4:  
Replace "3 -trifluoromethylphenyl" with --3-trifluoromethylphenyl--.

Column 79, lines 24-25, Claim 4:  
Replace "2,6dichlorophenyl" with --2,6-dichlorophenyl--.

Column 79, line 25, Claim 4:  
Replace "3 fluorophenyl" with --3-fluorophenyl--.

Column 79, line 57, Claim 8:  
Replace "pyrid-3 -ylsulfonamidomethyl" with --pyrid-3-ylsulfonamidomethyl--.

Column 79, lines 57-58, Claim 8:  
Replace "6-dimethylaminopyrid-3 -ylamidomethyl" with --6-dimethylaminopyrid-3-ylamidomethyl--.

Signed and Sealed this  
Eighth Day of September, 2015

Michelle K. Lee  
*Director of the United States Patent and Trademark Office*

CERTIFICATE OF CORRECTION (continued)
U.S. Pat. No. 8,183,289 B2

Column 81, line 1, Claim 13:
Replace

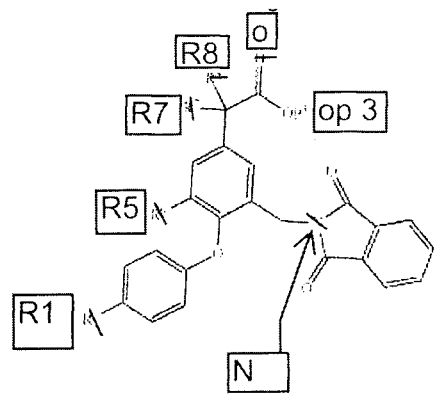

With: